(12) United States Patent
Hearing et al.

(10) Patent No.: US 8,198,244 B2
(45) Date of Patent: Jun. 12, 2012

(54) REGULATION OF SKIN CHARACTERISTICS BY DICKKOPF1 (DKK1)

(75) Inventors: Vincent Hearing, Leesburg, VA (US); Yuji Yamaguchi, Osaka (JP); Thierry Passeron, Nice (FR)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 235 days.

(21) Appl. No.: 12/518,052

(22) PCT Filed: Dec. 7, 2007

(86) PCT No.: PCT/US2007/086855
§ 371 (c)(1), (2), (4) Date: Jun. 5, 2009

(87) PCT Pub. No.: WO2008/070859
PCT Pub. Date: Jun. 12, 2008

(65) Prior Publication Data
US 2010/0317590 A1    Dec. 16, 2010

Related U.S. Application Data

(60) Provisional application No. 60/873,874, filed on Dec. 7, 2006.

(51) Int. Cl.
*A61K 38/00* (2006.01)
(52) U.S. Cl. ..................................... 514/18.6
(58) Field of Classification Search .................. None
See application file for complete search history.

(56) References Cited

U.S. PATENT DOCUMENTS

| | | | |
|---|---|---|---|
| 6,750,229 B2 | 6/2004 | Seiberg et al. | |
| 6,841,539 B1 | 1/2005 | Mehta et al. | |
| 7,057,017 B2 | 6/2006 | McCarthy | |
| 2004/0223952 A1 | 11/2004 | Have-Opbroek | |
| 2006/0127393 A1 | 6/2006 | Li et al. | |

FOREIGN PATENT DOCUMENTS

WO    WO 2006/015497    *    2/2006

OTHER PUBLICATIONS

Yamaguchi, "Site Specific (Topographical) Interactions Between Mesenchyme and Epithelium: Induction of Palmoplantar Phenotype by dickkopf-1 Highly Expressed by Palmoplantar Fibroblasts," (oral presentation given at The 20th Annual Meeting of Japanese Society for Pigment Cell Research, Nov. 26, 2006, Matsumoto, Japan) 36 pages.
Atiyeh et al., "New Technologies for Burn Wound Closure and Healing—Review of the Literature," *Burns 31*:944-956, 2005.
Chang, "Patterning Skin Pigmentation via Dickkopf," *J. Invest. Dermatol. 127*:994-995, 2007.
Feng et al., "Non-Native Hydrophobic Interactions in a Hidden Folding Intermediate," *Biochem. 42*:12461-12465, 2003.
Hanafusa et al., "Intractable Wounds Caused by Arteriosclerosis Obliterans with End-Stage Renal Disease Treated by Aggressive Debridement and Epidermal Grafting," *J. Am. Acad. Dermatol. 57*:322-326, 2007.
Hearing, "Regulating Melanosome Transfer: Who's Driving the Bus?," *Pigment Cell Res. 20*:334-335, 2007.
Krishnan et al., "Regulation of Bone Mass by Wnt Signaling," *J. Clin. Invest. 116*:1202-1209, 2006.
Reis et al., "Keratin 9 Gene Mutations in Epidermolytic Palmoplantar Keratoderma (EPPK)," *Nature Genet. 6*:174-179, 1994.
Sweitzer et al., "What is the Future of Diabetic Wound Care?," *The Diabetics Educator 32*:197-210, 2006.
Valencia et al., "Sorting of Pmel17 to Melanosomes through the Plasma Membrane by AP1 and AP2: Evidence for the Polarized Nature of Melanocytes," *J. Cell Sci. 119*:1080-1091, 2006.
Wong et al., "The Role of Fibroblasts in Tissue Engineering and Regeneration," *Br. J. Dermatol. 156*:1149-1155, 2007.
Yamaguchi et al., "Epithelial-Mesenchymal Interactions in Wounds," *Arch. Dermatol. 137*:621-628, 2001.
Yamaguchi et al., "Mesenchymal-Epithelial Interactions in the Skin: Increased Expression of Dickkopf1 by Palmoplantar Fibroblasts Inhibits Melanocyte Growth and Differentiation," *J. Cell Biol. 165*:275-285, 2004.
Yamaguchi et al., "Rapid Healing of Intractable Diabetic Foot Ulcers with Exposed Bones Following a Novel Therapy of Exposing Bone Marrow Cells and Then Granting Epidermal Sheets," *Br. J. Dermatol. 151*:1019-1028, 2004.
Yamaguchi et al., "Increased Expression of Dickkopf1 by Palmoplantar Fibroblasts Inhibits Melanocyte Growth and Differentiation," *J. Cell Biol. 165*:275-285, 2004.
Yamaguchi et al., "Mesenchymal-Epithelial Interactions in the Skin: Aiming for Site-Specific Tissue Regeneration," *J. Dermatol. Sci. 40*:1-9, 2005.
Yamaguchi, "Site Specific Interactions Between Mesenchyme and Epithelium: Induction of Palmoplantar Phenotype by Dickkopf-1 Highly Expressed by Palmoplantar Fibroblasts," *Pigment Cell Res. 19*:647-658, 2006 (Abstract WS-2, The 20th Annual Meeting of Japanese Society for Pigment Cell Research, Nov. 25-26, 2006, Matsumoto, Japan).
Yamaguchi et al., "The Effects of Dickkopf 1 on Gene Expression and Wnt Signaling by Melanocytes: Mechanisms Underlying Its Suppression of Melanocyte Function and Proliferation," *J. Invest. Dermatol. 127*:1217-1225, 2007 (published on line Dec. 7, 2006).
Yamaguchi et al., "The Regulation of Skin Pigmentation," *J. Biol. Chem. 282*:27557-27561, 2007.
Yamaguchi et al., "Dickkopf 1 (DKK1) Regulates Skin Pigmentation and Thickness by Affecting Wnt/β-catenin Signaling in Keratinocytes," *FASEB J. 22*:1009-1020, 2008 (published on line Nov. 5, 2007).
"Developmental Genetics of Hair Formation," http://8e.devbio.com/article.php?ch=12&id=285, printed from the Internet on Nov. 11, 2006.

* cited by examiner

*Primary Examiner* — Christina Bradley
(74) *Attorney, Agent, or Firm* — Klarquist Sparkman, LLP

(57) ABSTRACT

The present disclosure is generally related to methods of inducing non-palmoplantar skin to develop a palmoplantar phenotype, for example, methods for increasing skin thickness, decreasing skin pigmentation, and/or decreasing hair growth. In particular, disclosed herein are methods of using topical administration of DKK1 to increase skin thickness, decrease skin pigmentation, or reduce hair growth. Also disclosed are topical DKK1 compositions for inducing non-palmoplantar skin to develop a palmoplantar phenotype.

24 Claims, 15 Drawing Sheets

A) 2 hr treatment

B) 5 d treatment

|  | DKK1-transfected | mock-transfected | |
|---|---|---|---|
| cell number (n=12) | 29.3 ± 1.9 | 24.0 ± 1.2 | $p < .05$ |
| pigmentation (n=10) | 0.14 ± .04 | 0.44 ± .09 | $p < .01$ |

| protein | DKK1 | mock | n= | p= |
|---|---|---|---|---|
| αKLEIP | 142± 8 | 134± 6 | 3 | <.05 |
| PAR2 | not det | not det | | |
| β-cat (nucleus) | 114±10 | 138±14 | 3 | <.05 |
| β-cat (cyto) | 118±16 | 150±13 | 4 | <.02 |
| PKCα | 82±18 | 59±12 | 5 | <.05 |
| PKCβ2 | 151± 5 | 127± 5 | 5 | <.05 |
| ERK | 150±20 | 148±11 | 3 | NS |
| pERK | 198±13 | 186±16 | 4 | <.05 |
| GSK3β | 62±20 | 77±23 | 5 | NS |
| pGSK3β | 35± 3 | 19± 3 | 4 | <.01 |
| DKK1 | 108± 7 | 39± 4 | 3 | <.02 |
| β-actin | 163±13 | 160±13 | 3 | NS |

SEQUENCE LISTING

```
<160> NUMBER OF SEQ ID NOS: 32

<210> SEQ ID NO 1
<211> LENGTH: 20
<212> TYPE: DNA
<213> ORGANISM: Artificial sequence
<220> FEATURE:
<223> OTHER INFORMATION: Primer

<400> SEQUENCE: 1
agtgccaagt ttgctgcttt                                             20
```

```
<210> SEQ ID NO 2
<211> LENGTH: 20
<212> TYPE: DNA
<213> ORGANISM: Artificial sequence
<220> FEATURE:
<223> OTHER INFORMATION: Primer

<400> SEQUENCE: 2
acaatgagga cgtccctgtc                                                    20

<210> SEQ ID NO 3
<211> LENGTH: 20
<212> TYPE: DNA
<213> ORGANISM: Artificial sequence
<220> FEATURE:
<223> OTHER INFORMATION: Primer

<400> SEQUENCE: 3
caagtttgct gggatggagt                                                    20

<210> SEQ ID NO 4
<211> LENGTH: 20
<212> TYPE: DNA
<213> ORGANISM: Artificial sequence
<220> FEATURE:
<223> OTHER INFORMATION: Primer

<400> SEQUENCE: 4
tgtcaaatag ggggaagctg                                                    20

<210> SEQ ID NO 5
<211> LENGTH: 20
<212> TYPE: DNA
<213> ORGANISM: Artificial sequence
<220> FEATURE:
<223> OTHER INFORMATION: Primer

<400> SEQUENCE: 5
gctcagagtc ccagttccag                                                    20

<210> SEQ ID NO 6
<211> LENGTH: 20
<212> TYPE: DNA
<213> ORGANISM: Artificial sequence
<220> FEATURE:
<223> OTHER INFORMATION: Primer

<400> SEQUENCE: 6
tcccttcata cgtggacaca                                                    20

<210> SEQ ID NO 7
<211> LENGTH: 20
<212> TYPE: DNA
<213> ORGANISM: Artificial sequence
<220> FEATURE:
<223> OTHER INFORMATION: Primer

<400> SEQUENCE: 7
aagtgcatct ctcggcagtt                                                    20

<210> SEQ ID NO 8
<211> LENGTH: 20
<212> TYPE: DNA
<213> ORGANISM: Artificial sequence
<220> FEATURE:
<223> OTHER INFORMATION: Primer

<400> SEQUENCE: 8
```
tgcagtttcc atcagagcac                                                20

<210> SEQ ID NO 9
<211> LENGTH: 20
<212> TYPE: DNA
<213> ORGANISM: Artificial sequence
<220> FEATURE:
<223> OTHER INFORMATION: Primer

<400> SEQUENCE: 9
gctgctgatc gacctgtgta                                                20

<210> SEQ ID NO 10
<211> LENGTH: 20
<212> TYPE: DNA
<213> ORGANISM: Artificial sequence
<220> FEATURE:
<223> OTHER INFORMATION: Primer

<400> SEQUENCE: 10
gatggtgctg cagaagatga                                                20

<210> SEQ ID NO 11
<211> LENGTH: 20
<212> TYPE: DNA
<213> ORGANISM: Artificial sequence
<220> FEATURE:
<223> OTHER INFORMATION: Primer

<400> SEQUENCE: 11
agagagaagt ccctgcacca                                                20

<210> SEQ ID NO 12
<211> LENGTH: 20
<212> TYPE: DNA
<213> ORGANISM: Artificial sequence
<220> FEATURE:
<223> OTHER INFORMATION: Primer

<400> SEQUENCE: 12
ttgtgagcat tgtcctcagc                                                20

<210> SEQ ID NO 13
<211> LENGTH: 20
<212> TYPE: DNA
<213> ORGANISM: Artificial sequence
<220> FEATURE:
<223> OTHER INFORMATION: Primer

<400> SEQUENCE: 13
acagtggggg tgtacgagtc                                                20

<210> SEQ ID NO 14
<211> LENGTH: 20
<212> TYPE: DNA
<213> ORGANISM: Artificial sequence
<220> FEATURE:
<223> OTHER INFORMATION: Primer

<400> SEQUENCE: 14
gagatgtagg ggacccactg                                                20

<210> SEQ ID NO 15
<211> LENGTH: 25
<212> TYPE: DNA
<213> ORGANISM: Artificial sequence

```
<220> FEATURE:
<223> OTHER INFORMATION: Primer

<400> SEQUENCE: 15
agagagcgag tgcccaggca tgaac                                  25

<210> SEQ ID NO 16
<211> LENGTH: 25
<212> TYPE: DNA
<213> ORGANISM: Artificial sequence
<220> FEATURE:
<223> OTHER INFORMATION: Primer

<400> SEQUENCE: 16
tctttggcca gtgctcttgc ttcag                                  25

<210> SEQ ID NO 17
<211> LENGTH: 20
<212> TYPE: DNA
<213> ORGANISM: Artificial sequence
<220> FEATURE:
<223> OTHER INFORMATION: Primer

<400> SEQUENCE: 17
accacagtcc atgccatcac                                        20

<210> SEQ ID NO 18
<211> LENGTH: 20
<212> TYPE: DNA
<213> ORGANISM: Artificial sequence
<220> FEATURE:
<223> OTHER INFORMATION: Primer

<400> SEQUENCE: 18
tccaccaccc tgttgctgta                                        20

<210> SEQ ID NO 19
<211> LENGTH: 20
<212> TYPE: DNA
<213> ORGANISM: Artificial sequence
<220> FEATURE:
<223> OTHER INFORMATION: Primer

<400> SEQUENCE: 19
tggctgtgtt aggagggttc                                        20

<210> SEQ ID NO 20
<211> LENGTH: 20
<212> TYPE: DNA
<213> ORGANISM: Artificial sequence
<220> FEATURE:
<223> OTHER INFORMATION: Primer

<400> SEQUENCE: 20
ctactgccat gagctgtcca                                        20

<210> SEQ ID NO 21
<211> LENGTH: 20
<212> TYPE: DNA
<213> ORGANISM: Artificial sequence
<220> FEATURE:
<223> OTHER INFORMATION: Primer

<400> SEQUENCE: 21
ggcgaggaga gaagaggaat                                        20
```

```
<210> SEQ ID NO 22
<211> LENGTH: 20
<212> TYPE: DNA
<213> ORGANISM: Artificial sequence
<220> FEATURE:
<223> OTHER INFORMATION: Primer

<400> SEQUENCE: 22
caactctgcc acgttaagca                                              20

<210> SEQ ID NO 23
<211> LENGTH: 20
<212> TYPE: DNA
<213> ORGANISM: Artificial sequence
<220> FEATURE:
<223> OTHER INFORMATION: Primer

<400> SEQUENCE: 23
gttttgggtc tggtgttgct                                              20

<210> SEQ ID NO 24
<211> LENGTH: 20
<212> TYPE: DNA
<213> ORGANISM: Artificial sequence
<220> FEATURE:
<223> OTHER INFORMATION: Primer

<400> SEQUENCE: 24
gacctctaat gcctggtgga                                              20

<210> SEQ ID NO 25
<211> LENGTH: 20
<212> TYPE: DNA
<213> ORGANISM: Artificial sequence
<220> FEATURE:
<223> OTHER INFORMATION: Primer

<400> SEQUENCE: 25
cacgccaact agcacaaaga                                              20

<210> SEQ ID NO 26
<211> LENGTH: 20
<212> TYPE: DNA
<213> ORGANISM: Artificial sequence
<220> FEATURE:
<223> OTHER INFORMATION: Primer

<400> SEQUENCE: 26
aattcgactg gttgggactg                                              20

<210> SEQ ID NO 27
<211> LENGTH: 20
<212> TYPE: DNA
<213> ORGANISM: Artificial sequence
<220> FEATURE:
<223> OTHER INFORMATION: Primer

<400> SEQUENCE: 27
tgtcaaactg acaccccgta                                              20

<210> SEQ ID NO 28
<211> LENGTH: 20
<212> TYPE: DNA
<213> ORGANISM: Artificial sequence
<220> FEATURE:
<223> OTHER INFORMATION: Primer

<400> SEQUENCE: 28
```

```
atttactcgg gccacaacag                                               20

<210> SEQ ID NO 29
<211> LENGTH: 20
<212> TYPE: DNA
<213> ORGANISM: Artificial sequence
<220> FEATURE:
<223> OTHER INFORMATION: Primer

<400> SEQUENCE: 29
acaccgtgga tactgcttcc                                               20

<210> SEQ ID NO 30
<211> LENGTH: 20
<212> TYPE: DNA
<213> ORGANISM: Artificial sequence
<220> FEATURE:
<223> OTHER INFORMATION: Primer

<400> SEQUENCE: 30
ccgatccatt cccctttat                                                20

<210> SEQ ID NO 31
<211> LENGTH: 20
<212> TYPE: DNA
<213> ORGANISM: Artificial sequence
<220> FEATURE:
<223> OTHER INFORMATION: Primer

<400> SEQUENCE: 31
tgctagcagc ctctctctcc                                               20

<210> SEQ ID NO 32
<211> LENGTH: 20
<212> TYPE: DNA
<213> ORGANISM: Artificial sequence
<220> FEATURE:
<223> OTHER INFORMATION: Primer

<400> SEQUENCE: 32
cttcaagggg aaccagatga                                               20
```

REGULATION OF SKIN CHARACTERISTICS BY DICKKOPF1 (DKK1)

CROSS REFERENCE TO RELATED APPLICATION

This is the U.S. National Stage of International Application No. PCT/US2007/086855, filed Dec. 7, 2007, which was published in English under PCT Article 21(2), which in turn claims the benefit of U.S. Provisional Application No. 60/873,874 filed Dec. 7, 2006. Both applications are incorporated herein in their entirety.

FIELD OF THE DISCLOSURE

The present disclosure is generally related to methods of inducing non-palmoplantar skin to develop a palmoplantar phenotype, for example, methods for increasing skin thickness, decreasing skin pigmentation, and/or decreasing hair growth.

BACKGROUND

There are a number of topographical, anatomical, and site-specific differences between human skin on the sole and the palm (also called palmoplantar skin or palmoplantaris) and on the trunk (also called non-palmoplantar skin or non-palmoplantaris) in terms of thickness and pigmentation. Not only is palmoplantar skin much thicker and less hairy than is skin in other regions of the body, but melanocytes in those areas are less dense and produce significantly less melanin pigment than non-palmoplantar skin.

Many dermatological conditions would be improved by an increase in skin thickness, a decrease in skin pigmentation, or a decrease in hair growth. For instance, skin thickening would be desirable in a subject that has a skin graft, a skin ulcer, a skin abrasion or avulsion/excision (such as one that leaves a volume defect), an injury or predisposition to injury caused by a repetitive impact or mechanical stress, age-related skin changes (for instance, thinning or wrinkled skin), or skin damage due to steroid treatment. A decrease in skin pigmentation would be helpful when the subject has a condition such as uneven skin pigmentation, hyperpigmentation, post-inflammatory pigmentation, ephelides, fragrance dermatitis, sun-damaged skin, a pigmented birthmark, lentigos, lichen simplex chronicus, melasma, porphyria cutanea tarda, Addison's disease, Peutz-Jeghers syndrome, acanthosis nigricans, or when depigmentation is desired in a subject with widespread vitiligo. Decreased hair growth may be cosmetically desirable on an upper or lower extremity or axillary skin, or when a subject has, for instance, hirsutism, congenital adrenal hyperplasia, polycystic ovarian syndrome, hypertrichosis, porphyria cutanea tarda, or increased vellus hair due to anorexia nervosa.

Given the foregoing, it would be desirable to have methods or compositions that could induce non-palmoplantar skin to adopt one or more of the characteristics of palmoplantar skin.

SUMMARY OF THE DISCLOSURE

Disclosed herein is a method for inducing non-palmoplantar skin (for instance, skin of the trunk, face, or a non-palmoplantar extremity such as a finger or toe) to develop a palmoplantar phenotype (for instance, becoming one or more or all of thicker, less pigmented, and less hairy). The method includes topically applying an effective amount of DKK1 to non-palmoplantar skin, which induces the non-palmoplantar skin to develop a palmoplantar phenotype. In some embodiments, the method is a method of increasing skin thickness, whereas in other embodiments, the method is a method of reducing skin pigmentation. In still other embodiments, the method is a method of reducing hair growth, and in still other embodiments, the method is a method of treating or preventing melanoma. Also disclosed are pharmaceutical compositions that include an amount of DKK1 sufficient to induce non-palmoplantar skin to develop a palmoplantar phenotype and a carrier for topical administration.

The foregoing and other features and advantages of the invention will become more apparent from the following detailed description of a several embodiments which proceeds with reference to the accompanying figures.

BRIEF DESCRIPTION OF THE FIGURES

FIG. 1A is a pair of digital images of immunoblot gels. The intensity of the 35 kDa DKK1 band is higher in palmoplantar fibroblasts (Palm1, Palm2) than in non-palmoplantar fibroblasts (Trunk1, Trunk2). FIG. 1B is a pair of digital images showing an immunocytochemical analysis; high levels of DKK1 are seen in palmoplantar fibroblasts (Palm3) compared with non-palmoplantar fibroblasts (Trunk3). Nuclei are stained with DAPI.

FIG. 10 is a set of digital images of immunocytochemistry of keratinocytes treated with (+) or without (−) rhDKK1 for three days.

FIG. 13A shows the visual aspect of the reconstructed epidermis after 10 days of treatment with or without rhDKK1. The epidermis treated with rhDDK1 appeared thicker and less pigmented than the control. FIG. 13B shows Fontana-Masson staining after 4, 7 and 10 days of treatment with or without rhDKK1. The untreated epidermis showed more melanin than that treated by rhDKK1. FIG. 13C shows Hematoxylin-eosin staining after 4, 7 and 10 days of treatment with or without rhDKK1. The DKK1-treated skin had a thicker stratum corneum than controls.

SEQUENCES

Figure 1:
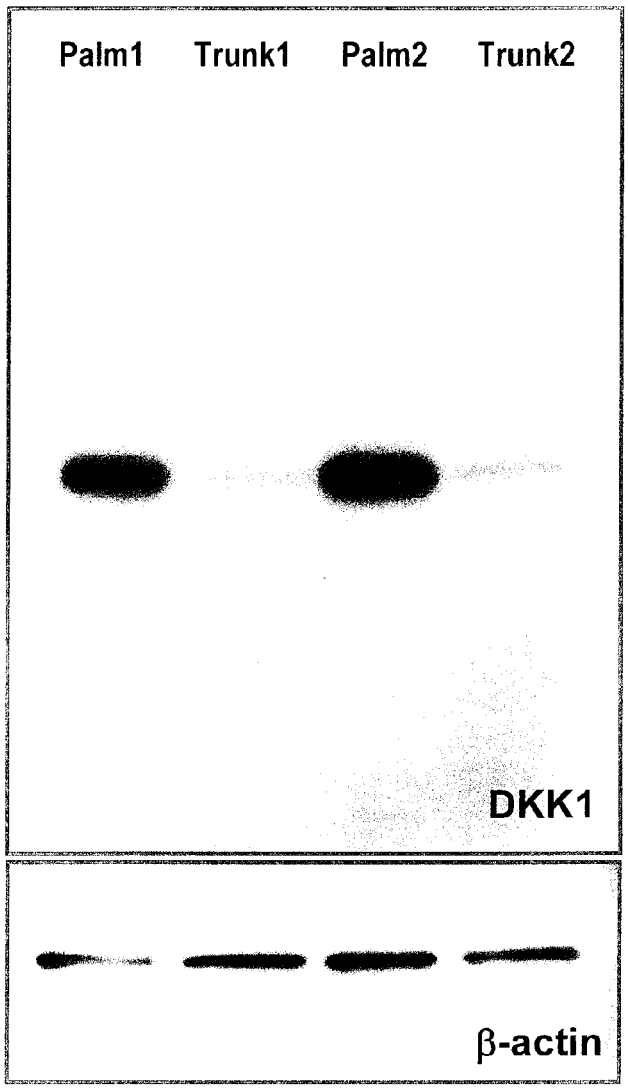
FIG. 1 is a set of digital images showing DKK1 expression by palmoplantar and by non-palmoplantar fibroblasts.
Figure 1:
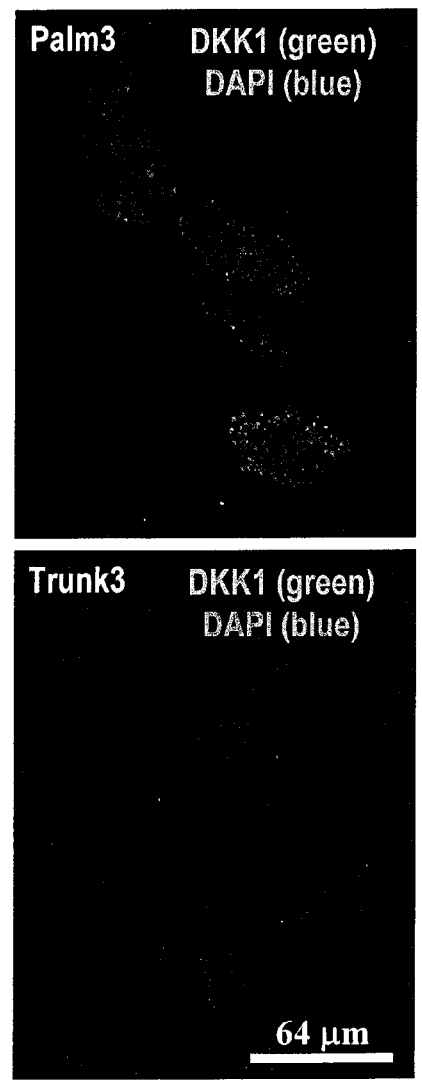

The nucleic sequences listed herein and/or in the accompanying sequence listing are shown using standard letter abbreviations for nucleotide bases as defined in 37 C.F.R. 1.822. Only one strand of each nucleic acid sequence is shown, but the complementary strand is understood as included by any reference to the displayed strand.

SEQ ID NO: 1 is a human PKCβ1 sense primer
SEQ ID NO: 2 is a PKCβ1 antisense primer
SEQ ID NO: 3 is a human Krn1 sense primer
SEQ ID NO: 4 is a Krn1 antisense primer
SEQ ID NO: 5 is a human LRP6 sense primer
SEQ ID NO: 6 is an LRP6 antisense primer
SEQ ID NO: 7 is a human LDLR sense primer
SEQ ID NO: 8 is an LDLR antisense primer
SEQ ID NO: 9 is a human GPR51 sense primer
SEQ ID NO: 10 is a GPR51 antisense primer
SEQ ID NO: 11 is a human TNFRSF10A sense primer
SEQ ID NO: 12 is a TNFSF10A antisense primer
SEQ ID NO: 13 is a human Gadd45β sense primer
SEQ ID NO: 14 is a Gadd45β antisense primer
SEQ ID NO: 15 is a MITF sense primer
SEQ ID NO: 16 is a MITF antisense primer
SEQ ID NO: 17 is a GAPDH sense primer
SEQ ID NO: 18 is a GAPDH antisense primer 5'-tccaccac-cctgttgctgta-3'
SEQ ID NO: 19 is a human KLEIP sense primer
SEQ ID NO: 20 is a KLEIP antisense primer
SEQ ID NO: 21 is a human GJB6 sense primer
SEQ ID NO: 22 is a GJB6 antisense primer
SEQ ID NO: 23 is a human Snrpn sense primer
SEQ ID NO: 24 is a Snrpn antisense primer
SEQ ID NO: 25 is a human BMP2IK sense primer
SEQ ID NO: 26 is a BMP2IK antisense primer
SEQ ID NO: 27 is a human P4HA2 sense primer
SEQ ID NO: 28 is a P4HA2 antisense primer
SEQ ID NO: 29 is a human Tulp3 sense primer
SEQ ID NO: 30 is a Tulp3 antisense primer
SEQ ID NO: 31 is a human PAR2 sense primer
SEQ ID NO: 32 is a PAR2 antisense primer

DETAILED DESCRIPTION OF SEVERAL EMBODIMENTS

I. Overview of Several Embodiments

The methods disclosed herein are based on the surprising finding that topically-applied DKK1 causes non-palmoplantar skin (for instance, skin of the trunk, head, arms, or legs) to take on the characteristics of palmoplantar skin (for instance, becoming more like the skin of the palms and soles, which is thicker, less pigmented, and less hairy). Thus, the disclosed methods are methods for inducing non-palmoplantar skin to develop a palmoplantar phenotype, and they include topically applying an effective amount of DKK1 to non-palmoplantar skin, which induces the skin changes. In some embodiments, the method is a method of treating a dermatological pathology, for instance a skin graft, a skin ulcer, a skin abrasion or avulsion/excision (such as one that leaves a volume defect), an injury or predisposition to injury caused by a repetitive impact or mechanical stress, age-related skin changes (for example photo-aged skin or thin skin), skin damage due to steroid treatment, uneven skin pigmentation, hyperpigmentation, post-inflammatory pigmentation, ephelides, fragrance dermatitis, vitiligo (for instance, where depigmentation is desired in a subject with widespread vitiligo), a pigmented birthmark (for example a café au lait spot), lentigos, or skin changes due to lichen simplex chronicus, melasma, porphyria cutanea tarda, Addison's disease, Peutz-Jeghers syndrome, acanthosis nigricans, hirsutism, congenital adrenal hyperplasia, polycystic ovarian syndrome, hypertrichosis, or anorexia nervosa.

Other embodiments are methods for increasing skin thickness. Some examples of these methods are carried out in vitro, whereas other examples of these methods include topically applying the DKK1 to an area of skin in need of thickening on a subject. In certain in vivo examples, the subject has a skin graft, an ulcer (for instance, a foot ulcer, particularly a diabetic foot ulcer), an abrasion, an injury caused by a repetitive impact or mechanical stress, age-related skin changes, or skin damage due to steroid treatment.

Further embodiments are methods for reducing skin pigmentation. Some examples of these methods are carried out in vitro, whereas in other examples of the methods the DKK1 is topically applied to an area of skin on a subject, for example a pigmented area where reduced pigmentation is desired. In certain examples, the subject has uneven skin pigmentation, hyperpigmentation, post-inflammatory pigmentation, ephelides, fragrance dermatitis, sun-damaged skin, vitiligo (for instance, where depigmentation is desired in a subject with widespread vitiligo), a pigmented birthmark (particularly those characterized by the deposition of excess melanin), lentigos, lichen simplex chronicus, melasma, Addison's disease, Peutz-Jeghers syndrome, porphyria cutanea tarda, or acanthosis nigricans.

Still other embodiments are methods for reducing hair growth. In some examples, DKK1 is applied topically to an area of skin on a subject where hair growth is to be suppressed, and in particular examples, the area of skin is on an upper or lower extremity or is axillary skin. In other examples, the subject has hirsutism, congenital adrenal hyperplasia, polycystic ovarian syndrome, hypertrichosis, porphyria cutanea tarda, or anorexia nervosa. In other embodiments the hair growth is to be reduced for cosmetic purposes.

Yet other embodiments are methods for treating or preventing melanoma. In some examples, the DKK1 is topically applied to an area of skin on a subject, such as an area that contains a hyperplastic or premalignant legion such as a nevus.

Also disclosed are pharmaceutical compositions for carrying out the methods described above. These compositions include an amount of DKK1 sufficient to induce non-palmoplantar skin to develop a palmoplantar phenotype and a carrier for topical administration. In some examples, the composition is a cream, an ointment, a lotion, or a tincture, for instance one including a liposome or a nanoformulation for enhanced delivery of DKK1. The compositions are for use in treating the conditions disclosed herein.

II. Abbreviations

| BCA: | bicinchoninic acid |
|---|---|
| BMP: | bone morphogenic protein |
| BSA: | bovine serum albumin |
| DKK1: | dickkopf 1 |
| Gadd: | growth arrest and DNA-damage-inducible gene |
| GSK: | glucose-synthase kinase |
| GSK3β: | glycogen synthase kinase 3β |
| HMGS: | Human Melanocyte Growth Supplement |
| HOX: | homeotic |
| HPS: | Hermansky-Pudlak syndrome |
| Krn: | Kremen |
| LDLR: | low-density lipoprotein receptor |
| LRP: | lipoprotein receptor-related protein |
| LRP6: | lipoprotein receptor-related protein 6 |
| MGM: | melanocyte growth medium |

-continued

| MITF: | microphthalmia-associated transcription factor |
|---|---|
| MLPH: | melanophilin |
| MRP: | mitochondrial ribosomal protein |
| PAR2: | proteinase-activated receptor-2 |
| PBS: | phosphate-buffered saline |
| PKC: | protein kinase C |
| rhDKK1: | human recombinant DKK1 |
| SDS: | sodium dodecyl sulfate |
| Shh: | Sonic hedgehog |
| STX5A: | syntaxin 5a |
| SV2B: | synaptic vesicle glycoprotein 2b |
| TNFRSF10A: | tumor necrosis factor receptor superfamily, member 10a |

III. Explanation of Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanation of terms is provided:

Acanthosis nigricans: a brown to black, poorly defined, velvety hyperpigmentation of the skin, usually present in the posterior and lateral folds of the neck, the axilla, groin, umbilicus, and other areas. Acanthosis nigricans occurs due to insulin spillover (from excessive production due to obesity or insulin insensitivity) into the skin which results in abnormal growth. The most common cause is insulin resistance, usually from type 2 diabetes mellitus. Other causes are familial, obesity, drug-induced, malignant (gastric cancer), and polycystic ovary syndrome.

Addison's disease: (also known as chronic adrenal insufficiency, or hypocortisolism), Addison's disease is a rare endocrine disorder which results in the body not producing sufficient amounts of certain adrenal hormones. Addison's disease refers specifically to primary adrenal insufficiency, in which the adrenal glands themselves malfunction; secondary adrenal insufficiency occurs when the anterior pituitary gland does not produce enough adrenocorticotropic hormone to adequately stimulate the adrenal glands.

The symptoms of Addison's disease are caused by the failure of the adrenal glands, seated above the kidneys, to produce enough of the hormone cortisol and, in some cases, the hormone aldosterone. Often the production of adrenaline is also diminished or eliminated. Addison's disease usually develops slowly (over several months), and symptoms may not present or be noticed until some stressful illness or situation occurs. Common symptoms are chronic fatigue that gradually worsens, muscle weakness, weight loss and loss of appetite, nausea, diarrhea, or vomiting, low blood pressure that falls further when standing (orthostatic hypotension), and areas of hyperpigmentation known as melasma suprarenale, which are caused by increases in pro-opiomelanocortin, hyponatraemia due to loss of production of the hormone aldosterone, hyperkalaemia due to loss of production of the hormone aldosterone, and axillary or pubic hypotrichosis.

Age-related skin changes: As people grow older, fine lines and wrinkles begin to develop. The skin loses its firmness and elasticity. Expression lines form on the face, and patches of discoloration and areas of dilated blood vessels appear. These changes occur gradually over time, and can first appear in the second and third decades of life. Such changes increase with advancing age, and generally people in their third, fourth, fifth, or subsequent decades of life experience at least some age-related skin changes.

In addition, photoaging describes aging caused by exposure to the sun's rays. Photoaging, as defined herein, is included in the category of age-related skin changes, and the amount of photoaging that develops depends on a person's skin color and their history of long-term or intense sun exposure. People with fair skin who have a history of sun exposure develop more signs of photoaging than those with dark skin. In the darkest skin, the signs of photoaging are usually limited to fine wrinkles and a mottled complexion.

Photoaging occurs over a period of years. With repeated exposure to the sun, the skin loses the ability to repair itself, and the damage accumulates. Repeated ultraviolet light exposure breaks down collagen and impairs the synthesis of new collagen and elastin, causing the skin to become loose, wrinkled, and leathery much earlier than would occur in the absence of sun exposure.

Animal: Living multi-cellular vertebrate organisms, a category that includes, for example, mammals and birds. The term mammal includes both human and non-human mammals. Similarly, the term "subject" includes both human and veterinary subjects. Therefore, the general term "subject" is understood to include all animals, including, but not limited to, humans, or veterinary subjects, such as other primates, dogs, cats, horses, and cows.

Anorexia nervosa: is a psychiatric diagnosis that describes an eating disorder characterized by low body weight and body image distortion. Individuals with anorexia often control body weight by voluntary starvation, purging, vomiting, excessive exercise, or other weight control measures, such as diet pills or diuretic drugs. It primarily affects young adolescent girls in the Western world and has one of the highest mortality rates of any psychiatric condition, with approximately 10% of people diagnosed with the condition eventually dying due to related factors. Anorexia nervosa is a complex condition, involving psychological, neurobiological, and sociological components.

People with anorexia typically have a disturbed electrolyte imbalance, low levels of essential hormones (including sex hormones), chronically increased cortisol levels, and osteoporosis develops as a result of anorexia in 38-50% of cases, as poor nutrition lead to the retarded growth of essential bone structure and low bone mineral density. Hypertrichosis is another common symptom of anorexia.

Congenital adrenal hyperplasia: refers to any of several autosomal recessive diseases resulting from defects in steps of the synthesis of cortisol from cholesterol by the adrenal glands. Most of these diseases involve excessive or deficient production of sex steroids and can alter or impair development of primary or secondary sex characteristics in affected infants, children, and adults.

Examples of problems caused by various forms of congenital adrenal hyperplasia include ambiguous genitalia, vomiting leading to dehydration and death in early infancy, early development of pubic hair, rapid growth in childhood, precocious puberty or failure of puberty to occur, excessive facial hair, virilization, hyperpigmentation, and/or menstrual irregularity in adolescence, and infertility due to anovulation.

Dermatological pathology: is an abnormal condition of the skin, including, but not limited to a condition causing uneven skin pigmentation, hyperpigmentation, unwanted hair growth, or thinning of the skin. Specific, nonlimiting examples of dermatological pathologies include a skin graft, an ulcer, an abrasion, an injury caused by a repetitive impact or mechanical stress, age-related skin changes, skin damage due to steroid treatment, uneven skin pigmentation, hyperpigmentation, post-inflammatory pigmentation, fragrance dermatitis, vitiligo, a pigmented birthmark, lentigos, or skin changes due to lichen simplex chronicus, melasma, porphyria cutanea tarda, Addison's disease, Peutz-Jeghers syndrome, acanthosis nigricans, hirsutism, congenital adrenal hyperplasia, polycystic ovarian syndrome, hypertrichosis, or anorexia nervosa.

DKK-1: a secreted antagonist of canonical Wnt signaling that interacts with Wnt receptor lipoprotein receptor-related protein 6 (LRP6) and with the transmembrane proteins Kremen (Krn) 1 and 2. DKK1 blocks canonical Wnt signaling by inducing endocytosis of the LRP6 complex without affecting the Wnt receptor Frizzled. DKK1 induces the formation of ectopic heads in *Xenopus laevis* in the presence of BMP inhibitors, and plays critical roles in modulating apoptosis during vertebrate limb development (especially inter-digit space formation) by interacting with BMP.

As used herein, the term DKK1 includes both human and non-human DKK1 proteins (for example, rat, mouse, and chicken DKK1), as well as functional DKK1 fragments. Specific, nonlimiting examples of Dkk-1 protein sequences are listed as GenBank Accession Nos. gi37183128, gi31542557, gi7110719, gi13124053, gi4545252, gi10281590, gi118092551, gi62858825, gi115313025, gi13124044, gi114630593, gi114630591, gi114630589, gi29504796, gi16306720, gi46394862, and gi5360731. Specific, non-limiting examples of DKK1 fragments can be found in U.S. Pat. No. 7,057,017. One of ordinary skill in the art will recognize that these DKK1 full-length proteins and DKK1 fragments are provided merely as examples; other proteins that fall into the described class will be recognized.

DNA (deoxyribonucleic acid): a long chain polymer which comprises the genetic material of most living organisms (some viruses have genes comprising ribonucleic acid (RNA)). The repeating units in DNA polymers are four different nucleotides, each of which comprises one of the four bases, adenine, guanine, cytosine and thymine bound to a deoxyribose sugar to which a phosphate group is attached. Triplets of nucleotides (referred to as codons) code for each amino acid in a polypeptide, or for a stop signal. The term codon is also used for the corresponding (and complementary) sequences of three nucleotides in the mRNA into which the DNA sequence is transcribed.

Unless otherwise specified, any reference to a DNA molecule is intended to include the reverse complement of that DNA molecule. Thus, a reference to the nucleic acid molecule that encodes DKK1 or a fragment thereof encompasses both the sense strand and its reverse complement. Thus, for instance, it is appropriate to generate probes or primers from the reverse complement sequence of the disclosed nucleic acid molecules.

Encode: a polynucleotide is said to "encode" a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

Ephelides: (freckles) are tanned macules found on the skin. They are usually multiple in number. With sun exposure, they become more apparent; therefore, in the winter months, they are often imperceptible. Although ephelides are predominantly benign, they may be seen in association with systemic disease.

Functional fragments and variants of a polypeptide: included are those fragments and variants that maintain at least one function of the parent polypeptide. It is recognized that the gene or cDNA encoding a polypeptide can be considerably mutated or truncated without materially altering one or more of the polypeptide's functions. Functional fragments and variants can be of varying length. For example, a fragment may consist of 10 or more, 25 or more, 50 or more, 75 or more, 100 or more, or 200 or more amino acid residues, so long as they maintain at least one function of the parent polypeptide.

Hirsutism: is defined as excessive and increased hair growth in locations where the occurrence of terminal hair normally is minimal or absent. It refers to a male pattern of body hair (androgenic hair) and it is therefore primarily of cosmetic and psychological concern. Hirsutism is a symptom rather than a disease and may be a sign of a more serious medical indication, especially if it develops well after puberty.

The cause of hirsutism can be either an increased level of androgens (male hormones) or an oversensitivity of hair follicles to androgens. Male hormones such as testosterone stimulate hair growth, increase size and intensify the pigmentation of hair. Other symptoms associated with a high level of male hormones include acne, irregular menstrual periods, deepening of the voice, and increased muscle mass.

Hyperpigmentation: the darkening of an area of skin or nails caused by increased melanin. Hyperpigmentation may be caused by sun damage, inflammation from acne, or other skin injuries, such as cuts, abrasions, burns, and puncture wounds, as well as the resulting scars. It is also associated with a number of diseases or conditions, including Addison's disease and other sources of adrenal insufficiency, in which hormones that stimulate melanin synthesis are frequently elevated, acanthosis nigricans, or hyperpigmentation of intertriginous areas associated with insulin resistance, or patchy hyperpigmentation often found in pregnant women, linea nigra, a hyperpigmented line found on the abdomen during pregnancy, post-inflammatory pigmentation, fragrance dermatitis, and Peutz-Jeghers syndrome, an autosomal dominant disorder characterized by hyperpigmented macules on the lips and oral mucosa and gastrointestinal polyps.

Hypertrichosis: refers to a condition of excessive body hair. It can be generalized, symmetrically affecting most of the torso and limbs, or localized, affecting an area of skin. It may be mild or severe. In most cases, the term is used to refer to an above-average amount of normal body hair that is unwanted and is an aspect of human variability. In medical practice, once generalized hypertrichosis has been distinguished from hirsutism, it is most often considered a variation of normal, primarily resulting from genetic factors.

Nearly all the skin of the human body (except palms of hands and soles of feet) is covered with hair. The density of the hairs (in hair follicles per square centimeter), thickness of the hairs, color of the hairs, speed of hair growth, and qualities such as kinkiness vary from one part of the body to another, and from one person to another. All of these features have strong genetic determinants, as demonstrated by the heritability of these qualities.

Hair can be categorized as scalp hair, vellus hair, or androgenic (terminal) hair. Scalp hair is the hair on the head. Vellus hair is the hair on the rest of the body which has not been stimulated and transformed by sex hormones. Androgenic hair is the hair that greatly increases in heaviness and rate of growth with puberty.

Most hypertrichosis is genetic, but a small number of unusual systemic disorders can sometimes increase vellus hair. Some drugs (for instance, diazoxide, diphenylhydantoin, and minoxidil) and toxins (for instance, mercury) can induce generalized hair growth as well. Unusual hypertrichosis can also be caused by untreated infection, or by malnutrition. For this reason, it is an occasional sign of anorexia nervosa.

Isolated: An "isolated" biological component (such as a nucleic acid molecule, protein or organelle) has been substantially separated or purified away from other biological components in the cell of the organism in which the component naturally occurs, for instance, other chromosomal and extrachromosomal DNA and RNA, proteins, and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Lichen simplex chronicus: a skin disorder characterized by chronic itching and scratching. The constant scratching causes thick, leathery, brownish skin. The disorder may begin with something that rubs, irritates, or scratches the skin, such as clothing. This causes the person to rub or scratch the affected area. Constant scratching causes the skin to thicken. The thickened skin itches, causing more scratching, causing more thickening. The skin may become leathery and brownish in the affected area. This disorder sometimes is associated with atopic dermatitis (eczema) or psoriasis. It is also associated with nervousness, anxiety, depression, and other psychological disorders.

Treatment is aimed at reducing itching and minimizing existing lesions because rubbing and scratching cause the condition. The itching and inflammation may be treated with a lotion or steroid cream applied to the affected area of the skin.

Melanoma: a malignant tumor of melanocytes and, less frequently, of retinal pigment epithelial cells (uveal melanoma). While it represents one of the rarer forms of skin cancer, melanoma underlies the majority of skin cancer-related deaths, and the sole effective cure is surgical resection of the primary tumor before it achieves a thickness of greater than 1 mm.

Melanoma of the skin accounts for 160,000 new cases worldwide each year, and is more frequent in Caucasian men. It is particularly common in Caucasian populations living in sunny climates. About 48,000 deaths worldwide due to malignant melanoma are registered annually.

The diagnosis of melanoma requires experience, as early stages may look identical to harmless moles or not have any color at all. Moles that are irregular in color or shape are suspicious of a malignant melanoma or a premalignant (or pre-melanoma) lesion, which is a lesion that is likely to progress to malignancy or melanoma over time. The treatment includes surgical removal of the tumor; adjuvant treatment; chemo- and immunotherapy, or radiation therapy.

The most common types of melanoma include: superficial spreading melanoma, nodular melanoma, acral lentiginous melanoma, and lentigo maligna. Any of these types may produce melanin (and be dark in color) or not (and be amelanotic—not dark). Similarly any subtype may show desmoplasia (dense fibrous reaction with neurotropism) which is a marker of aggressive behaviour and a tendency to local recurrence.

Melasma: (also known as chloasma or the mask of pregnancy when present in pregnant women), melasma is a tan or dark facial skin discoloration. Although it can affect anyone, melasma is particularly common in women, especially pregnant women and those who are taking oral contraceptives or hormone replacement therapy medications. It is also prevalent in men and women of Native American descent (on the forearms) and in men and women of German/Russian Jewish descent (on the face).

The symptoms of melasma include dark, irregular patches commonly found on the upper cheek, nose, lips, upper lip, and forehead. These patches often develop gradually over time. Melasma does not cause any other symptoms beyond the cosmetic discoloration. Melasma is thought to be the stimulation of melanocytes or pigment-producing cells by the female sex hormones estrogen and progesterone to produce more melanin pigments when the skin is exposed to sun. Women with a light brown skin type who are living in regions with intense sun exposure are particularly susceptible to developing this condition. Genetic predisposition is also a major factor in determining whether someone will develop melasma.

Palmoplantar skin: refers to the skin of the palms of the hands and the soles of the feet, whereas non-palmoplantar skin refers to the skin on the trunk and extremities, excluding the soles and palms. There are a number of topographical/anatomical/site-specific differences between human skin on the sole and the palm (also called palmoplantaris) and on the trunk (also called non-palmoplantaris) in terms of thickness and pigmentation. Not only is palmoplantar skin much thicker and less hairy than is skin in other regions of the body, but melanocytes in those areas are less dense and produce significantly less melanin pigment than non-palmoplantar skin. Fibroblasts derived from palmoplantar skin induce the expression of keratin 9, a marker for palmoplantar epidermis, in non-palmoplantar keratinocytes via mesenchymal-epithelial interactions. Further, non-palmoplantar epidermis (with no dermal components) adopts a palmoplantar phenotype when grafted on palmoplantar wounds. Finally, mRNA encoding dickkopf 1 (DKK1), an inhibitor of the canonical Wnt signaling pathway, is expressed at high levels in palmoplantar fibroblasts.

Peutz-Jeghers syndrome: an autosomal dominant disorder characterized by hyperpigmented macules on the lips and oral mucosa and gastrointestinal polyps. The risks associated with this syndrome include increased chance of developing cancer in multiple sites especially in the gastrointestinal tract. Other areas include the pancreas, liver, lungs, breast, ovaries, and testicles.

The average age of first diagnosis is 23, but the lesions can be identified at birth by an astute pediatrician. Prior to puberty, the mucocutaneous lesions can be found on the palms and soles. Often the first presentation is as a bowel obstruction from a large polyp or an intussusception, a telescoping of one loop of bowel into another segment.

Pharmaceutically acceptable carriers: The pharmaceutically acceptable carriers useful in this disclosure are conventional. Martin, *Remington's Pharmaceutical Sciences*, published by Mack Publishing Co., Easton, Pa., 19th Edition, 1995, describes compositions and formulations suitable for pharmaceutical delivery of, for instance DKK1.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for instance, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate. For topical pharmaceuticals, suitable carriers include any conventional carrier used to form a topical formulation, for instance a pharmaceutical foam, emulsion, microemulsion, cream, jelly, or liposome. Specific, non-limiting examples of suitable carriers for topical formulations include phosphatidylcholine, dimyristoyl phosphatidylcholine, dipalmitoyl phosphatidylcholine, dimyristoyl phosphatidylglycerol, dioleoyl phosphatidylethanolamine, phosphatidylcholine, glyceryl dilaurate/cholesterol/polyoxyethylene-10-stearyl ether, glyceryl distearate/cholesterol/polyoxyethylene-10-stearyl ether, and propylene glycol/ethanol/water.

Pigmented birthmark: is a blemish on the skin formed before birth, particularly one characterized by the excess deposition of melanin. Pigmented birthmarks are part of the group of pigmented skin lesions known as naevi. The cause of birthmarks is unknown, but may include cellular damage due to radiation or chemicals. Some types seem to run in families. One specific type of pigmented birthmark is a café au lait spot. The name café au lait is French for "coffee with milk" and refers to their light-brown color. While café au lait spots are usually not associated with any medical problems, having many (three or more) such spots is linked with neurofibromatosis and the rare McCune-Albright syndrome.

Polycystic ovarian syndrome: (also known clinically as Stein-Leventhal syndrome), is an endocrine disorder that affects 5-10% of women. It occurs amongst all races and nationalities, is the most common hormonal disorder among women of reproductive age, and is a leading cause of infertility. The principal features are lack of regular ovulation and excessive amounts or effects of androgenic hormones. The symptoms and severity of the syndrome vary greatly between women. While the causes are unknown, insulin resistance (often secondary to obesity) is heavily correlated with polycystic ovarian syndrome. Common symptoms include oligomenorrhea, amenorrhea, infertility, generally resulting from chronic anovulation (lack of ovulation), elevated serum levels of androgens, specifically testosterone, androstenedione, and dehydroepiandrosterone sulfate, causing hirsutism and occasionally masculinization, central obesity, androgenic alopecia, acne, oily skin, seborrhea, acanthosis nigricans (dark patches of skin, tan to dark brown or black), acrochordons (skin tags), prolonged periods of PMS-like symptoms (bloating, mood swings, pelvic pain, backaches), and sleep apnea.

Polypeptide: A polymer in which the monomers are amino acid residues that are joined together through amide bonds. When the amino acids are alpha-amino acids, either the L-optical isomer or the D-optical isomer can be used, the L-isomers being preferred. The term polypeptide or protein as used herein encompasses any amino acid sequence and includes modified sequences such as glycoproteins. The term polypeptide is specifically intended to cover naturally occurring proteins, as well as those that are recombinantly or synthetically produced.

The term polypeptide fragment refers to a portion of a polypeptide that exhibits at least one useful epitope. The phrase "functional fragments of a polypeptide" refers to all fragments of a polypeptide that retain an activity, or a measurable portion of an activity, of the polypeptide from which the fragment is derived. Fragments, for example, can vary in size from a polypeptide fragment as small as an epitope capable of binding an antibody molecule to a large polypeptide capable of participating in the characteristic induction or programming of phenotypic changes within a cell. An epitope is a region of a polypeptide capable of binding an immunoglobulin generated in response to contact with an antigen. Thus, smaller peptides containing the biological activity of DKK1, or conservative variants of DKK1, are thus included as being of use.

Porphyria cutanea tarda: is the most common type of porphyria. The disorder results from low levels of the enzyme responsible for the fifth step in heme production. Symptoms usually begin in adulthood and result from the skin becoming overly sensitive to sunlight. Areas of skin exposed to the sun develop severe blistering, scarring, changes in pigmentation, and increased hair growth. Exposed skin becomes fragile and is easily damaged. People with porphyria cutanea tarda also have increased iron levels in the liver. They face a higher risk of developing abnormal liver function and liver cancer. The signs and symptoms of this condition are triggered by nongenetic factors such as alcohol abuse, excess iron, certain hormones, and viral infections.

Preventing or treating a disease: "Preventing" a disease refers to inhibiting the full development of a disease, for example in a person who is at risk for a disease such as vitiligo, lichen simplex chronicus, melasma, porphyria cutanea tarda, Addison's disease, acanthosis nigricans, hirsutism, Peutz-Jeghers syndrome, congenital adrenal hyperplasia, polycystic ovarian syndrome, hypertrichosis, or melanoma. An example of a subject at risk for melanoma includes a person with a family history of skin cancer or a personal history of excessive sun exposure. "Treatment" refers to a therapeutic intervention that ameliorates a sign or symptom of a disease or pathological condition after it has begun to develop.

Protein: a biological molecule expressed by a gene and comprised of amino acids.

Purified: The term "purified" does not require absolute purity; rather, it is intended as a relative term. Thus, for example, a purified protein preparation is one in which the protein referred to is more pure than the protein in its natural environment within a cell or within a production reaction chamber (as appropriate).

Sequence identity: the similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are. Homologs or orthologs of a DKK1 protein, and the corresponding cDNA sequence, will possess a relatively high degree of sequence identity when aligned using standard methods. This homology will be more significant when the orthologous proteins or cDNAs are derived from species that are more closely related (for example, human and chimpanzee sequences), compared to species more distantly related (for example, human and *C. elegans* sequences).

Methods of alignment of sequences for comparison are well known in the art. Various programs and alignment algorithms are described in: Smith and Waterman *J. Mol. Biol.* 147(1):195-197, 1981; Needleman and Wunsch *J. Mol. Biol.* 48: 443-453, 1970; Pearson and Lipman *Proc. Natl. Acad. Sci. USA* 85: 2444-2448, 1988; Higgins and Sharp *Gene,* 73: 237-244, 1988; Higgins and Sharp *CABIOS* 5: 151-153, 1989; Corpet et al. *Nuc. Acids Res.* 16, 10881-10890, 1988; Huang et al. *Computer Appls. in the Biosciences* 8, 155-165, 1992; and Pearson et al. *Meth. Mol. Bio.* 24, 307-331, 1994. Furthermore, Altschul et al. (*J. Mol. Biol.* 215:403-410, 1990) present a detailed consideration of sequence alignment methods and homology calculations.

The NCBI Basic Local Alignment Search Tool (BLAST) (Altschul et al. *J. Mol. Biol.* 215: 403-410, 1990) is available from several sources, including the National Center for Biotechnology Information (NCBI, Bethesda, Md.) and on the Internet, for use in connection with the sequence analysis programs blastp, blastn, blastx, tblastn and tblastx. The Search Tool can be accessed at the NCBI website, together with a description of how to determine sequence identity using this program.

Nucleic acid sequences that do not show a high degree of identity can nevertheless encode similar amino acid sequences, due to the degeneracy of the genetic code. It is understood that changes in nucleic acid sequence can be made using this degeneracy to produce multiple nucleic acid molecules that all encode substantially the same protein.

Skin: includes the epidermis and dermis of an animal. Mammalian skin consists of two major, distinct layers. The outer layer of the skin is called the epidermis. The epidermis is comprised of the stratum corneum, the stratum granulosum, the stratum spinosum, and the stratum basale, with the stratum corneum being at the surface of the skin and the stratum basale being the deepest portion of the epidermis. The epidermis is between 50 µm and 0.2 mm thick, depending on its location on the body.

Beneath the epidermis is the dermis, which is significantly thicker than the epidermis. The dermis is primarily composed of collagen in the form of fibrous bundles. The collagenous bundles provide support for, inter alia, blood vessels, lymph capillaries, glands, nerve endings and immunologically active cells.

One of the major functions of the skin as an organ is to regulate the entry of substances into the body. The principal permeability barrier of the skin is provided by the stratum corneum, which is formed from many layers of cells in various states of differentiation. The spaces between cells in the stratum corneum is filled with different lipids arranged in lattice-like formations which provide seals to further enhance the skin's permeability barrier.

Skin damage due to steroid treatment: Local side effects of topical steroids include skin thinning (atrophy) and stretch marks (striae), easy bruising and tearing of the skin, perioral dermatitis (rash around the mouth), enlarged blood vessels (telangiectasia), susceptibility to skin infections, disguising infection (for instance, tinea incognito), and allergy to the steroid cream. The risk of these side effects depends on the strength of the steroid, the length of application, the site treated, and the nature of the skin problem.

Skin grafting: a type of medical grafting involving the transplantation of skin. The transplanted tissue is called a skin graft. Skin grafting is often used to treat extensive wounding or trauma, burns, ulcers, such as diabetic foot ulcers, areas of prior infection with extensive skin loss, and specific surgeries that may require skin grafts for healing to occur.

Subject: Living multi-cellular vertebrate organisms, a category that includes both human and non-human mammals. The methods disclosed herein have equal applications in medical and veterinary settings. Therefore, the general term "subject" is understood to include all animals, including, but not limited to, humans or veterinary subjects, such as other primates, dogs, cats, horses, and cows.

Therapeutically effective amount: A quantity of a specified compound (such as DKK1 or an equivalent thereof) required to achieve a desired effect in a subject being treated. For instance, this can be the amount necessary to treat or prevent a dermatological condition in a subject, or a dose sufficient to prevent advancement, or to cause regression of a disease, or which is capable of relieving symptoms caused by a disease, such as uneven skin pigmentation, hyperpigmentation, unwanted hair growth, or thin skin.

Topical administration: refers to the delivery of a composition, such as a protein, to an animal by contacting, directly or otherwise, a formulation that includes the protein to all or a portion of the skin (epidermis) of an animal. The term encompasses several routes of administration including, but not limited to, topical and transdermal administration. A common requirement for these modes of administration is penetration of the skin's permeability barrier and efficient delivery to the target tissue or stratum. In one embodiment, topical administration is used as a means to penetrate the epidermis and dermis and ultimately achieve systemic delivery of a protein. In another example, topical administration is used as a means to selectively deliver a protein to the epidermis or dermis of an animal, or to specific strata thereof.

Uneven skin pigmentation: refers to skin pigmentation that is more intense in some areas than in other. Uneven skin pigmentation is particularly bothersome to some individuals when it occurs on the face.

Vitiligo: also called leukoderma, is a chronic skin condition that causes loss of pigment, resulting in irregular pale patches of skin. The precise etiology of vitiligo is complex and not fully understood. There is some evidence suggesting it is caused by a combination of auto-immune, genetic, and environmental factors. The population incidence in the United States is between 1% and 2%.

Half of people with vitiligo develop patches of de-pigmented skin appearing on extremities before their 20s. The patches may grow or remain constant in size. Patches often occur symmetrically across both sides on the body. Occasionally small areas may repigment as they are recolonised by melanocytes. The location of vitiligo affected skin changes over time, with some patches re-pigmenting and others becoming affected.

In some cases, mild trauma to an area of skin seems to cause new patches—for example around the ankles (caused by friction with shoes or sneakers). Vitiligo may also be caused by stress that affects the immune system, leading the body to react and start eliminating skin pigment.

Methods for removing the white patches include corticosteroids, calcineurin inhibitors, ultraviolet light, and surgery, but they are not very effective. Other treatments include exposure to narrow band UV-B light, which seems to blur the edges of patches, and causes freckling in the affected areas. Immunomodulator creams such as Protopic and Elidel also cause repigmentation in some cases.

Alternatively, some people with vitiligo opt for chemical depigmentation, which typically uses 20% monobenzylether of hydroquinone. This process is irreversible and generally ends up with complete or mostly complete depigmentation.

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. Although methods and materials similar or equivalent to those described herein can be used in the practice or testing of the present disclosure, suitable methods and materials are described below. In case of conflict, the present specification, including terms, will control. In addition, the materials, methods, and examples are illustrative only and not intended to be limiting.

IV. Description of Several Specific Embodiments

A. The Effects of dickkopf 1 (DKK1) on Gene Expression and Wnt Signaling by Melanocytes Disclosed herein is the surprising discovery that topical application of DKK1 induces non-palmoplantar skin (for instance, skin of the trunk) to develop a palmoplantar phenotype. In particular, in addition to causing non-palmoplantar skin to thicken and become less hairy, topical DKK1 treatment reduced skin pigmentation. This is useful both for cosmetic reasons and for the treatment of a wide variety of conditions involving unwanted skin pigmentation, including uneven skin pigmentation, hyperpigmentation, post-inflammatory pigmentation, fragrance dermatitis, ephelides, sun-damaged skin, vitiligo (for instance, where depigmentation is desired in a subject with widespread vitiligo), pigmented pigmented birthmarks, moles, lentigos, lichen simplex chronicus, melasma, porphyria cutanea tarda, Addison's disease, Peutz-Jeghers syndrome, and acanthosis nigricans.

There are a number of topographical/anatomical/site-specific differences between human skin on the sole and the palm (also called palmoplantaris) and on the trunk (also called non-palmoplantaris) in terms of thickness and pigmentation (Yamaguchi et al., *J. Dermatol. Sci.* 40:1-9, 2005). Not only is palmoplantar skin much thicker than is skin in other regions of the body, but melanocytes in those areas are less dense and produce significantly less melanin pigment than non-palmoplantar skin. Fibroblasts derived from palmoplantar skin induce the expression of keratin 9, a marker for palmoplantar epidermis, in non-palmoplantar keratinocytes via mesenchymal-epithelial interactions (Yamaguchi et al., *J. Invest. Dermatol.* 112:483-488, 1999). Further, non-palmoplantar epidermis (with no dermal components) adopts a palmoplantar phenotype when grafted on palmoplantar wounds (Yamaguchi et al., *Arch. Dermatol.* 137:621-628, 2001; Yamaguchi and Yoshikawa, *J. Dermatol.* 28:521-534, 2001). Finally, mRNA encoding dickkopf 1 (DKK1), an inhibitor of the canonical Wnt signaling pathway, is expressed at high levels in palmoplantar fibroblasts (Yamaguchi et al., *J. Cell Biol.* 165:275-285, 2004).

Wnt signaling consists of a canonical pathway (which involves β-catenin and multiple protein complexes containing glycogen synthase kinase 3β (GSK3β), axin, adenomatous polyposis coli and Akt) and several non-canonical pathways (which involve calcium, protein kinase Cα (PKCα), c-Jun N-terminal kinase and focal adhesion kinase) (Kawano and Kypta, *J. Cell Sci.* 116:2627-2634, 2003; Zorn, *Curr Biol.* 11(15):R592-5, 2001). DKK1 is a secreted antagonist of canonical Wnt signaling that interacts with Wnt receptor lipoprotein receptor-related protein 6 (LRP6; Mao et al., *Nature* 411:321-325, 2001; Nusse, *Nature.* 17; 411(6835):255-6, 2001). DKK1 also interacts with the transmembrane proteins Kremen (Krn) 1 and 2 and blocks canonical Wnt signaling by inducing endocytosis of the LRP6 complex (Mao et al., *Nature;* 417(6889):664-7, 2002) without affecting the Wnt receptor Frizzled. DKK1 induces the formation of ectopic heads in *Xenopus laevis* in the presence of BMP inhibitors (Glinka et al., *Nature* 391:357-362, 1998) and plays critical roles in modulating apoptosis during vertebrate limb development (especially inter-digit space formation) by interacting with BMP (Grotewald & Ruther, 2002).

DKK genes (including DKK1, DKK2 and DKK3) are coordinately expressed in mesodermal lineages; transcripts of DKK1 are found in defined lineages, including limb buds, heart, urogenital ridge, tailbud, palate and craniofacial regions, whereas transcripts of DKK3 are restricted to the trunk mesenchyme (Monaghan et al., *Mech Dev.* 1999 September; 87(1-2):45-56, 1999).

HOX gene family members are transcription factors known to regulate patterning in the primary and secondary axes of developing embryos. HOX genes play critical roles in limb development (Dolle et al., *EMBO J.* 8(5):1507-15, 1989) and their collinear regulation is similar to that seen in the trunk: genes located in the middle of the HoxD complex are expressed in proximal areas of the limb bud while genes located in a more 5' direction have a more distal expression. HOX genes are also known to direct topographical/anatomical/site-specific differentiation of embryonic neurons in response to levels of fibroblast growth factors (Dasen et al., *Nature* 425:926-933, 2003; Liu et al., *Neuron.* 32(6):997-1012, 2001), bone morphogenetic protein (BMP: Dasen et al., *Nature* 425:926-933, 2003) and retinoic acid (Schubert et al., *Proc Natl Acad Sci USA* 101: 10320-10325, 2004).

B. Regulation of Skin Thickness

In addition to topical DKK1's effects on skin pigmentation, topical DKK1 also increases skin thickness in non-palmoplantar skin. This is useful in treating a variety of dermatological conditions, for instance skin grafts, skin ulcers, skin abrasions or avulsion/excisions (such as those that leave a volume defect), injuries or predispositions to injury caused by repetitive impacts or mechanical stress, age-related skin changes (for instance, thinning or wrinkled skin), or skin damage due to steroid treatment.

As described above, the epidermis in palmoplantar areas of the skin is thicker and less pigmented than in non-palmoplantar areas. Fibroblasts in palmoplantar dermis induce a thick epidermis and keratin 9 expression in non-palmoplantar keratinocytes through mesenchymal-epithelial interactions, whereas fibroblasts in non-palmoplantar dermis do not (Yamaguchi et al., *J. Invest. Dermatol.* 112:483-488, 1999).

Non-palmoplantar epidermis (excluding dermal components) can be grafted to treat palmoplantar skin defects (e.g. caused by diabetes mellitus (Yamaguchi et al., *Brit. J. Dermatol.* 151:1019-1028, 2004) and rheumatic diseases (Yamaguchi et al., *Brit. J. Dermatol.* 152:664-672, 2005)) because it can adopt a palmoplantar phenotype through mesenchymal-epithelial interactions (Yamaguchi et al., *Arch. Dermatol.* 137:621-628, 2001; Yamaguchi and Yoshikawa, *J. Dermatol.* 28:521-534, 2001).

DKK1, which interacts with the Wnt receptor lipoprotein receptor-related protein 6 (LRP6; Mao et al., *Nature* 411:321-325, 2001), is a secreted antagonist of the canonical Wnt signaling pathway, which involves β-catenin and multiple protein complexes containing glycogen synthase kinase 3β (GSK3β), axin, adenomatous polyposis coli (APC) and Akt (Kawano & Kypta, *J. Cell Sci.* 116:2627-2634, 2003).

As described above, HOX gene family members are transcription factors regulating patterning in the primary and secondary axes of developing embryos which also control digit number and morphogenesis (Zakany et al., *Science* 304: 1669-1672, 2004). The collinear regulation of HOX genes during limb development is similar to that seen in the trunk: genes located in the middle of the HoxD complex (HoxD8) are expressed in proximal areas of the limb bud whereas genes located upstream have a more distal expression (HoxD12; Kmita et al., *Nature* 420:145-150, 2002). HOX genes are also known to direct topographical/site-specific differentiation of embryonic neurons in response to growth factors, especially those secreted by fibroblasts (Dasen et al., *Nature* 425:926-933, 2003).

C. DKK1 Sequence Variants

There are a number of variant DKK1 sequences that can be used in lieu of or in conjunction with known DKK1 sequences. A number of specific DKK1 amino acid sequences are known. For instance, the term "DKK1" can refer to any DKK1 amino acid sequence, such as GenBank™ Accession Nos. gi37183128, gi31542557, gi7110719, gi13124053, gi4545252, gi10281590, gi118092551, gi62858825, gi115313025, gi13124044, gi114630593, gi114630591, gi114630589, gi29504796, gi16306720, gi46394862, and gi5360731, all of which are specific, non-limiting examples. In addition to known DKK1 sequences, the creation of variants of these sequences is now enabled. Other variant DKK1 sequences can be found in U.S. Pat. No. 7,057,017, which is incorporated by reference in its entirety.

Variant DKK1 proteins include proteins that differ in amino acid sequence from known DKK1 sequences, but that share at least 60% amino acid sequence identity with a known DKK1 protein. Other variants will share at least 75%, at least 80%, at least 85%, at least 90%, at least 95%, or at least 98% amino acid sequence identity. Manipulation of a DKK1 nucleotide sequence using standard procedures, including for instance site-directed mutagenesis or PCR, can be used to produce such variants. The simplest modifications involve the substitution of one or more amino acids for amino acids having similar biochemical properties. These conservative substitutions are likely to have minimal impact on the activity of the resultant protein. Table 1 shows amino acids that may be substituted for an original amino acid in a protein, and which are regarded as conservative substitutions.

TABLE 1

| Original Residue | Conservative Substitutions |
| --- | --- |
| Ala | ser |
| Arg | lys |
| Asn | gln; his |
| Asp | glu |
| Cys | ser |
| Gln | asn |
| Glu | asp |
| Gly | pro |
| His | asn; gln |
| Ile | leu; val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

More substantial changes in enzymatic function or other protein features may be obtained by selecting amino acid substitutions that are less conservative than those listed in Table 1. Such changes include changing residues that differ more significantly in their effect on maintaining polypeptide backbone structure (for example, sheet or helical conformation) near the substitution, charge or hydrophobicity of the molecule at the target site, or bulk of a specific side chain. The following substitutions are generally expected to produce the greatest changes in protein properties: (a) a hydrophilic residue (for example, seryl or threonyl) is substituted for (or by) a hydrophobic residue (for example, leucyl, isoleucyl, phenylalanyl, valyl or alanyl); (b) a cysteine or proline is substituted for (or by) any other residue; (c) a residue having an electropositive side chain (for example, lysyl, arginyl, or histadyl) is substituted for (or by) an electronegative residue (for example, glutamyl or aspartyl); or (d) a residue having a bulky side chain (for example, phenylalanine) is substituted for (or by) one lacking a side chain (for example, glycine).

Variant DKK1-encoding sequences may be produced by standard DNA mutagenesis techniques, for example, M13 primer mutagenesis. Details of these techniques are provided in Sambrook et al. (*In Molecular Cloning: A Laboratory Manual*, CSHL, New York, 1989), Ch. 15. By the use of such techniques, variants may be created that differ in minor ways from known DKK1 sequences. DNA molecules and nucleotide sequences that are derivatives of known DKK1 sequences, and which differ from those disclosed by the deletion, addition, or substitution of nucleotides while still encoding a protein that has at least 60% sequence identity with known DKK1 sequences are comprehended by this disclosure. Also comprehended are more closely related nucleic acid molecules that share at least 70%, at least 75%, at least 80%, at least 85%, at least 90%, at least 95%, or at least 98% nucleotide sequence identity with known DKK1 sequences. In their most simple form, such variants may differ from the disclosed sequences by alteration of the coding region to fit the codon usage bias of the particular organism into which the molecule is to be introduced.

Alternatively, the coding region may be altered by taking advantage of the degeneracy of the genetic code to alter the coding sequence such that, while the nucleotide sequence is substantially altered, it nevertheless encodes a protein having an amino acid sequence substantially similar to known DKK1 protein sequences. For example, because of the degeneracy of the genetic code, four nucleotide codon triplets—(GCT, GCG, GCC and GCA) code for alanine. The coding sequence of any specific alanine residue within a known DKK1 protein, therefore, could be changed to any of these alternative codons without affecting the amino acid composition or characteristics of the encoded protein. Based upon the degeneracy of the genetic code, variant DNA molecules may be derived from the cDNA and gene sequences disclosed herein using standard DNA mutagenesis techniques as described above, or by synthesis of DNA sequences. Thus, this disclosure also encompasses nucleic acid sequences that encode a known DKK1 protein, but which vary from the known nucleic acid sequences by virtue of the degeneracy of the genetic code.

D. Functional Fragments and Variants of DKK1

Also included in the term "DKK1" are those DKK1 fragments and variants that maintain at least one function of the parent polypeptide, for instance the ability to increase skin thickness, decrease skin pigmentation, or decrease hair growth. It is recognized that the gene or cDNA encoding a polypeptide can be considerably mutated without materially altering one or more of the polypeptide's functions. First, the genetic code is well known to be degenerate, and thus different codons encode the same amino acids. Second, even where an amino acid substitution is introduced, the mutation can be conservative and have no material impact on the essential functions of a protein (see Stryer, Biochemistry 4th Ed., (c) W. Freeman & Co., New York, N.Y., 1995). Third, part of a polypeptide chain can be deleted without impairing or eliminating all of its functions. For example, sequence variants in a protein, such as a 5' or 3' variant, may retain the full function of an entire protein. Fourth, insertions or additions can be made in the polypeptide chain for example, adding epitope tags, without impairing or eliminating its functions (Ausubel et al., Current Protocols in Molecular Biology, Greene Publ. Assoc. and Wiley-Intersciences, 1998).

Other modifications that can be made without materially impairing one or more functions of a polypeptide include, for example, in vivo or in vitro chemical and biochemical modifications or the incorporation of unusual amino acids. Such modifications include, for example, acetylation, carboxylation, phosphorylation, glycosylation, ubiquination, sumoylation, labeling, for example, with radionucleides, and various enzymatic modifications, as will be readily appreciated by those well skilled in the art. A variety of methods for labeling polypeptides and labels useful for such purposes are well known in the art, and include radioactive isotopes such as $^{32}P$, ligands that bind to or are bound by labeled specific binding partners (for example, antibodies), fluorophores, chemiluminescent agents, enzymes, and antiligands. Functional DKK1 fragments and variants can be of varying length. For example, a fragment may consist of 10 or more, 25 or more, 50 or more, 75 or more, 100 or more, or 200 or more amino acid residues. Specific, nonlimiting examples of DKK1 fragments are found in U.S. Pat. No. 7,057,017, which is incorporated by reference in its entirety.

E. Routes of Administration of DKK1

The permeability barrier provided by the skin is such that it is largely impermeable to molecules having molecular weight greater than about 750 Da. For larger molecules to cross the skin's permeability barrier, methods other than normal osmosis must be used. These methods are used in some embodiments for the delivery of DKK1 through the skin's permeability barrier to the epidermis and the dermis.

Several factors determine the permeability of the skin to administered agents. These factors include the characteristics of the treated skin, the characteristics of the delivery agent, interactions between both the drug and delivery agent and the drug and skin, the dosage of the drug applied, the form of treatment, and the post-treatment regimen. To selectively target the epidermis and dermis, it is sometimes possible to formulate a composition that comprises one or more penetration enhancers that will enable penetration of the drug to a preselected stratum.

One method for delivering biologically active substances to the skin is topical administration. Topical administration can be used as the route of administration when local delivery of a drug is desired at, or immediately adjacent to, the point of application of the drug composition or formulation. Three general types of topical routes of administration include administration of a drug composition to mucous membranes, skin or eyes.

Transdermal drug delivery is a valuable route for the administration of lipid soluble therapeutics. The dermis is more permeable than the epidermis and therefore absorption is much more rapid through abraded, burned or denuded skin. Inflammation and other physiologic conditions that increase blood flow to the skin also enhance transdermal adsorption. Absorption via this route may be enhanced by the use of an oily vehicle (inunction) or through the use of one or more penetration enhancers. Other effective ways to deliver drugs via the transdermal route include hydration of the skin and the use of controlled release topical patches. The transdermal route provides an effective means to deliver a drug for either systemic or local therapy.

In addition, iontophoresis (transfer of ionic solutes through biological membranes under the influence of an electric field; see, for instance, Lee et al., *Critical Reviews in Therapeutic Drug Carrier Systems,* 1991, p. 163), phonophoresis or sonophoresis (use of ultrasound to enhance the absorption of various therapeutic agents across biological membranes, notably the skin and the cornea; see, for instance, Lee et al., p. 166), and optimization of vehicle characteristics relative to dose deposition and retention at the site of administration (see, for instance, Lee et al., p. 168) are useful methods for enhancing the transport of drugs across mucosal sites in accordance with compositions and methods of the present invention.

In some embodiments, DKK1 is administered topically with one or more penetration enhancers, for example those described below in section F. The DKK1 is generally applied in the form of a cream, lotion, ointment, tincture, liposome, emulsion, nanoformulation, microsponge formulation, or other formulation, as described below in section F, and according to an administration protocol, as outlined in section G.

F. Pharmaceutical Compositions for Topical Administration

Pharmaceutical compositions that contain DKK1 can include, but are not limited to, solutions, emulsions, and liposome-containing formulations. These compositions are formulated for topical administration, and are generated from a variety of components that include, but are not limited to, preformed liquids, self-emulsifying solids and self-emulsifying semisolids. DKK1-containing pharmaceutical compositions, which in some examples are presented in unit dosage form, are prepared according to conventional techniques well known in the pharmaceutical industry. Such techniques include the step of bringing into association the active ingredients with one or more pharmaceutical carriers or excipients, which in some examples are liquid carriers or finely divided solid carriers.

DKK1-containing compositions are, in some embodiments, formulated as suspensions in aqueous, non-aqueous or mixed media. In some embodiments, aqueous suspensions further contain substances which increase the viscosity of the suspension, including, for example, sodium carboxymethylcellulose, sorbitol and/or dextran. Such a suspension also may contain stabilizers.

In certain embodiments, a DKK1-containing pharmaceutical composition is formulated as a foam. Pharmaceutical foams include formulations such as, but not limited to, emulsions, microemulsions, creams, jellies, and liposomes. While similar in nature, these formulations vary in the components and the consistency of the final product. Also useful are nanoformulations and microsponge formulations (see, for instance, Grimes, *Cutis*. 2004 December; 74(6):362-8.). The preparation of such compositions and formulations is generally known to those skilled in the pharmaceutical and formulation arts, and can be applied to the formulation of the compositions disclosed herein.

1. Emulsions

The DKK1-containing compositions disclosed herein can be prepared and formulated as emulsions. Emulsions are typically heterogeneous systems of one liquid dispersed in another in the form of droplets, and those droplets usually exceed 0.1 um in diameter (see Idson in *"Pharmaceutical Dosage Forms,"* Lieberman, Rieger and Banker (Eds.), 1988, volume 1, p. 199; Rosoff in *"Pharmaceutical Dosage Forms,"* Lieberman, Rieger and Banker (Eds.), 1988, volume 1, p. 245; Block in *"Pharmaceutical Dosage Forms,"* Lieberman, Rieger and Banker (Eds.), 1988, volume 2, p. 335; and Higuchi et al., in *"Remington's Pharmaceutical Sciences,"* Mack Publishing Co., Easton, Pa., 1985, p. 301). Emulsions are often biphasic systems comprising two immiscible liquid phases intimately mixed and dispersed with each other.

In general, emulsions may be either water in oil or oil in water. When an aqueous phase is finely divided into and dispersed as minute droplets into a bulk oily phase, the resulting composition is called a water in oil emulsion. Alternatively, when an oily phase is finely divided into and dispersed as minute droplets into a bulk aqueous phase the resulting composition is called an oil in water emulsion. Emulsions may contain additional components in addition to the dispersed phases and the active drug, which may be present as a solution in either the aqueous phase, the oily phase, or as a separate phase itself.

Pharmaceutical excipients such as emulsifiers, stabilizers, dyes, and anti-oxidants may also be present in emulsions. Pharmaceutical emulsions may also be multiple emulsions that are comprised of more than two phases such as, for example, oil in water in oil and water in oil in water emulsions. Multiple emulsions in which individual oil droplets of an oil in water emulsion enclose small water droplets constitute a water in oil in water emulsion. Likewise, a system of oil droplets enclosed in globules of water stabilized in an oily continuous provides an oil in water in oil emulsion.

Emulsions generally are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion can be a semisolid or a solid, as is the case of emulsion-style ointment bases and creams. Other means of stabilizing emulsions entail the use of emulsifiers that can be incorporated into either phase of the emulsion. Emulsifiers may broadly be classified into four categories: synthetic surfactants, naturally-occurring emulsifiers, absorption bases, and finely-dispersed solids (see, for instance, Idson, 1988, volume 1, p. 199).

Synthetic surfactants, also known as surface active agents, have found wide applicability in the formulation of emulsions (see, for instance, Rieger, 1988, volume 1, p. 285; Idson, 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance, and is a valuable tool in categorizing and selecting surfactants in the preparation of formulations. Surfactants are classified into different classes based on the nature of the hydrophilic group: nonionic, anionic, cationic and amphoteric (Rieger, 1988, volume 1, p. 285).

Specific, non-limiting examples of naturally-occurring emulsifiers used in emulsion formulations include lanolin, beeswax, phosphatides, lecithin and acacia. Specific, non-limiting examples of absorption bases that possess hydrophilic properties such that they can soak up water to form water in oil emulsions, yet retain their semisolid consistencies, include anhydrous lanolin and hydrophilic petrolatum. Finely divided solids also can be used as emulsifiers, especially in combination with surfactants and in viscous preparations. Specific, non-limiting examples of these include polar inorganic solids, such as heavy metal hydroxides, non-swelling clays such as bentonite, attapulgite, hectorite, kaolin, montmorillonite, colloidal aluminum silicate, and colloidal magnesium aluminum silicate, and pigments and non-polar solids such as carbon or glyceryl tristearate.

A large variety of non-emulsifying materials also can be included in emulsion formulations, and contribute to the properties of emulsions. These include fats, oils, waxes, fatty acids, fatty alcohols, fatty esters, humectants, hydrophilic colloids, preservatives and antioxidants (Block, 1988, volume 1, p. 335; Idson, 1988, volume 1, p. 199). Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylc cellulose and carboxypropyl cellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols, and phosphatides that may readily support the growth of microbes, these formulations often incorporate preservatives. Commonly used preservatives included in emulsion formulations include methylparaben, propylparaben, quaternary ammonium salts, benzalkonium chloride, esters of p-hydroxybenzoic acid, boric acid and phenoxyethanol. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

In some embodiments, DKK1-containing compositions are formulated as microemulsions. A microemulsion is a system of water, oil, and amphiphile, which is a single optically isotropic and thermodynamically stable liquid solution (see, for instance, Rosoff, 1988, volume 1, p. 245). Typically, microemulsions are systems that are prepared by first dispersing an oil in an aqueous surfactant solution and then adding a sufficient amount of a fourth component, generally an intermediate chain-length alcohol to form a transparent system. Thus, microemulsions generally are thermodynamically stable, isotropically clear dispersions of two immiscible liquids that are stabilized by interfacial films of surface-active molecules (Leung & Shah, in: *Controlled Release of Drugs: Polymers and Aggregate Systems*, Rosoff, M., Ed., 1989, VCH Publishers, New York, pages 185-215).

Microemulsions commonly are prepared via a combination of three to five components that include oil, water, surfactant, cosurfactant, and electrolyte. Whether the microemulsion is of the water-in-oil or an oil-in-water type is dependent on the properties of the oil and surfactant used and on the structure and geometric packing of the polar heads and hydrocarbon tails of the surfactant molecules (Schott, in *"Remington's Pharmaceutical Sciences,"* Mack Publishing Co., Easton, Pa., 1985, p. 271). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), and decaglycerol decaoleate (DAO750), either alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants, and alcohol-free self-emulsifying microemulsion systems are known in the art. The aqueous phase typically includes, but is not limited to, water, an aqueous solution of the drug, glycerol, PEG300, PEG400, polyglycerols, propylene glycols, and derivatives of ethylene glycol. The oil phase often includes, but is not limited to, materials such as Captex 300, Captex 355, Capmul MCM, fatty acid esters, medium chain (C8-C12) mono, di, and triglycerides, polyoxyethylated glyceryl fatty acid esters, fatty alcohols, polyglycolized glycerides, saturated polyglycolized C8-C10 glycerides, vegetable oils, and silicone oil.

Microemulsions are of particular interest from the standpoint of drug solubilization and the enhanced absorption of drugs. Lipid based microemulsions enhance the oral bioavailability of drugs, including peptides (Constantinides et al., *Pharmaceutical Research*, 1994, 11, 1385; Ritschel, *Meth. Find. Exp. Clin. Pharmacol.*, 1993, 13, 205). Microemulsions afford advantages of improved drug solubilization, protection of drug from enzymatic hydrolysis, enhancement of drug absorption due to surfactant-induced alterations in membrane fluidity and permeability, ease of preparation, improved clinical potency, and decreased toxicity (Constantinides et al., 1994, 11, 1385; Ho et al., *J. Pharm. Sci.*, 1996, 85, 138).

Often, microemulsions form spontaneously when their components are brought together at ambient temperature. This may be particularly advantageous when formulating thermolabile drugs or peptides. Microemulsions also are effective for transdermal delivery of active components in both cosmetic and pharmaceutical applications. DKK1-containing microemulsion compositions and formulations will facilitate the increased absorption of DKK1 from the skin.

The microemulsions disclosed herein also may contain additional components and additives such as sorbitan monostearate (Grill 3), Labrasol, and penetration enhancers to improve the properties of the formulation and to enhance the absorption of DKK1. Penetration enhancers used in microemulsions can be classified as belonging to one of five broad categories: surfactants, fatty acids, bile salts, chelating agents, and non-chelating non-surfactants, as discussed above.

2. Liposomes

There are many organized surfactant structures besides microemulsions that are useful for the formulation of drugs. These include monolayers, micelles, bilayers and vesicles. Vesicles, such as liposomes, have particular advantages because of their specificity and the duration of action they offer. As used herein, the term "liposome" refers to a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly transformable and able to pass through such fine pores. Liposomes are useful for the transfer and delivery of active ingredients to the site of action. Because the liposomal membrane is structurally similar to biological membranes, when liposomes are applied to a tissue, the liposomes start to merge with the cellular membranes. As the merging of the liposome and cell progresses, the liposomal contents are emptied into the cell where the active agent may act. For topical administration, liposomes present several advantages over other formulations, including reduced side-effects related to high systemic absorption of the administered drug, increased accumulation of the administered drug at the desired target, and the ability to administer a wide variety of drugs, both hydrophilic and hydrophobic, into the skin. In addition, liposomes can be used to deliver agents such as high-molecular weight proteins into the skin.

Liposomes fall into two broad classes. Cationic liposomes are positively charged liposomes that interact with negatively charged compositions to form a stable complex. The positively charged composition/liposome complex binds to the negatively charged cell surface and is internalized in an endosome. Due to the acidic pH within the endosome, the liposomes are ruptured, releasing their contents into the cell's cytoplasm.

Liposomes that are pH-sensitive or negatively charged entrap negatively charged compositions rather than complex with them. Since both the composition and the lipid are similarly charged, repulsion rather than complex formation occurs. Nevertheless, some of the negatively charged composition is entrapped within the aqueous interior of these liposomes.

One major type of liposomal composition includes phospholipids other than naturally-derived phosphatidylcholine. Neutral liposome compositions, for example, can be formed from dimyristoyl phosphatidylcholine or dipalmitoyl phosphatidylcholine. Anionic liposome compositions generally are formed from dimyristoyl phosphatidylglycerol, while anionic fusogenic liposomes are formed primarily from dioleoyl phosphatidylethanolamine. Another type of liposomal composition is formed from phosphatidylcholine such as, for example, soybean phosphatidylcholine, and egg phosphatidylcholine. Another type is formed from mixtures of phospholipid and/or phosphatidylcholine and/or cholesterol.

Non-ionic liposomal systems also are useful for the delivery of drugs to the skin, in particular systems comprising non-ionic surfactant and cholesterol. Non-ionic liposomal formulations comprising Novasome I (glyceryl dilaurate/cholesterol/polyoxyethylene-10-stearyl ether) and Novasome II (glyceryl distearate/cholesterol/polyoxyethylene-10-stearyl ether) are particularly effective in facilitating the deposition of various compositions into different layers of the skin.

Transfersomes are yet another type of liposomes, and are highly deformable lipid aggregates that are attractive candidates for drug delivery vehicles. Transfersomes are lipid droplets which are so highly deformable that they are easily able to penetrate through pores which are smaller than the droplet. Transfersomes are adaptable to the environment in which they are used, for instance, they are self-optimizing (adaptive to the shape of pores in the skin), self-repairing, frequently reach their targets without fragmenting, and often self-loading. Surface edge-activators, usually surfactants, are added to a standard liposomal composition to make transfersomes.

Surfactants find wide application in formulations such as emulsions (including microemulsions) and liposomes. The most common way of classifying and ranking the properties of the many different types of surfactants, both natural and synthetic, is by the use of the hydrophile/lipophile balance. The nature of the hydrophilic group (also known as the 'head') provides the most useful means for categorizing the different surfactants used in formulations.

If the surfactant molecule is not ionized, it is classified as a nonionic surfactant. Nonionic surfactants find wide application in pharmaceutical and cosmetic products and are usable over a wide range of pH values. In general, their hydrophile/lipophile balance values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

Liposomal delivery systems are discussed at greater length in U.S. Pat. No. 6,841,539.

3. Penetration Enhancers

In some embodiments, various penetration enhancers are used to effect the efficient delivery of DKK1 to the skin. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories: surfactants, fatty acids, bile salts, chelating agents, and non-chelating non-surfactants (Lee et al., *Crit. Rev. Ther. Drug Carrier Systems,* 1991, p. 92). Each of these classes is described below in greater detail.

Surfactants are chemical entities that, when dissolved in an aqueous solution, reduce the surface tension of the solution or the interfacial tension between the aqueous solution and another liquid, with the result that absorption of proteins through the mucosa is enhanced. In addition to bile salts and fatty acids, these penetration enhancers include, for example, sodium lauryl sulfate, polyoxyethylene-9-lauryl ether, and polyoxyethylene-20-cetyl ether, and perfluorhemical emulsions, such as FC-43.

Various fatty acids and their derivatives that act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, C1-10 alkyl esters thereof (for instance, methyl, isopropyl and t-butyl), and mono- and di-glycerides thereof (for instance, oleate, laurate, caprate, myristate, palmitate, stearate, and linoleate).

Various natural bile salts and their synthetic derivatives act as penetration enhancers, as well. The term "bile salts" includes any of the naturally occurring components of bile as well as any of their synthetic derivatives. Specific, non-limiting examples of bile salts include cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydrofusidate (STDHF), sodium glycodihydrofusidate, and polyoxyethylene-9-lauryl ether (POE).

Chelating agents are compounds that remove metallic ions from solution by forming complexes therewith, with the result that absorption of proteins through the mucosa is enhanced. Specific, non-limiting examples of chelating agents include disodium ethylenediaminetetraacetate, citric acid, salicylates (for instance, sodium salicylate, 5-methoxysalicylate and homovanilate), N-acyl derivatives of collagen, laureth-9 and N-amino acyl derivatives of beta-diketones (enamines).

Non-chelating non-surfactant penetration enhancing compounds are compounds that demonstrate insignificant activity as chelating agents or as surfactants, but that nonetheless enhance absorption of proteins through the skin. This class of penetration enhancers includes, for example, unsaturated cyclic ureas, 1-alkyl- and 1-alkenylazacyclo-alkanone derivatives, and non-steroidal anti-inflammatory agents such as diclofenac sodium, indomethacin and phenylbutazone.

Agents that enhance uptake of proteins at the cellular level also may be added to the DKK1 compositions. For example, cationic lipids, such as lipofectin (U.S. Pat. No. 5,705,188), cationic glycerol derivatives, and polycationic molecules, such as polylysine (WO 97/30731), are also known to enhance the cellular uptake of proteins.

Other agents may be utilized to enhance the penetration of the administered DKK1 protein, including glycols such as ethylene glycol and propylene glycol, pyrrols such as 2-pyrrol, azones, and terpenes such as limonene and menthone. Dimethyl sulfoxide (DMSO) is another common penetrant that can be used to promote topical absorption and uptake.

4. Excipients

A pharmaceutical carrier or excipient is a pharmaceutically acceptable solvent, suspending agent, or any other pharmacologically inert vehicle for delivering one or more proteins to an animal. The excipient can be liquid or solid and is selected with the planned manner of administration in mind so as to provide for the desired bulk, consistency, etc., when combined with a nucleic acid and the other components of a given pharmaceutical composition. Typical pharmaceutical carriers include, but are not limited to, binding agents (for example, pregelatinised maize starch, polyvinylpyrrolidone, or hydroxypropyl methylcellulose); fillers (for example, lactose and other sugars, microcrystalline cellulose, pectin, gelatin, calcium sulfate, ethyl cellulose, polyacrylates or calcium hydrogen phosphate); lubricants (for example, magnesium stearate, talc, silica, colloidal silicon dioxide, stearic acid, metallic stearates, hydrogenated vegetable oils, corn starch, polyethylene glycols, sodium benzoate, sodium acetate); disintegrants (for example, starch, sodium starch glycolate); and wetting agents (for example, sodium lauryl sulphate).

Formulations for topical administration of proteins may include sterile and non-sterile aqueous solutions, non-aqueous solutions in common solvents such as alcohols, or solutions of the proteins in liquid or solid oil bases. The solutions also may contain buffers, diluents and other suitable additives. Other pharmaceutically acceptable organic or inorganic excipients suitable for non-parenteral administration that do not deleteriously react with proteins can be used. Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

5. Other Components

DKK1 compositions additionally may contain other adjunct components conventionally found in pharmaceutical compositions, at their art-established usage levels. Thus, for example, the compositions may contain additional, compatible, pharmaceutically-active materials such as, for example, antipruritics, astringents, local anesthetics, or anti-inflammatory agents, or may contain additional materials useful in physically formulating various dosage forms of the composition, such as dyes, flavoring agents, preservatives, antioxidants, opacifiers, thickening agents, and stabilizers. However, such materials, when added, should not unduly interfere with the biological activities of the components of the compositions. The formulations can be sterilized and, if desired, mixed with auxiliary agents, for example lubricants, preservatives, stabilizers, wetting agents, emulsifiers, salts for influencing osmotic pressure, buffers, colorings, flavorings, and/or aromatic substances and the like that do not deleteriously interact with the DKK1 proteins of the formulation.

In addition, aqueous suspensions may contain substances that increase the viscosity of the suspension including, for example, hydroxypropyl methylcellulose, sodium carboxymethylcellulose, sorbitol, and/or dextran. The suspension may also contain stabilizers.

G. Treatment Regimens

The administration of therapeutic or pharmaceutical compositions that include the DKK1 proteins is described herein. In general, a subject in need of therapy or prophylaxis is administered (topically) a composition comprising a DKK1 protein, commonly in a pharmaceutically acceptable carrier, in doses ranging from 0.01 µg to 10 g per kg of body weight depending on the age of the patient and the severity of the disorder or disease state being treated. Dosing is dependent on severity and responsiveness of the disease state to be treated, with the course of treatment lasting from several days to several months, or until a cure is effected or a diminution or prevention of the disease state is achieved. Optimal dosing schedules can be calculated from the subject's response to treatment, and persons of ordinary skill can easily determine optimum dosages, dosing methodologies and repetition rates.

The term "treatment regimen" is meant to encompass therapeutic, palliative and prophylactic modalities of topical administration of one or more DKK1 proteins. A particular treatment regimen may last for a period of time that will vary depending upon the nature of the particular disease or disorder, its severity and the overall condition of the patient, and may extend from multiple daily applications to twice daily applications, daily applications, or applications every two, three, four, seven, or more days, for instance once each month or once every year. Following treatment, the subject is monitored for changes in his/her condition and for alleviation of the symptoms of the disorder or disease state. The dosage of the DKK1 composition may either be increased in the event the subject does not respond significantly to current dosage levels, or the dose may be decreased if an alleviation of the symptoms of the disorder or disease state is observed.

Following successful treatment, it may be desirable to have the patient undergo maintenance therapy to prevent the recurrence of the disease state, wherein the bioactive agent is administered in maintenance doses, ranging from 0.01 µg to 10 g per kg of body weight, with a frequency of from once or more daily to once every year.

Prophylactic treatment for high risk individuals is also disclosed herein. As used herein, the term "high risk individual" is meant to refer to an individual for whom it has been determined, for instance via individual or family history or genetic testing, that there is a significantly higher than normal probability of being susceptible to the onset or recurrence of a disease or disorder. For example, a subject could have a personal and/or family medical history that includes frequent occurrences of a particular disease or disorder, or could have had such a susceptibility determined by genetic screening. As part of a treatment regimen for a high risk individual, the individual is prophylactically treated to prevent the onset or recurrence of the disease or disorder. Prophylactically effective amounts of a pharmaceutical composition typically are determined by the effect they have compared to the effect observed when a second pharmaceutical composition lacking the active agent is administered to a similarly situated individual.

The DKK1 compositions described herein are useful for treating and/or preventing a variety of dermatological conditions, for instance a skin graft, an ulcer (such as a foot ulcer, particularly a diabetic foot ulcer), an abrasion, an injury caused by a repetitive impact or mechanical stress, age-related skin changes, skin damage due to steroid treatment, uneven skin pigmentation, hyperpigmentation, post-inflammatory pigmentation, ephelides, fragrance dermatitis, vitiligo (for instance, where depigmentation is desired in a subject with widespread vitiligo), a pigmented birthmark (particularly those characterized by the deposition of excess melanin), lentigos, or skin changes due to lichen simplex chronicus, melasma, porphyria cutanea tarda, Addison's disease, Peutz-Jeghers syndrome, acanthosis nigricans, hirsutism, congenital adrenal hyperplasia, polycystic ovarian syndrome, hypertrichosis, or anorexia nervosa. Topical DKK1 administration is useful for increasing skin thickness, decreasing skin pigmentation, decreasing unwanted hair growth, and treating or preventing melanoma.

For instance, in some embodiments the skin-thickening activities of topical DKK1 are useful when the subject has a skin graft, an ulcer, an abrasion, an injury caused by a repetitive impact or mechanical stress, age-related skin changes, or skin damage due to steroid treatment. Following treatment, the subject is monitored for changes in skin thickness and for alleviation of the symptoms of the injury, disorder, or disease state.

In other embodiments, topical DKK1 treatment is desirable because it reduces skin pigmentation. This is useful, for instance, when the subject has uneven skin pigmentation, hyperpigmentation, post-inflammatory pigmentation, fragrance dermatitis, sun-damaged skin, ephelides, vitiligo (for instance, where depigmentation is desired in a subject with widespread vitiligo), a pigmented birthmark, lentigos, lichen simplex chronicus, melasma, porphyria cutanea tarda, Addison's disease, Peutz-Jeghers syndrome, or acanthosis nigricans. Following treatment, the subject is monitored for changes in skin pigmentation and for alleviation of the symptoms of the disorder, or disease state.

In still other embodiments, topical DKK1 treatment is useful because it reduces hair growth. This is desirable, for example, in subjects who want to decrease hair growth on upper or lower extremities or on axillary skin for cosmetic reasons. Furthermore, topical DKK1 treatment is useful when the subject has hirsutism, congenital adrenal hyperplasia, polycystic ovarian syndrome, hypertrichosis, porphyria cutanea tarda, or anorexia nervosa.

In yet other embodiments, topical DKK1 treatment is effective as a treatment or preventive therapy for melanoma. Topical DKK1 is administered at least daily, and can be used in conjunction with other anti-cancer therapies, such as chemotherapy (for instance treatment with dacarbazine), immunotherapy (for instance treatment with interleukin-2, interferon, or imiquimod) as well as local perfusion, surgery, and/or radiation therapy. Treatment is generally continued until the desired tumor regression is achieved, and maintenance treatment may be useful even after complete regression of the tumor.

H. Methods for Treating Melasma

Provided herein is an exemplary protocol for treating a subject with melasma. However, one of skill in the art can see that such a treatment protocol is also suitable for the treatment of other hyperpigmentation conditions, for example uneven skin pigmentation, post-inflammatory pigmentation, ephelides, fragrance dermatitis, sun-damaged skin, a pigmented birthmark, lentigos, lichen simplex chronicus, melasma, porphyria cutanea tarda, Addison's disease, Peutz-Jeghers syndrome, acanthosis nigricans, or when depigmentation is desired in a subject with widespread vitiligo.

Topical DKK1 therapy is suitable for treating acute melasma as well as for maintaining the improvement seen following treatment of the acute condition. Briefly, a liposome-based DKK1 formulation is applied topically to the affected area of the subject twice daily, generally morning and evening. The typical dose of DKK1 ranges from 0.1 µg per kg of body weight to 1 µg per kg of body weight, depending on the severity of the condition, the age of the subject, and the sensitivity of the subject to adverse side effects such as burning or redness. Treatment is continued for at least six weeks or until the desired effect is achieved. In some cases, treatment is continued for 12, 24, 36 or more weeks. During the time of treatment, the subject is advised to avoid sun exposure.

Once the desired degree of skin lightening is achieved, DKK1 application is reduced to once a day. In some cases, treatment will continue indefinitely, whereas in other cases treatment is discontinued after a period of maintenance treatment.

I. Methods for Preventing Melanoma

This Example provides an exemplary protocol for preventing melanoma in a subject at risk for developing the condition. A subject may be at risk for developing melanoma, for instance, if she or he has a family history of skin cancer or a personal history of melanoma or excessive sun exposure. The disclosed method can be used to inhibit the development of abnormal pigmented lesions (such as nevi) that sometimes are precursors of melanoma, or can be used to treat suspicious lesions that are of irregular shape and/or increasing size.

Briefly, a microsponge-based DKK1 formulation is applied topically to the affected area of the subject twice daily, generally morning and evening. The typical dose of DKK1 ranges from 1 µg per kg of body weight to 10 µg per kg of body weight, depending on the age of the subject and the sensitivity of the subject to adverse side effects such as burning or redness. In some cases, treatment begins with a lower initial dose of DKK1 (for example 0.1 mg/kg body weight) before the full dose is administered. Treatment is continued for at least six weeks and may be continued for 12, 24, 36 or more weeks, or may be continued indefinitely.

After an initial period of treatment, the DKK1 dose may be decreased application is reduced to once a day. In some cases, treatment will continue indefinitely, whereas in other cases treatment is discontinued after a period of maintenance treatment.

In some embodiments, DKK1 is administered to a subject at risk of developing melanoma, particularly acral lentiginous melanoma, or to a subject who has already developed melanoma that has been surgically excised, through another route of administration, for instance through parenteral administration, targeted gene therapy, or other routes of administration, such as a micropump or sustained-release formulation. For instance, DKK1 can be administered in the form of a lentivirus over-expressing DKK1 whose expression is controlled by the expression of a melanocyte-specific gene, such as tyrosinase for example. This limits overexpression of DKK1 to melanocytes and in melanoma cells. In these embodiments, DKK1 is administered in a dose ranging from 0.01 µg per kg of body weight to 10 g per kg of body weight, depending on the age of the subject, the severity of the condition, and the sensitivity of the subject to adverse side effects.

J. Methods for Treating Thin Skin

Provided herein is an exemplary protocol for treating a subject with thin skin, for instance due to aging or treatment with topical steroids. However, one of skill in the art can see that such a treatment protocol is also suitable for the treatment of other conditions resulting in thin skin, for example when the subject has a skin graft, an ulcer, an abrasion, or an injury caused by a repetitive impact or mechanical stress. In some embodiments, the skin being treated is on the hands, for instance, in age-related thinning of the skin, and in certain examples, the DKK1 is provided in the form of a hand créme or lotion.

In some embodiments, the subject has a palmoplantar burn, a foot ulcer, for instance a diabetic foot ulcer, or another type of erosion injury, such as those resulting from collagen diseases, such as systemic sclerosis, poly arthritis nodosa, and rheumatoid arthritis. These types of skin injuries are treated, in some examples, with grafts of trunk-derived epidermis or tissue engineered from fibroblasts, which is induced by DKK1 to adopt a plantar phenotype. The plantar phenotype results in a more durable skin graft that is resistant to further damage. Thus, otherwise intractable palmoplantar wounds, for instance those with exposed bones, can be treated, for instance, with a combination of bone marrow exposure, occlusive dressing, epidermal grafting, and treatment with DKK1. See, for instance, Atiyeh et al., (2005) *Burns*, 31:944-956, for a review of methods of closing burns and other wounds; Wong et al., (2007) *Br. J. Dermatol.* 156:1149-1155, for a review of methods of using fibroblasts for tissue engineering; and Yamaguchi et al. (2004) *Br. J. Dermatol.* 151: 1019-1028, for methods of healing intractable diabetic foot ulcers with exposed bones, all of which are incorporated herein by reference. In each case, the graft tissue is exposed to DKK1, either before or after transplantation, in order to induce a durable palmoplantar phenotype.

Topical DKK1 therapy is suitable for treating acutely thinning skin or skin grafts, as well as for maintaining the improvement seen following treatment of the acute condition. Briefly, an emulsion-based DKK1 formulation is applied topically to the affected area of the subject twice daily, generally morning and evening. The typical dose of DKK1 ranges from 0.1 µg per kg of body weight to 1 µg per kg of body weight, depending on the severity of the condition, the age of the subject, and the sensitivity of the subject to adverse side effects such as burning or redness. In certain examples, about 10-1,000 ng/ml DKK1 is applied topically, for instance, from about 50 ng/ml to about 500 ng/ml, or about 100 ng/ml. Treatment is continued for at least six weeks or until the desired effect is achieved. In some cases, treatment is continued for 12, 24, 36 or more weeks.

Once the desired degree of skin thickening is achieved, DKK1 application is reduced to once a day. In some cases, treatment will continue indefinitely, whereas in other cases treatment is discontinued after a period of maintenance treatment.

Without further elaboration, it is believed that one skilled in the art can, using this description, utilize the present discoveries to their fullest extent. The following examples are illustrative only, and not limiting of the disclosure in any way whatsoever.

EXAMPLE 1

Materials and Methods Used for Evaluating the Effects of DKK1 on Melanocyte Function and Proliferation This Example provides representative materials and methods used for evaluating the effects of DKK1 on melanocyte function and proliferation that provide the therapeutic effects described herein.

Melanocyte Cultures

Neonatal human foreskin melanocytes were obtained from Cascade Biologics, Inc. (Portland, Oreg.). Melanocyte cultures were grown in melanocyte growth medium (MGM) consisting of Medium 154 (Cascade Biologics, Inc.) and HMGS (Cascade Biologics, Inc.). Melanocytes from the third to fifth passage were used in these experiments.

Microarray Procedures

Modified oligo-cDNA microarray analysis was performed as previously described with slight modifications (Yamaguchi et al., *J. Cell Biol.* 165:275-285, 2004). Briefly, total RNA was prepared from cultured human melanocytes treated with or without 50 ng/ml rhDKK1 (R&D Systems Inc., Minneapolis, Minn.) for two hours, using an RNeasy mini kit (Qiagen, Valencia, Calif.). The quality (purity and integrity) of extracted total RNA was confirmed using an Agilent 2100 Bioanalyzer with an RNA 6000 Nano Assay (Agilent Technology, Palo Alto, Calif.). Paired cDNA samples, labeled by cyanine 3- and cyanine 5-dUTP incorporation (Qiagen) during reverse transcription (Qiagen), were hybridized simultaneously with one oligo-DNA chip (Hs-Operon V2-vB2.2p13) as per National Cancer Institute (NCI) in-house protocol (available at http://mach1.nci.nih.gov/). Two fluorescent intensities of the oligo-DNA chip were scanned using a microarray scanner (GenePix 4000A; Axon Instruments, Inc., Molecular Devices Corp., Sunnyvale, Calif.). Differential gene expression was profiled with Genepix 3.0 software and was analyzed by NCI Center for Information Technology programs and databases. Experiments were performed in triplicate independently.

RT-PCR

To confirm the accuracy of oligo-cDNA microarrays, RT-PCR was performed. Oligonucleotide primers used for PCR were based on published mRNA sequences as follows: human PKCβ1 sense primer 5'-agtgccaagtttgctgcttt-3' (SEQ ID NO: 1); PKCβ1 antisense primer 5'-acaatgaggacgtccctgtc-3' (SEQ ID NO: 2); human Krn1 sense primer 5'-caagtttgctgggatggagt-3' (SEQ ID NO: 3); Krn1 antisense primer 5'-tgtcaaatagggggaagctg-3' (SEQ ID NO: 4); human LRP6 sense primer 5'-gctcagagtcccagttccag-3' (SEQ ID NO: 5); LRP6 antisense primer 5'-tcccttcatacgtggacaca-3' (SEQ ID NO: 6); human LDLR sense primer 5'-aagtgcatctctcggcagtt-3' (SEQ ID NO: 7); LDLR antisense primer 5'-tgcagtttccatcagagcac-3' (SEQ ID NO: 8); human GPR51 sense primer 5'-gctgctgatcgacctgtgta-3' (SEQ ID NO: 9); GPR51 antisense primer 5'-gatggtgctgcagaagatga-3' (SEQ ID NO: 10); human TNFRSF10A sense primer 5'-agagagaagtccctgcacca-3' (SEQ ID NO: 11); TNFSF10A antisense primer 5'-ttgtgagcattgtcctcagc-3' (SEQ ID NO: 12); human Gadd45β sense primer 5'-acagtgggggtgtacgagtc-3' (SEQ ID NO: 13); Gadd45β antisense primer 5'-gagatgtaggggacccactg-3' (SEQ ID NO: 14); MITF sense primer 5'-agagagcgagtgcccaggcatgaac-3' (SEQ ID NO: 15); MITF antisense primer 5'-tctttggccagtgctcttgcttcag-3' (SEQ ID NO: 16); GAPDH sense primer 5'-accacagtc-catgccatcac-3' (SEQ ID NO: 17); GAPDH antisense primer 5'-tccaccaccctgttgctgta-3' (SEQ ID NO: 18). After denaturation at 94° C. for two minutes, PCR was performed for 30 cycles (30 seconds at 94° C., one minute at 56° C. and one minute at 72° C.). All amplified products were sequence verified (Yamaguchi et al., *J. Cell Biol.* 165:275-285, 2004). Control reactions were performed in the absence of reverse transcriptase and were negative. Each experiment was repeated in triplicate independently.

Immunoblotting

Cultures from 100 mm dishes were solubilized in 500 μl M-PER® mammalian protein extraction reagent (Pierce Biotechnology, Rockford, Ill.) or extraction buffer containing 1% Nonidet P 40 (Calbiochem, San Diego, Calif.), 0.01% SDS, 0.1 M Tris:HCl, pH 7.2, and Protease Inhibitor cocktail (Roche, Mannheim, Germany). Protein concentrations of extracts were measured using the BCA protein assay kit (Pierce, Rockford, Ill.). Cell extracts (1 μg) were separated on 8-16% gradient SDS polyacrylamide gels (Invitrogen Corp, Carlsbad, Calif.). After electrophoresis, proteins were transferred electrophoretically from the gels to Immobilon-P transfer membranes (Millipore, Bedford, Mass.). The filters were incubated in the presence of antibodies to GSK3β (at 1:1,000, Cell Signaling Technology, Beverly, Mass.), pGSK3β (at 1:1,000, Cell Signaling Technology), PKCα (at 1:10,000, Sigma, St. Louis, Mo.), β-catenin (at 1:1,000, Cell Signaling Technology), ERK1/2 (p44/42 MAP Kinase antibody) (at 1:1,000, Cell Signaling Technology), or β-actin (at 1:3,000, AC-15, Abcam, Cambridge, Mass.) at room temperature for one hour, and were then incubated with horseradish peroxidase-linked anti-rabbit or anti-mouse whole antibodies (at 1:1,000, Amersham Bioscience, Pittsburgh, Pa.) at room temperature for one hour. Antigens were detected using an ECL-plus Western Blotting Detection System (Amersham).

Immunocytochemical Staining

Melanocyte cultures in two-well Lab-Tek chamber slides (Nalge Nunc International Corp., Naperville, Ill.) were processed for indirect immunofluorescence to detect the expression of signal transduction proteins using primary antibodies to GSK3β (1:50, Cell Signaling Tech), phospho-GSK3β which is specific for GSK3β phosphorylated at Ser9 (at 1:100, Cell Signaling Technology), β-catenin (at 1:50, Cell Signaling Technology) and PKCα (at 1:1,000, Sigma).

Bound antibodies were visualized with appropriate secondary antibodies, Alexa Fluor® 488 goat anti-rabbit IgG (H+L) (Molecular Probes, Inc., Eugene, Oreg.) at 37° C. for 30 minutes at 1:500 dilution with 5% goat serum. DAPI (Vector Laboratories Inc., Burlingame, Calif.) was used as a counter stain. The fluorescence of green produced by Alexa 488® and of blue by DAPI was observed and captured using a Leica DMR B/D MLD fluorescence microscope (Leica, Wetzlar, Germany) and a Dage-MTI 3CCD 3-chip color video camera (Dage-MTI, Michigan City, Ind.). Fluorescence was also observed using confocal laser scanning microscopy as described previously (Hoashi et al., *J. Biol. Chem.* 280:14006-14016, 2005).

3-Dimensional Skin Reconstructs

The epidermal equivalent MelanoDerm® is a reconstructed skin model provided commercially and obtained from MatTek Corp (Ashland, Mass., USA; www.mattek.com). Normal human keratinocytes and melanocytes used in those reconstructs were obtained from Asian neonatal foreskin tissues. MelanoDerms were grown at the air/liquid interface of the maintenance medium MEL-NHM-113 (MatTek Corp.), and the culture medium was renewed every two days. Where noted, the epidermis samples were supplemented with 100 ng/ml rhDKK1 every two days for 4 to 14 days. DKK1 was dissolved in PBS with 0.1% BSA and the same concentrations of PBS and BSA were employed for mock-treated controls.

Immunohistochemistry

Skin specimens obtained from matched palmoplantar areas (i.e. palms; n=1, and soles; n=4) and from non-palmoplantar areas (trunk; n=5) taken from five adult Asian subjects (ages ranged from 31 to 47) during cutaneous surgery. The expression of proteins related to signal transduction was detected by indirect immunofluorescence using the primary rabbit polyclonal antibodies described above. Mouse monoclonal antibody Ab-3 (1:100 dilution, NeoMarkers, Fremont, Calif.), which is specific for MART1, was additionally used as a primary antibody. Secondary antibodies used were Alexa Fluor® 594 goat anti-mouse IgG (H+L) and Alexa Fluor® 488 goat anti-rabbit IgG (H+L) (Molecular Probes, Inc.). The green fluorescence produced by Alexa 488® was superimposed over the red fluorescence produced by Alexa 594® to show co-localization.

EXAMPLE 2

Expression Levels of DKK1 mRNA in Palmoplantar and Non-palmoplantar Fibroblasts

This Example demonstrates that expression levels of DKK1 mRNA are up-regulated in human palmoplantar fibroblasts compared with non-palmoplantar fibroblasts, and that DKK1 has a number of immediate effects on melanocytes. DKK1 expression levels were confirmed in fibroblasts derived from palm or trunk skin at the protein level, using immunoblotting (FIG. 1A) and immunocytochemistry (FIG. 1B). The expression of DKK1 in three independent populations of palmoplantar-derived fibroblasts (Palm1, Palm2 and Palm3) was dramatically higher than in three independent populations of non-palmoplantar-derived fibroblasts (Trunk1, Trunk2 and Trunk3).

Normal human melanocytes were then treated with 50 ng/ml recombinant human DKK1 (rhDKK1) for two hours, and total RNA was harvested and analyzed using oligonucleotide-cDNA microarrays. The concentration of DKK1 used was determined in previous studies (Tian et al., *New Eng J Med* 349: 2483-2494, 2003; Yamaguchi et al., *J. Cell Biol.* 165:275-285, 2004). The complete database of gene expression patterns are reported in Supplementary Database 1 (http://www.ncbi.nlm.nih.gov/geo/query/acc.cgi?acc=GSE5515). In addition, these data have been deposited as a Gene Ontology report on a public database (http://www.ncbi.nlm.nih.gov/geo/) with a Series # of 'GSE5515'. The 30 genes with the largest increases or decreases in expression are listed in Table 2. Highly regulated genes also included some receptor-related genes (Table 3), Wnt-related genes (Table 4), melanocyte marker genes (Table 5) and Homeobox (HOX)-related genes (Table 6). DKK1 had various immediate effects on melanocytes, considering that affected genes are related to such diverse processes as mitochondrial function (e.g. MRPL38 and MRPS27), melanosome trafficking (for instance, HPS4, SV2B and STX5A) and transport (for instance, MLPH), apoptosis (for instance, Gadd45β and TNFRSF10A), Wnt signaling (for instance, β-catenin and PKC), as well as melanocyte development (for instance, HOX) and differentiation (for instance, MITF).

TABLE 2

Top 30 Genes Up-Regulated in Melanocytes by DKK1*

| DKK1/NS | DKK1 | NS | Gene | Description |
|---|---|---|---|---|
| 4.10 | 3206 | 782 | GLIO703 | Acid fibroblast growth factor-like protein |
| 3.71 | 4529 | 1222 | ASCL3 | Achaete-scute complex (*Drosophila*) homolog-like 3 (ASCL3) |
| 3.58 | 4847 | 1352 | GAD2 | glutamate decarboxylase 2 (pancreatic islets and brain, 65 kDa) (GAD2) |
| 3.40 | 3026 | 891 | FOXI1 | forkhead box I1 (FOXI1), transcript variant 2 |
| 3.39 | 3676 | 1084 | MBNL1 | Muscleblind-like (*Drosophila*) |
| 3.13 | 3747 | 1197 | CAV3 | caveolin 3 (CAV3), transcript variant 2 |
| 3.05 | 8675 | 2840 | FTL | Ferritin, light polypeptide |
| 2.91 | 5669 | 1946 | HSPC073 | HSPC073 |
| 2.79 | 4367 | 1567 | CTNNB1 | β1-Catenin (cadherin-associated protein), 88 kDa |
| 2.76 | 19609 | 7093 | MRPL38 | mitochondrial ribosomal protein L38 (MRPL38), nuclear gene encoding mitochondrial protein |
| 2.75 | 8914 | 3237 | SMAD6 | SMAD, mothers against DPP homolog 6 (*Drosophila*) (SMAD6) |
| 2.70 | 32276 | 11945 | ANK1 | Ankyrin 1, erythrocytic (ANK1), transcript variant 2 |
| 2.69 | 3182 | 1184 | MAGEC1 | melanoma antigen, family C, 1 (MAGEC1) |
| 2.66 | 19851 | 7476 | SV2B | synaptic vesicle glycoprotein 2B (SV2B) |
| 2.65 | 3305 | 1246 | MAPT | microtubule-associated protein tau (MAPT), transcript variant 4 |
| 2.63 | 15815 | 6018 | SAFB2 | Scaffold attachment factor B2 |
| 2.61 | 20135 | 7703 | UCN2 | urocortin 2 (UCN2) |
| 2.55 | 11300 | 4429 | SMP1 | small membrane protein 1 (SMP1) |
| 2.51 | 4550 | 1811 | VPS16 | Protein tyrosine phosphatase, receptor type, A |
| 2.50 | 7466 | 2988 | CML66 | Chronic myelogenous leukemia tumor antigen 66 (CML66) |
| 2.48 | 5439 | 2191 | LARGE | Like-glycosyltransferase |
| 2.48 | 34333 | 13862 | GADD45B | growth arrest and DNA-damage-inducible, beta (GADD45B) |
| 2.47 | 18397 | 7441 | MRPS27 | mitochondrial ribosomal protein S27 (MRPS27), nuclear gene encoding mitochondrial protein |
| 2.46 | 6687 | 2717 | PTE1 | peroxisomal acyl-CoA thioesterase (PTE1), transcript variant 3 |
| 2.43 | 18321 | 7544 | STX5A | Syntaxin 5A |
| 2.42 | 7998 | 3299 | NHP2L1 | NHP2 non-histone chromosome protein 2-like 1 (*S. cerevisiae*) (NHP2L1), transcript variant 1 |
| 2.42 | 5763 | 2382 | UMP-CMPK | UMP-CMP kinase (UMP-CMPK), mRNA. |
| 2.41 | 27789 | 11535 | DDX3Y | DEAD (Asp-Glu-Ala-Asp) box polypeptide 3, Y-linked (DDX3Y) |
| 2.40 | 5956 | 2479 | SLC43A1 | Solute carrier family 43, member 1 (SLC43A1) |
| 2.39 | 8759 | 3668 | TEF | Thyrotrophic embryonic factor |
| 2.38 | 5147 | 2159 | DTX2 | Deltex homolog 2 (*Drosophila*) (DTX2) |
| 2.38 | 4719 | 1983 | KCNJ2 | potassium inwardly-rectifying channel, subfamily J, member 2 (KCNJ2) |
| 0.02 | 130 | 8275 | PTK6 | PTK6 protein tyrosine kinase 6 |
| 0.02 | 235 | 10188 | ST18 | suppression of tumorigenicity 18 (breast carcinoma) (zinc finger protein) (ST18) |
| 0.03 | 525 | 19158 | MBD2 | methyl-CpG binding domain protein 2 (MBD2), transcript variant 1 |
| 0.03 | 183 | 5751 | CAPS2 | calcyphosphine 2 (CAPS2) |
| 0.04 | 239 | 6389 | RDS | retinal degeneration, slow (RDS) |
| 0.05 | 582 | 10693 | | Similar to Kruppel-like factor 7 (ubiquitous); ubiquitous Kruppel-like transcription factor |
| 0.08 | 302 | 3958 | DHRS2 | dehydrogenase/reductase (SDR family) member 2 (DHRS2), transcript variant 2 |
| 0.09 | 314 | 3674 | MASP1 | mannan-binding lectin serine protease 1 (C4/C2 activating component of Ra-reactive factor) (MASP1), transcript variant 1 |
| 0.09 | 554 | 6169 | ADMR | adrenomedullin receptor (ADMR) |
| 0.09 | 4744 | 50882 | LAMC3 | laminin, gamma 3 (LAMC3) |
| 0.10 | 2017 | 19655 | CA12 | Carbonic anhydrase XII |
| 0.11 | 452 | 3967 | MGEA5 | Meningioma expressed antigen 5 (hyaluronidase) |
| 0.12 | 906 | 7352 | VCP | Valosin-containing protein |
| 0.15 | 1189 | 8187 | SPON2 | Spondin 2, extracellular matrix protein |
| 0.15 | 1169 | 7870 | VMP | vesicular membrane protein p24 (VMP) |
| 0.16 | 2614 | 16432 | HIST1H2BO | histone 1, H2bo (HIST1H2BO) |
| 0.17 | 1686 | 9902 | MNT | MAX binding protein (MNT) |
| 0.17 | 6374 | 36625 | BHLHB3 | basic helix-loop-helix domain containing, class B, 3 (BHLHB3) |
| 0.23 | 4341 | 18614 | PTPN23 | protein tyrosine phosphatase, non-receptor type 23 (PTPN23) |
| 0.24 | 1719 | 7160 | RGS11 | regulator of G-protein signalling 11 (RGS11), transcript variant 1 |
| 0.25 | 6640 | 27095 | PTP4A1 | Protein tyrosine phosphatase type IVA, member 1 |
| 0.25 | 2536 | 10173 | IPO8 | importin 8 (IPO8) |
| 0.27 | 1137 | 4152 | SLC39A11 | Solute carrier family 39 (metal ion transporter), member 11 |
| 0.27 | 8137 | 29601 | PFKFB4 | 6-phosphofructo-2-kinase/fructose-2,6-biphosphatase 4 (PFKFB4) |
| 0.28 | 7019 | 25498 | ZBTB4 | zinc finger and BTB domain containing 4 (ZBTB4) |
| 0.28 | 2171 | 7643 | HKR1 | GLI-Kruppel family member HKR1 (HKR1) |
| 0.30 | 4633 | 15631 | DHPS | deoxyhypusine synthase (DHPS), transcript variant 3 |
| 0.32 | 2112 | 6649 | TORC3 | transducer of regulated cAMP response element-binding protein (CREB) 3 (TORC3) |
| 0.33 | 1897 | 5709 | GNPDA2 | glucosamine-6-phosphate deaminase 2 (GNPDA2) |
| 0.34 | 6899 | 20516 | NIT2 | nitrilase family, member 2 (NIT2) |

**Genes listed are those whose expression levels in mock-treated melanocytes were >3,000 (65,000 is the maximum) after 2 hr treatment with rhDKK1; data are reported as means of 3 independent experiments.

Figure 2:
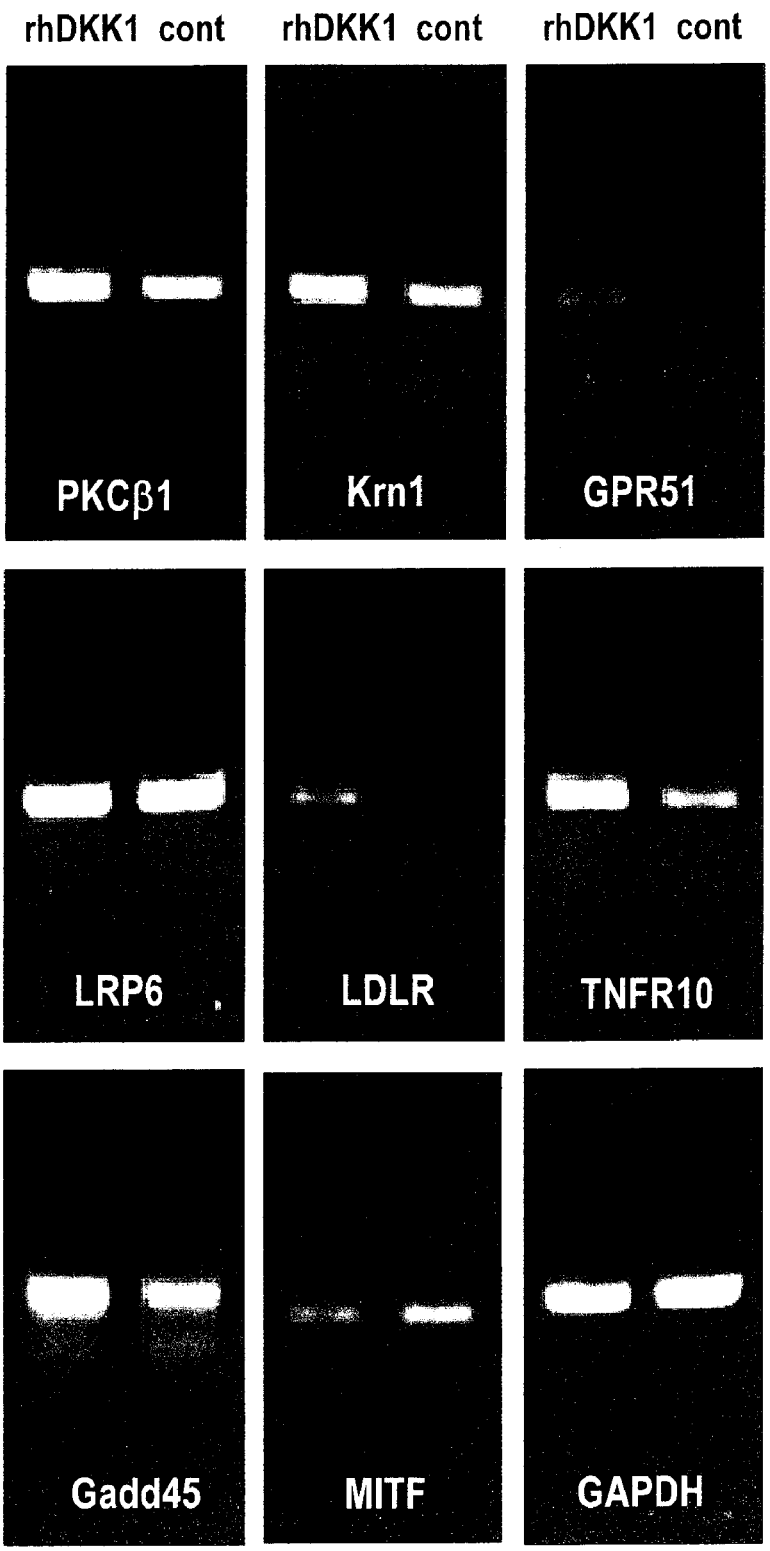
FIG. 2 is a set of digital images of gels validating gene expression levels using RT-PCR in normal human melanocytes untreated (control) or treated with 50 ng/ml rhDKK1 for two hours. The expression of $PKC\beta 1$ ($p=<0.0001$), Krn1 ($p=<0.0001$), LRP6 ($p=0.065$), LDLR ($p=<0.001$), GPR51 ($p=<0.01$), TNFR10 ($p=<0.0001$) and Gadd45 ($p=<0.002$) is up-regulated in melanocytes when treated with rhDKK1, but MITF ($p=<0.001$) is down-regulated. GAPDH expression served as control ($p=0.41$) ($n>=3$).

The mRNA expression levels of about 40 of those genes were validated using RT-PCR (FIG. 2), levels of several genes related to Wnt signaling were confirmed to be significantly up-regulated in response to rhDKK1 (for instance, β-catenin and PKCβ1, p<0.0001), as were receptors (for instance, Krn1 (p<0.0001), LDLR (p<0.001), GPR51 (p<0.01) and TNFRSF10A (p<0.0001)) and markers of apoptosis (for instance, Gadd45β, p=0.0016), whereas MITF was significantly down-regulated (p<0.001) by rhDKK1. Interestingly, the level of β-catenin mRNA did not correlate with the protein level, as previously reported (Yamaguchi et al., *J. Cell Biol.* 165:275-285, 2004).

TABLE 3

Receptor-Related Genes Up-Regulated in Melanocytes by DKK1*

| DKK1/NS | DKK1 | NS | Gene | Description |
|---|---|---|---|---|
| 3.27 | 2385 | 729 | GPR51 | G protein-coupled receptor 51 |
| 3.17 | 2172 | 686 | PTGDR | prostaglandin D2 receptor (DP) (PTGDR) |
| 3.06 | 1782 | 582 | OR11A1 | olfactory receptor, family 11, subfamily A, member 1 (OR11A1) |
| 2.83 | 2557 | 905 | RARB | retinoic acid receptor, beta (RARB), transcript variant 2, mRNA. |
| 2.78 | 2249 | 810 | TNFRSF10A | tumor necrosis factor receptor superfamily, member 10a (TNFRSF10A) |
| 2.72 | 1718 | 631 | NR3C2 | Nuclear receptor subfamily 3, group C, member 2 |
| 2.69 | 2097 | 780 | OXTR | oxytocin receptor (OXTR) |
| 2.63 | 1593 | 605 | DRD5 | dopamine receptor D5 (DRD5) |
| 2.62 | 1028 | 392 | KIR3DL3 | killer cell immunoglobulin-like receptor, three domains, long cytoplasmic tail, 3 (KIR3DL3) |
| 2.53 | 1908 | 755 | XCR1 | chemokine (C motif) receptor 1 (XCR1) |
| 2.51 | 4550 | 1811 | VPS16 | Protein tyrosine phosphatase, receptor type, A |
| 2.45 | 3595 | 1466 | PTGER3 | Prostaglandin E receptor 3 (subtype EP3) |
| 2.17 | 1810 | 833 | THRAP2 | Thyroid hormone receptor associated protein 2 |
| 2.17 | 2050 | 944 | ANTXR2 | anthrax toxin receptor 2 (ANTXR2) |
| 1.99 | 10308 | 5177 | EDG5 | endothelial differentiation, sphingolipid G-protein-coupled receptor, 5 (EDG5) |
| 1.97 | 5508 | 2801 | GPR20 | G protein-coupled receptor 20 (GPR20) |
| 1.94 | 13038 | 6736 | TRAF4 | TNF receptor-associated factor 4 (TRAF4), transcript variant 1 |
| 1.90 | 8906 | 4693 | NGFR | nerve growth factor receptor (TNFR superfamily, member 16) (NGFR) |
| 1.86 | 2487 | 1337 | BMPR1A | bone morphogenetic protein receptor, type IA (BMPR1A) |
| 1.81 | 3949 | 2179 | KDELR3 | KDEL endoplasmic reticulum protein retention receptor 3 (KDELR3), transcript variant 1 |
| 1.81 | 38066 | 21087 | TRIP6 | thyroid hormone receptor interactor 6 (TRIP6) |
| 1.70 | 7190 | 4229 | LRP6 | low density lipoprotein receptor-related protein 6 (LRP6) |
| 1.66 | 1200 | 725 | KREMEN1 | kringle containing transmembrane protein 1 (KREMEN1), transcript variant 2 |
| 1.65 | 5379 | 3258 | OR1G1 | olfactory receptor, family 1, subfamily G, member 1 (OR1G1) |
| 1.63 | 23658 | 14556 | PTPN11 | protein tyrosine phosphatase, non-receptor type 11 (Noonan syndrome 1) (PTPN11) |
| 1.62 | 45217 | 27857 | SCARB2 | scavenger receptor class B, member 2 (SCARB2) |
| 1.62 | 5749 | 3558 | LDLR | low density lipoprotein receptor (familial hypercholesterolemia) (LDLR) |
| 1.59 | 15817 | 9966 | RARA | retinoic acid receptor, alpha (RARA) |
| 1.56 | 36705 | 23574 | KDELR2 | KDEL (Lys-Asp-Glu-Leu) endoplasmic reticulum protein retention receptor 2 (KDELR2) |
| (1.35) | 14716 | 10905 | MC1R | melanocortin 1 receptor (alpha melanocyte stimulating hormone receptor) (MC1R) |
| (0.94) | 1193 | 1263 | KREMEN2 | kringle containing transmembrane protein 2 (KREMEN2), transcript variant 2 |

*Genes listed are those whose expression levels in DKK1-treated melanocytes were >1,000 (65,000 is the maximum) after 2 hr treatment with rhDKK1; data for genes with DKK1/NS ratio >1.45 are reported as means of 3 independent experiments.

TABLE 4

Wnt Related Genes Up-Regulated in Melanocytes by DKK1*

| DKK1/NS | DKK1 | NS | Gene | Description |
|---|---|---|---|---|
| 3.37 | 2502 | 742 | CXXC4 | CXXC finger 4 (CXXC4) |
| 3.12 | 1405 | 451 | WNT16 | wingless-type MMTV integration site family, member 16 (WNT16), transcript variant 2 |
| 2.79 | 4367 | 1567 | CTNNB1 | β1-Catenin (cadherin-associated protein), 88 kDa |
| 2.52 | 1127 | 447 | WNT9B | wingless-type MMTV integration site family, member 9B (WNT9B) |
| 2.51 | 1545 | 615 | PRKCBP1 | Protein kinase C binding protein 1 |
| 2.32 | 6115 | 2633 | PPP2R2C | protein phosphatase 2 (formerly 2A), regulatory subunit B (PR 52), γ isoform (PPP2R2C), transcript variant 2 |
| 2.21 | 1582 | 717 | BCL9 | B-cell CLL/lymphoma 9 (BCL9) |
| 2.19 | 1529 | 697 | WNT3A | wingless-type MMTV integration site family, member 3A (WNT3A) |
| 2.08 | 2335 | 1123 | SOX17 | SRY (sex determining region Y)-box 17 (SOX17) |
| 2.07 | 1502 | 725 | DVL2 | dishevelled, dsh homolog 2 (*Drosophila*) (DVL2) |
| 2.06 | 25580 | 12391 | YY1 | YY1 transcription factor (YY1) |
| 1.99 | 1658 | 833 | WNT3 | wingless-type MMTV integration site family, member 3 (WNT3) |
| 1.93 | 1565 | 810 | PRKX | protein kinase, X-linked (PRKX) |

TABLE 4-continued

Wnt Related Genes Up-Regulated in Melanocytes by DKK1*

| DKK1/NS | DKK1 | NS | Gene | Description |
|---|---|---|---|---|
| 1.89 | 21691 | 11480 | PRICKLE1 | prickle-like 1 (*Drosophila*) (PRICKLE1) |
| 1.87 | 1665 | 890 | WNT10B | wingless-type MMTV integration site family, member 10B (WNT10B) |
| 1.87 | 8377 | 4478 | DKK1 | dickkopf homolog 1 (*Xenopus laevis*) (DKK1) |
| 1.85 | 1458 | 786 | PRKCB1 | Protein kinase C, β1 |
| 1.84 | 2255 | 1223 | WIF1 | WNT inhibitory factor 1 (WIF1) |
| 1.77 | 8056 | 4543 | CSNK1G3 | casein kinase 1, gamma 3 (CSNK1G3) |
| 1.77 | 1173 | 663 | CCND2 | cyclin D2 (CCND2) |
| 0.31 | 424 | 1384 | SIAH1 | Seven in absentia homolog 1 (*Drosophila*) |
| 0.37 | 760 | 2076 | WNT5A | Wingless-type MMTV integration site family, member 5A |
| 0.49 | 13467 | 27466 | WNT7A | wingless-type MMTV integration site family, member 7A (WNT7A) |
| 0.50 | 577 | 1165 | WISP1 | WNT1 inducible signaling pathway protein 1 |
| 0.51 | 7711 | 15017 | CSNK1G2 | casein kinase 1, gamma 2 (CSNK1G2) |
| 0.52 | 1105 | 2140 | PRKCI | protein kinase C, iota (PRKCI) |
| 0.53 | 3251 | 6080 | PRKCABP | protein kinase C, alpha binding protein (PRKCABP) |
| 0.58 | 3343 | 5731 | ROCK1 | Rho-associated, coiled-coil containing protein kinase 1 (ROCK1) |
| 0.59 | 681 | 1147 | PLCG1 | phospholipase C, gamma 1 (PLCG1), transcript variant 2 |
| 0.60 | 3521 | 5906 | SMAD4 | SMAD, mothers against DPP homolog 4 (*Drosophila*) (SMAD4) |
| 0.61 | 21107 | 34437 | MITF | microphthalmia-associated transcription factor (MITF), transcript variant 5 |
| 0.61 | 12375 | 20423 | CSNK1A1 | casein kinase 1, alpha 1 (CSNK1A1) |
| 0.61 | 4983 | 8217 | CUL1 | cullin 1 (CUL1) |
| 0.61 | 1490 | 2449 | PPP3CC | Protein phosphatase 3 (formerly 2B), catalytic subunit, gamma isoform (calcineurin A gamma) |
| 0.61 | 1286 | 2100 | TCF7L2 | transcription factor 7-like 2 (T-cell specific, HMG-box) (TCF7L2) |
| 0.63 | 7224 | 11484 | PKN2 | protein kinase N2 (PKN2) |
| 0.65 | 5674 | 8763 | ROCK2 | Rho-associated, coiled-coil containing protein kinase 2 (ROCK2) |
| 0.65 | 1499 | 2300 | VANGL2 | PREDICTED: *Homo sapiens* vang-like 2 (van gogh, *Drosophila*) (VANGL2) |
| 0.66 | 4450 | 6699 | MAPK9 | Mitogen-activated protein kinase 9 (MAPK9), transcript variant 2 |

*Genes listed are those whose expression levels in mock-treated melanocytes were >1,000 (65,000 is the maximum) after 2 hr treatment with rhDKK1; data for genes with DKK1/NS ratio <0.70 are reported as means of 3 independent experiments.

TABLE 5

Melanogenic Markers Up-Regulated in Melanocytes by DKK1*

| DKK1/NS | DKK1 | NS | Gene | Description |
|---|---|---|---|---|
| 2.74 | 2947 | 1076 | LOC51152 | Melanoma antigen |
| 2.69 | 3182 | 1184 | MAGEC1 | melanoma antigen, family C, 1 (MAGEC1) |
| 2.06 | 8469 | 4105 | MAGEC2 | melanoma antigen, family C, 2 (MAGEC2) |
| 1.99 | 1705 | 855 | BAGE4 | B melanoma antigen family, member 4 (BAGE4) |
| 1.96 | 21576 | 11021 | MAGEF1 | melanoma antigen, family F, 1 (MAGEF1) |
| 1.71 | 2557 | 1495 | MLPH | Melanophilin |
| 1.69 | 1013 | 598 | MAGEC3 | melanoma antigen, family C, 3 (MAGEC3), transcript variant 2 |
| 1.66 | 50952 | 30701 | MATP | membrane associated transporter (MATP) |
| 1.58 | 1050 | 664 | AIM1 | PREDICTED: *Homo sapiens* absent in melanoma 1 (AIM1) |
| 1.56 | 5957 | 3816 | HPS4 | Hermansky-Pudlak syndrome 4 (HPS4), transcript variant 2 |
| 0.48 | 635 | 1311 | MIA2 | melanoma inhibitory activity 2 (MIA2) |
| 0.61 | 21107 | 34437 | MITF | microphthalmia-associated transcription factor (MITF), transcript variant 5 |
| 0.62 | 1285 | 2062 | RPS6KA1 | ribosomal protein S6 kinase, 90 kDa, polypeptide 1 (RPS6KA1) |
| 0.64 | 15172 | 23576 | DDT | D-dopachrome tautomerase (DDT) |
| 0.70 | 2426 | 3489 | MCAM | melanoma cell adhesion molecule (MCAM) |
| 0.70 | 1043 | 1499 | BCL2 | B-cell CLL/lymphoma 2 |

*Genes listed are those whose expression levels in mock-treated melanocytes were >1,000 (65,000 is the maximum) after 2 hr treatment with rhDKK1; data for genes with DKK1/NS ratio <0.70 are reported as means of 3 independent experiments.

EXAMPLE 3

DKK1 and Expression Patterns of Proteins Related to Wnt Signaling Pathways

Figure 3:
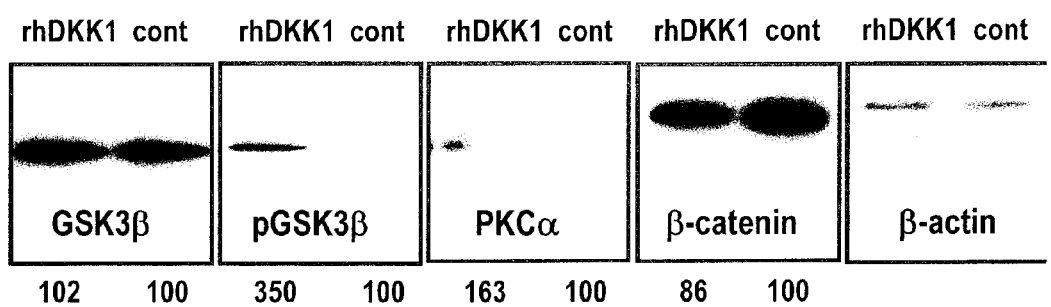
FIG. 3 is a set of digital images of gels validating expression levels of proteins related to Wnt signaling pathways in normal human melanocytes untreated (control) or treated with 50 ng/ml rhDKK1 for two hours (FIG. 3A) or five days (FIG. 3B) by immunoblotting. Numbers under the gels indicate levels of intensity compared with $\beta$-actin.
Figure 3:
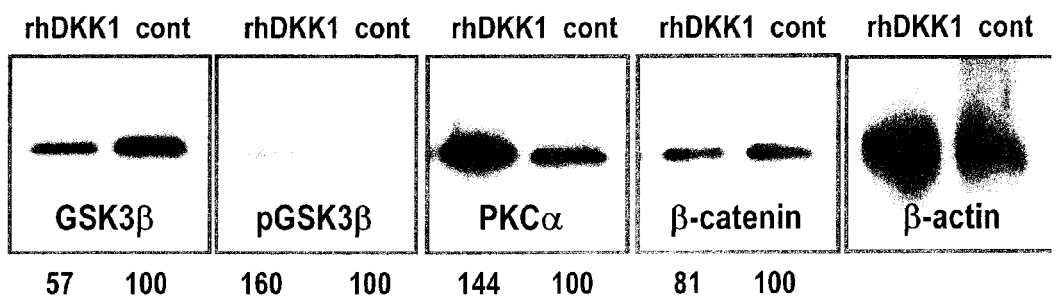
Figure 4:
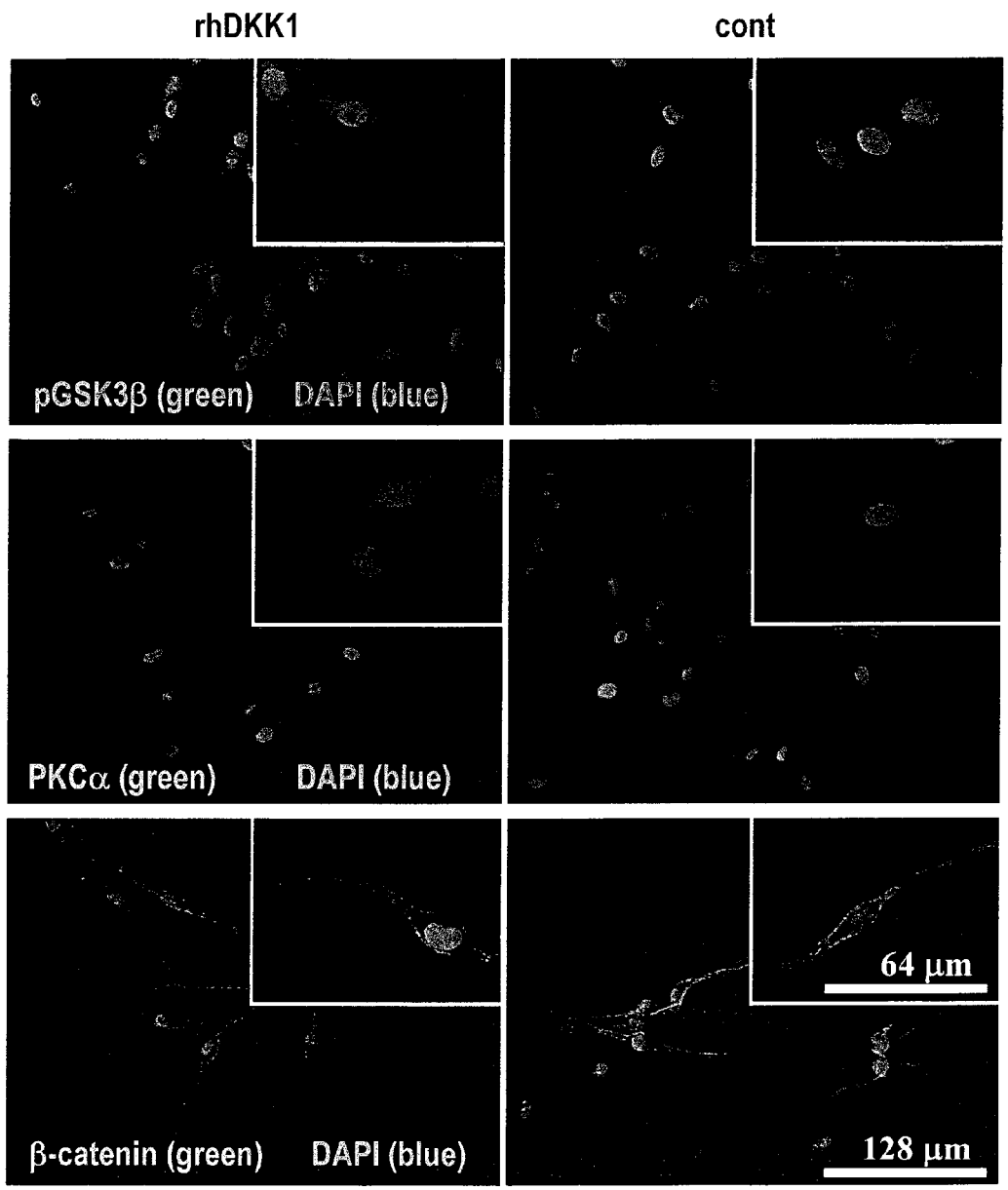
FIG. 4 is a set of digital images showing the expression of $pGSK3\beta$, $PKC\alpha$ and $\beta$-catenin by normal human melanocytes untreated (control) or treated with 50 ng/ml rh DKK1 for two hours by immunocytochemistry. The expression of $GSK3\beta$ phosphorylated at Ser9 and $PKC\alpha$ is up-regulated in response to rhDKK1, but $\beta$-catenin expression is down-regulated. Fluorescence marks antibody staining, nuclei are stained with DAPI.

This example illustrates the effects of DKK1 on the expression patterns of proteins related to Wnt signaling pathways in more detail. Cell extracts were harvested after two hours (FIG. 3A) and after 5 days (FIG. 3B) of treatment with rhDKK1 and analyzed them by Western blotting. Overall, GSK3β expression was unchanged at two hours but was slightly down-regulated after five days of treatment with rhDKK1. However, GSK3β phosphorylated at Ser9 was dramatically up-regulated in response to rhDKK1 within two hours, and that was also seen after five days of treatment. PKCα expression was also increased at both time points examined. As previously reported, β-catenin expression was down-regulated after two hours or five days of rhDKK1 treatment. Consistent results were confirmed by immunocytochemistry of rhDKK1- or mock-treated melanocytes (FIG. 4).

TABLE 6

HOX Related Genes Up-Regulated in Melanocytes by DKK1*

| DKK1/NS | DKK1 | NS | Gene | Description |
|---|---|---|---|---|
| 2.71 | 2335 | 860 | HOXA4 | homeo box A4 (HOXA4) |
| 2.23 | 1398 | 628 | HOXB9 | Homeo box B9 |
| 2.17 | 2405 | 1111 | HOXA10 | homeo box A10 (HOXA10), transcript variant 2 |
| 1.93 | 1148 | 594 | PHTF1 | Putative homeodomain transcription factor 1 |
| 1.90 | 1607 | 847 | PROP1 | prophet of Pit1, paired-like homeodomain transcription factor (PROP1) |
| 1.78 | 11115 | 6261 | MEOX1 | Mesenchyme homeo box 1 |
| 1.76 | 7694 | 4364 | PHTF1 | putative homeodomain transcription factor 1 (PHTF1) |
| 1.76 | 1483 | 842 | HOXB9 | homeo box B9 (HOXB9) |
| 1.70 | 7989 | 4708 | PKNOX2 | PBX/knotted 1 homeobox 2 (PKNOX2) |
| 1.62 | 1541 | 951 | DLX4 | distal-less homeobox 4 (DLX4), transcript variant 2 |
| 1.59 | 2565 | 1612 | PHOX2A | Paired-like (aristaless) homeobox 2a |
| 1.58 | 1033 | 652 | LHX3 | LIM homeobox 3 (LHX3), transcript variant 1 |
| 1.56 | 5171 | 3307 | HOXB13 | homeo box B13 (HOXB13) |
| 1.53 | 1802 | 1181 | VAX2 | ventral anterior homeobox 2 (VAX2) |
| 1.52 | 4812 | 3158 | PHC1 | polyhomeotic-like 1 (*Drosophila*) (PHC1) |
| 1.46 | 1048 | 716 | ZHX3 | zinc fingers and homeoboxes 3 (ZHX3) |
| 1.46 | 1196 | 817 | HOP | Homeodomain-only protein |
| 0.26 | 567 | 2186 | LOC360030 | Homeobox C14 |
| 0.41 | 607 | 1487 | ISL1 | ISL1 transcription factor, LIM/homeodomain, (islet-1) (ISL1) |
| 0.44 | 447 | 1025 | DUX2 | Double homeobox, 2 |
| 0.48 | 2649 | 5519 | ZHX2 | zinc fingers and homeoboxes 2 (ZHX2) |
| 0.48 | 4075 | 8468 | HOXB7 | homeo box B7 (HOXB7) |
| 0.55 | 700 | 1261 | HESX1 | homeo box (expressed in ES cells) 1 (HESX1) |
| 0.57 | 674 | 1185 | IPF1 | insulin promoter factor 1, homeodomain transcription factor (IPF1) |
| 0.58 | 1373 | 2364 | HOP | homeodomain-only protein (HOP), transcript variant 2 |
| 0.62 | 1518 | 2461 | ZHX1 | Zinc fingers and homeoboxes 1 |
| 0.62 | 996 | 1597 | HMX1 | homeo box (H6 family) 1 (HMX1) |
| 0.64 | 1002 | 1565 | PHOX2B | paired-like homeobox 2b (PHOX2B) |
| 0.66 | 3887 | 5918 | CHERP | calcium homeostasis endoplasmic reticulum protein (CHERP) |
| 0.66 | 3244 | 4920 | ASH2L | ash2 (absent, small, or homeotic)-like (*Drosophila*) (ASH2L) |
| 0.67 | 4117 | 6182 | PHTF2 | putative homeodomain transcription factor 2 (PHTF2) |
| 0.67 | 933 | 1391 | HOXB2 | homeo box B2 (HOXB2) |
| 0.69 | 844 | 1230 | HOXA5 | homeo box A5 (HOXA5) |
| 0.69 | 1058 | 1524 | HOXD8 | homeo box D8 (HOXD8) |
| 0.70 | 804 | 1148 | DMBX1 | diencephalon/mesencephalon homeobox 1 (DMBX1), transcript variant 1 |

*Genes listed are those whose expression levels in mock-treated melanocytes were >1,000 (65,000 is the maximum) after 2 hr treatment with rhDKK1; data for genes with DKK1/NS ratio <0.70 are reported as means of 3 independent experiments.

EXAMPLE 4

Figure 5:
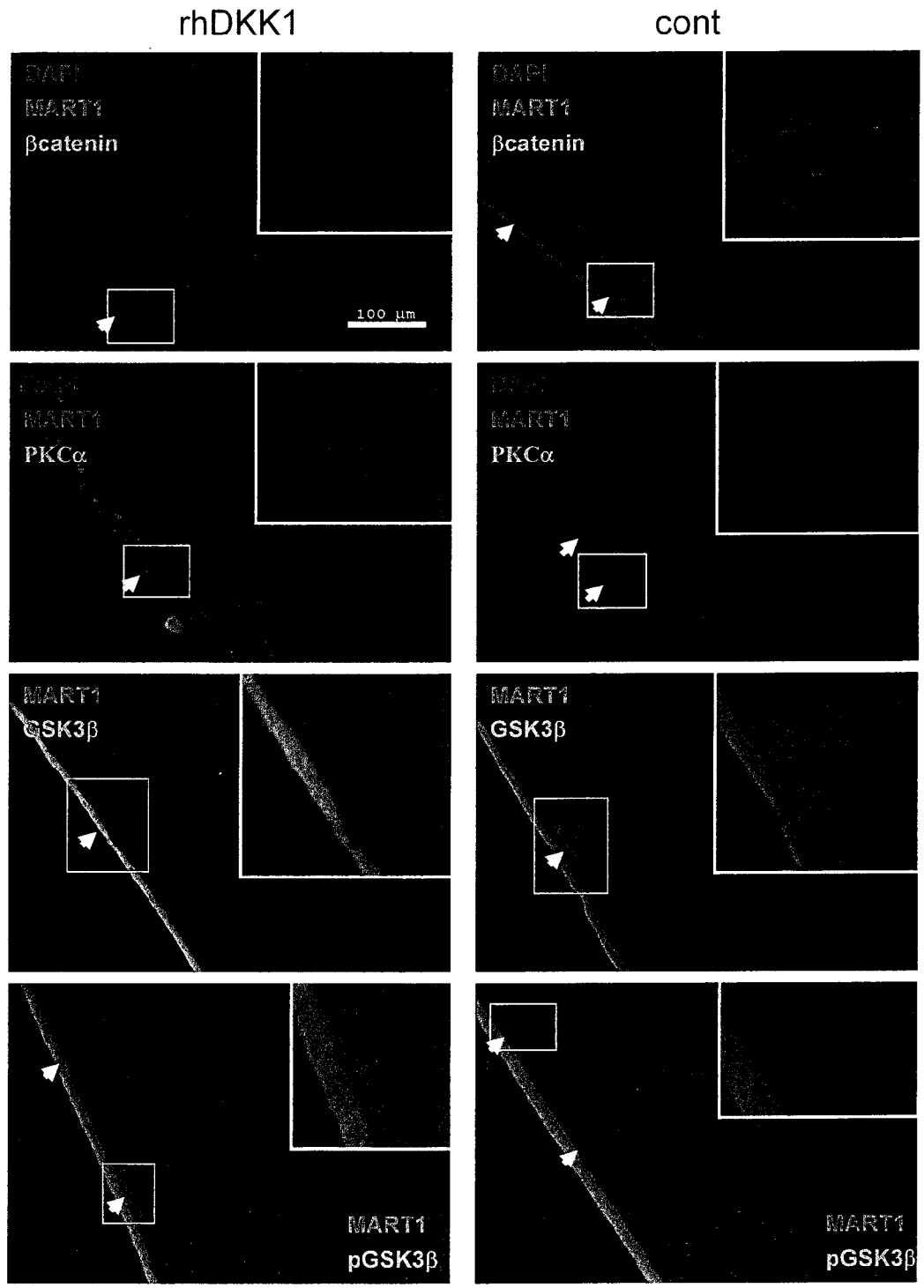
FIG. 5 is a set of digital images showing immunostaining for $\beta$-catenin, $PKC\alpha$, $GSK\beta$ and Ser9-phosphorylated $GSK\beta$ in the reconstructed epidermis after ten days of treatment with or without 100 ng/ml rhDKK1. Note the decreased expression of $\beta$-catenin and $GSK3\beta$ and the increased expression of $PKC\alpha$ and Ser9-phosphorylated $GSK3\beta$.

Secretion of DKK1 by Fibroblasts is Responsible for the Physiological Differences between Palmoplantar Skin and Non-palmoplantar Skin This Example demonstrates that secretion of DKK1 by fibroblasts is responsible for the physiological differences observed between palmoplantar skin and non-palmoplantar skin. Three-dimensional skin reconstructs (termed Melano-Derm) were used that consist of normal human keratinocytes and melanocytes grown at the air/liquid interface of the maintenance medium in the presence or absence of 100 ng/ml rhDKK1 for four to 14 days (FIG. 5). The immunostaining of these skin reconstructs was consistent with the findings of melanocyte cultures, as shown above, and revealed decreased expression of β-catenin and GSK3β but increased expression of PKCα and Ser9-phosphorylated GSK3β.

Figure 6:
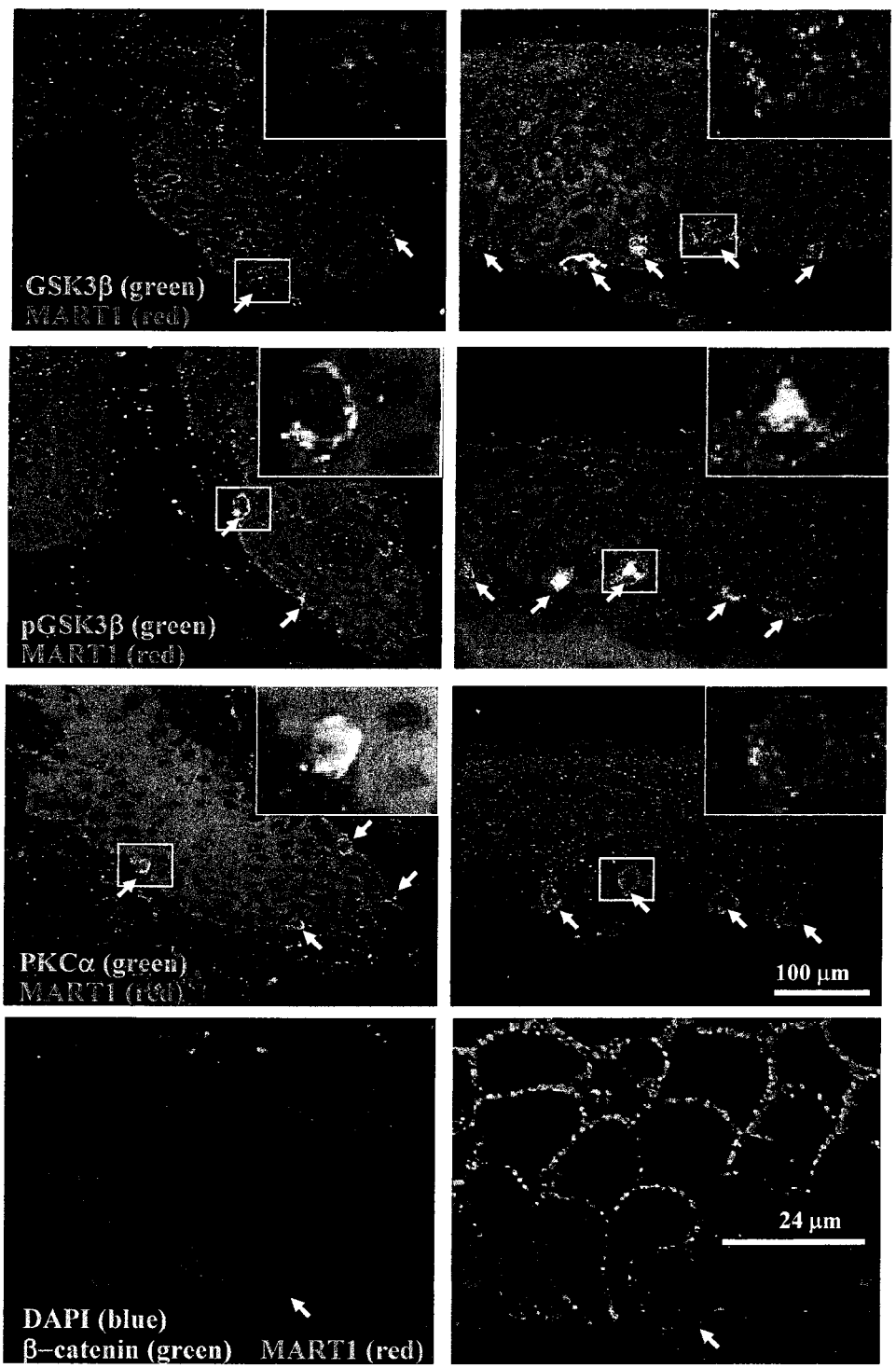
FIG. 6 is a set of digital images showing immunohistochemistry for $GSK\beta$, $PKC\alpha$ and $\beta$-catenin in palmoplantar and non-palmoplantar skin in situ. Melanocytes in the skin are identified by MART-1 staining. Palm skin (left) shows low expression of $GSK3\beta$ but high expression of $GSK3\beta$ phosphorylated at Ser9 and of $PKC\alpha$. In contrast, levels of $\beta$-catenin expression are lower in palmoplantar melanocytes in situ compared with melanocytes in trunk skin (right).

These in vitro results were confirmed using immunohistochemistry of human skin in situ. Melanocytes in palmoplantar skin, which are adjacent to dermal fibroblasts with high expression levels of DKK1, showed relatively low expression of GSK3β (FIG. 6), but high expression of GSK3β phosphorylated at Ser 9 and of PKCα. In contrast, levels of β-catenin expression were decreased in melanocytes in palmoplantar epidermis.

EXAMPLE 5

Effects of DKK1 on Melanocyte Function and Proliferation, a Summary

This Example summarizes and expands on the data presented in the previous three Examples, and clarifies the mechanisims by which DKK1 can lighten pigmented skin. As described above, Western blotting and immunohistochemistry were used to confirm that DKK1 expression is significantly higher in human fibroblasts derived from palmoplantar skin (which is unpigmented) compared with those derived from non-palmoplantar skin. The effects of rhDKK1 on human melanocytes were then demonstrated using a multidisciplinary approach that included gene profile analysis and the investigation of signal transduction protein expression patterns. The expression of a large number of Wnt-related genes (including PKCβ1, Krn1 and LRP6) is quickly up-regulated in melanocytes in response to rhDKK1. Genes encoding receptors other than the known DKK1 receptors (Krn1 and LRP6) also show up-regulated expression within two hours after treatment with rhDKK1, suggesting that low-density lipoprotein receptor (LDLR), GPR51 and TNFRSF10A (also known as TRAIL R1) are responsive to DKK1.

LDLR is related to LRP6, which has a DKK1 binding site (Mao et al., *Nature* 411:321-325, 2001), with an alignment score of 706 by ClustalW at the amino acid level and with a score of 230 bits by BlastP. GPR51 (also known as GABABR2 (Li et al., *J Invest Dermatol* 123:622-633, 2003)) is related to MC1R, a critical receptor expressed specifically by melanocytes (Rouzaud et al., *Mutat Res* 571: 133-152, 2005), since both of them are G-coupled protein receptors with an alignment score of 6365 by ClustalW at the basic pair level. TNFRSF10A is known as a death receptor that leads to p53-independent apoptosis via caspase cleavage (Xu and El-Deiry, *Biochem Biophys Res Commun* 269: 179-190, 2000, 2000), and its up-regulation indicates that DKK1 induces melanocyte apoptosis via this receptor. The concept that DKK1 induces apoptosis in melanocytes also derives from the finding that the expression of Gadd45β, which induces apoptosis via the p38 MAPK pathway (Sarkar et al., *Proc Natl Acad Sci USA* 99: 10054-10059, 2002), is also up-regulated in melanocytes treated with rhDKK1. In other words, the inhibition of melanocyte growth by DKK1 likely involves the up-regulated expression of TNFRSF10A and/or Gadd45β.

The microarray analyses also indicate numerous other candidate genes which help explain the suppression of melanocyte growth and/or function by DKK1. As examples, vitiligo is an acquired pigmentary disorder characterized by progressive areas of depigmenting skin which result from the loss of melanocytes in those hypopigmented regions. Vitiligo has been associated with thyroid disorders including Hashimoto thyroiditis and Graves disease (Grimes, *J Amer Med Assoc* 293: 730-735, 2005, 2005), and has also been associated with oxidative stress, in particular with increased levels of intracellular reactive oxygen species regulated by mitochondria (Dell'Anna et al., *J Invest Dermatol* 117: 908-913, 2001). Expression levels of thyrotrophic embryonic factor and mitochondrial ribosomal proteins are increased >2.3-fold by treatment with rhDKK1 which helps explain increased melanocyte toxicity in DKK1-rich tissue. The melanocyte toxicity would be expected to decrease pigmentation.

Trafficking of melanosomal proteins within melanocytes plays critical roles in regulating the synthesis, deposition and distribution of melanin in melanosomes (Hoashi et al., *J. Biol. Chem.* 280:14006-14016, 2005; Valencia et al., *J Cell Sci* in press, 2006). rhDKK1 up-regulates the expression of caveolin 3, SVG2B, melanophilin and syntaxin 5A, which indicates that DKK1 regulates the subcellular trafficking of proteins either directly or indirectly. rhDKK1 also up-regulates the expression of MATP, a protein critical to the correct processing of tyrosinase (Costin et al., *J Cell Sci* 116: 3203-3212, 2003), thus the differentiation of melanocytes may be influenced by DKK1 at many levels.

rhDKK1 also affects the expression of numerous genes related with Wnt and HOX functions in melanocytes (see Tables 4 and 5, respectively). Thus, DKK1 could be an important regulator of those pathways considering their importance to melanocyte function (Bachmann et al., *Clin Cancer Res* 11: 8606-8614, 2005; Dunn et al., *Pigment Cell Res* 18: 167-180, 2005; Knight et al., *Devel Dynam* 229: 87-98, 2004; Takeda et al., *J Biol Chem* 275: 14013-14016, 2000). Further, rhDKK1 enhances the expression of acid fibroblast growth factor-like protein, which may function similar to fibroblast growth factor in terms of regulating HOX genes (Dasen et al., *Nature* 425:926-933, 2003; Liu et al., *Neuron*. 32(6):997-1012, 2001) and melanocyte growth (Berking et al., *Amer J Path* 158: 943-953, 2001; Dotto et al., *J Cell Biol* 109: 3115-3128, 1989; Halaban et al., *J Cell Biol* 107: 1611-1619, 1988; Hirobe, *Development* 114: 435-445, 1992).

To further explain the manner in which DKK1 decreases melanocyte function, key proteins in Wnt signaling pathways were investigated. The focus was on those genes since DKK1 is an inhibitor of the canonical Wnt signaling pathway (Kawano and Kypta, *J. Cell Sci.* 116:2627-2634, 2003), which is actively involved in regulating MITF function (Shibahara et al., *Pigment Cell Res* 13: 98-102, 2000; Yasumoto et al., *EMBO J* 21: 2703-2714, 2002). MITF is considered the master regulator of melanocyte function, and regulates not only melanocyte proliferation but also their production of melanin (Kim et al., *J Cell Sci* 116: 1699-1706, 2003; McGill et al., *Mech Devel* 87: 45-56, 2002). Hence the effect of DKK1 on Wnt signaling reveals its widespread effect on the development of pigmentation.

rhDKK1 suppresses the expression of β-catenin and MITF (Yamaguchi et al., *J. Cell Biol.* 165:275-285, 2004), and the overall expression of GSK3β decreases in response to rhDKK1, whereas that of GSK3β phosphorylated at Ser9 increases. GSK3β is a unique protein in that it is inactivated by phosphorylation (Cohen and Frame, *Nature Rev: Mol. Cell Biol.* 2:769-776, 2001). The finding that rhDKK1 inhibits β-catenin and GSK3β expression helps to explain the inhibitory effects of DKK1 on MITF expression since β-catenin and GSK3β enhance MITF activity at the promoter level (through the activation of LEF/TCF (Arias et al., *Curr Opin Genet Devel* 9: 447-454, 1999)) and at the post-transcriptional level (by the phosphorylation at Ser298 (Takeda et al., *Hum Mol Gen* 9: 125-132, 2000)). However, multiple protein complexes, which contain not only Axin, adenomatous polyposis coli and Akt, but also GSK3β (http://www.stanford.edu/~rnusse), suppress the expression of β-catenin by inhibiting its accumulation through the canonical Wnt signaling pathway (Cohen and Frame, *Nature Rev: Mol. Cell Biol.* 2:769-776, 2001; Kawano and Kypta, *J. Cell Sci.* 116:2627-2634, 2003; Zorn, *Curr Biol.* 11(15):R592-5, 2001). Since GSK3β is inactivated via several signaling pathways (Cohen and Frame, *Nature Rev: Mol. Cell Biol.* 2:769-776, 2001; Ding et al., *J Biol Chem* 275: 32475-32481, 2000) and since Wnt-5a inhibits the canonical Wnt pathway by promoting the GSK3β-independent degradation of β-catenin (Topol et al., *J. Cell Biol.* 162:899-908, 2003), the canonical Wnt signaling pathway does not require the phosphorylation of GSK3β at Ser9, but the non-canonical Wnt signaling pathway does involve that phosphorylated form of GSK3β.

Interestingly, there was an increase in β-catenin mRNA expression after only two hours of rhDKK1 treatment, but a decrease in β-catenin protein, which was followed by the decreased expression of β-catenin mRNA after five days of rhDKK1 treatment. The rapid decrease in expression of β-catenin protein after two hours of rhDKK1 treatment (Yamaguchi et al., *J. Cell Biol.* 165:275-285, 2004) might have transiently enhanced the mRNA expression level of β-catenin. Additionally, rhDKK1 enhances the expression of PKCα, which inactivates GSK3β (Chen et al., *J Biol Chem* 275: 17894-17899, 2000; Fang et al., *Mol. Cell. Biol.* 22:2099-2100, 2002) and induces apoptosis via p38 MAPK (Tanaka et al., *J Biol Chem* 278: 33753-33762, 2003; similar to Gadd45 as described above; Sarkar et al., *Proc Natl Acad Sci USA* 99: 10054-10059, 2002), which indicates that DKK1 may take its own pathway and/or the non-canonical Wnt signaling pathway to inhibit GSK3β. Taken together, the decreased activities of β-catenin and GSK3β via phosphorylation at Ser9 and the up-regulated expression of PKCα may account for the decreased expression levels of MITF in melanocytes responding to DKK1, and their decreased growth and differentiation, and a decrease in pigmentation.

In conclusion, DKK1, a secretory protein expressed at relatively high levels by fibroblasts in palmoplantar skin, has various depigmenting effects on melanocytes. Microarray analyses revealed a large number of up-regulated or down-regulated genes in melanocytes which respond quickly to treatment with rhDKK1. DKK1-responsive genes include those encoding receptors (such as LDLR, GPR51 and TNFSF10A), for apoptosis (such as Gadd45β), for melanosome trafficking and transport (such as HPS4, SV2B, STX5A and MLPH), and for Wnt and HOX signaling. The decreased expression levels of MITF in melanocytes treated with rhDKK1 may result from the decreased activity of β-catenin and of GSK3β via phosphorylation at Ser9 and from the up-regulated expression of PKCα. The sum of those activities results in the decreased density of melanocytes in palmoplantar skin and the hypopigmentation of that tissue.

EXAMPLE 6

Methods Used to Demonstrate Regulation of Skin Thickness

This Example illustrates the materials and methods used to demonstrate DKK1 regulation of skin thickness. DKK1 inhibits melanocyte growth and function via the suppression of β-catenin and microphthalmia-associated transcription factor (MITF; Yamaguchi et al., *J. Cell Biol.* 165:275-285, 2004). Since keratinocytes also play a major role in skin structure and pigmentation, the effects of DKK1 were also significant. The effects of DKK1 on melanin uptake by keratinocytes and on keratinocyte gene expression profiles and Wnt signaling pathways were measured to determine whether high levels of expression and secretion of DKK1 by palmoplantar fibroblasts accounts for the thick and hypopigmented phenotype of skin on the soles and the palms.

Keratinocyte and HaCaT Cell Cultures

Neonatal human foreskin keratinocytes were obtained from Cascade Biologics, Inc., Portland, Oreg. Keratinocyte cultures were grown in keratinocyte growth medium consisting of Medium 154 and HKGS (both from Cascade Biologics, Inc.). Keratinocytes from the third to fifth passage were used in these experiments. Immortalized human HaCaT keratinocytes (Boukamp et al., *J Cell Biol* 106:761-771, 1988) were used for melanin uptake experiments, and were cultured in 10% FBS/Dulbecco's modified Eagle medium (DME).

Reconstructed Skin

The epidermal equivalent MelanoDerm® was obtained from MatTek Corp (Ashland, Mass., USA). Normal human keratinocytes and melanocytes were obtained from Asian neonatal foreskin tissues. MelanoDerms were grown at the air/liquid interface of the maintenance medium MEL-NHM-113 (MatTek Corp.), and the culture medium was renewed every two days. Where noted, the epidermis samples were supplemented with 100 ng/ml rhDKK1 (R&D Systems, Minneapolis, Minn., USA) every two days for 4 to 10 days. rhDDK1 was dissolved in PBS with 0.1% BSA. The same concentrations of PBS and BSA were employed for mock-treated controls.

Histochemistry

Skin specimens were obtained from palmoplantar areas (palms and soles) and from non-palmoplantar areas (trunk) and were taken from 5 adult Asian subjects (ages ranged from 31 to 47) during cutaneous surgery. Skin and epidermal equivalent samples were embedded in paraffin and sections were cut using standard techniques. The sections were deparaffinized in xylene and hydrated through a series of graded ethanols. Specimens were observed following haematoxylin-eosin staining, Fontana-Masson staining and immunohistochemistry. The thickness of epidermis and more specifically the thickness of the stratum corneum was measured with Scion Image Software (Scion Corp, Frederick, Md., USA). Melanin content was measured after Fontana-Masson staining and was also analyzed by Scion Image Software (Scion Corp). The expression of protein was detected by indirect immunofluorescence using primary antibodies as follows. Mouse monoclonal antibody against keratin 9 (1:20, Abcam, Cambridge, Mass., USA), rabbit polyclonal against β-catenin (1:50, Cell Signaling, Danvers, Mass., USA) and rabbit polyclonal against PAR2 (1:1,000; Scott et al., *J. Invest. Dermatol.* 117:1412-14202001). Secondary antibodies used were Alexa Fluor 594 goat anti-mouse IgG (H+L), Alexa Fluor 488 goat anti-mouse IgG (H+L) and Alexa Fluor 488 goat anti-rabbit IgG (H+L). DAPI (Vector, Burlingame, Calif., USA) was used as a counter-stain. Fluorescence was observed and captured using a Leica DMR B/D MLD fluorescence microscope (Leica, Wetzlar, Germany) and a Dage-MTI 3CCD 3-chip color video camera (Dage-MTI, Michigan City, Ind.).

Transfection and Melanin Uptake

Transfection studies were performed using a DKK1 expressing plasmid, pcDNA3.1(−)-DKK1 (Yamaguchi et al., *J. Cell Biol.* 165:275-285, 2004), and the pcDNA3.1 vector alone as the control. Transfection was performed using lipofection for keratinocytes using lipofectamine 2000 (Invitrogen, Carlsbad, Calif.) according to the manufacturer's instructions. Keratinocytes were seeded at 60% confluence 16 hours prior to transfection in KGM or in 10% FBS/DME. The amount of DNA used for each transfection was 2 μg per $1\times10^6$ cells. After 5 days, transfected cells were harvested for various analyses including melanin uptake assay, immunocytochemistry and western blotting. The transfection efficiency was 70% as determined by the pEGFP-C1 vector (BD Biosciences Clontech, Palo Alto, Calif.) and/or a β-Gal staining kit (Invitrogen). Melanin granules (2 μg/ml) purified from MNT1 melanoma cells (Kushimoto et al., *Proc. Natl. Acad. Sci. USA* 98:10698-10703, 2001) was added 1 d before the harvest.

Microarray Procedures

Modified oligo-DNA microarray analysis was performed as previously described (Yamaguchi et al., *J. Cell Biol.* 165:275-285, 2004). Briefly, total RNA was prepared from cultured human keratinocytes treated with or without 50 ng/ml rhDKK1 (R&D Systems, Minneapolis, Minn.) for 2 hours, using an RNeasy mini kit (Qiagen, Valencia, Calif.). The quality (purity and integrity) of extracted total RNA was confirmed using an Agilent 2100 Bioanalyzer with an RNA 6000 Nano Assay (Agilent Technology, Palo Alto, Calif.). Paired cDNA samples, labeled by cyanine 3- and cyanine 5-dUTP incorporation (Qiagen) during reverse transcription (Qiagen), were hybridized simultaneously with one oligo-DNA chip (Hs-Operon V2-vB2.2p13) as per NCI in-house protocol (available at http://mach1.nci.nih.gov/). Two fluorescent intensities of the oligo-DNA chip were scanned using a microarray scanner (GenePix 4000A; Axon Instruments, Inc., Sunnyvale, Calif.). Differential gene expression was profiled with Genepix 3.0 software and was analyzed by NCI Center for Information Technology (CIT) programs and databases. All experiments were performed in triplicate independently.

RT-PCR

To confirm the validity of oligo-DNA microarray results, RT-PCR was performed. The oligonucleotide primers for PCR were based on published mRNA sequences and were as follows: human KLEIP sense primer 5'-tggctgtgttaggagggttc-3' (SEQ ID NO: 19); KLEIP antisense primer 5'-ctactgccat-gagctgtcca-3' (SEQ ID NO: 20); human GJB6 sense primer 5'-ggcgaggagagaagaggaat-3' (SEQ ID NO: 21); GJB6 antisense primer 5'-caactctgccacgttaagca-3' (SEQ ID NO: 22); human Snrpn sense primer 5'-gttttgggtctggtgttgct-3' (SEQ ID NO: 23); Snrpn antisense primer 5'-gacctctaatgcctggtgga-3' (SEQ ID NO: 24); human BMP2IK sense primer 5'-cacgc-caactagcacaaaga-3' (SEQ ID NO: 25); BMP2IK antisense primer 5'-aattcgactggttgggactg-3' (SEQ ID NO: 26); MITF sense primer 5'-agagagcgagtgcccaggcatgaac-3' (SEQ ID NO: 15); MITF antisense primer 5'-tctttggccagtgctcttgcttcag-3' (SEQ ID NO: 16); human P4HA2 sense primer 5'-tgtcaaact-gacaccccgta-3' (SEQ ID NO: 27); P4HA2 antisense primer 5'-atttactcgggccacaacag-3' (SEQ ID NO: 28); human Tulp3 sense primer 5'-acaccgtggatactgcttcc-3' (SEQ ID NO: 29); Tulp3 antisense primer 5'-ccgatccattccccttttat-3' (SEQ ID NO: 30); human PAR2 sense primer 5'-tgctagcagcctctctctcc-3' (SEQ ID NO: 31); PAR2 antisense primer 5'-cttcaaggg-gaaccagatga-3' (SEQ ID NO: 32); GAPDH sense primer 5'-accacagtccatgccatcac-3' (SEQ ID NO: 17); GAPDH antisense primer 5'-tccaccaccctgttgctgta-3' (SEQ ID NO: 18). After denaturation at 94° C. for two minutes, PCR was performed for 30 cycles (30 seconds at 94° C., one minute at 56° C., one minute at 72° C.). All amplified products were sequence verified (Yamaguchi et al., J. Cell Biol. 165:275-285, 2004). Control reactions were performed in the absence of reverse transcriptase and were negative. Each experiment was repeated at least in triplicate independently.

Immunoblotting

Cultures from 100 mm dishes were solubilized in 500 µl extraction buffer containing 1% Nonidet P 40 (Calbiochem, San Diego, Calif.), 0.01% SDS, 0.1 M Tris:HCl, pH 7.2, and Protease Inhibitor cocktail (Roche, Mannheim, Germany). Protein concentrations of extracts were measured using the BCA protein assay kit (Pierce, Rockford, Ill.). Cell extracts (1 µg) were separated on 8-14% gradient SDS polyacrylamide gels (Invitrogen). After electrophoresis, proteins were transferred electrophoretically from the gels to Immobilon-P transfer membranes (Millipore, Bedford, Mass.). The filters were incubated in the presence of antibodies to PAR2 (at 1:1,000, Abcam, Cambridge, Mass.), KLEIP (at 1:1,000) (Hara et al., Mol. Biol. Cell 15:1172-1184, 2004), β-catenin (at 1:1,000, Cell Signaling Technology, Beverly, Mass.), GSK-3β (at 1:1,000, Cell Signaling Technology), pGSK-3β (at 1:1,000, Cell Signaling Technology), PKCα (at 1:10,000, Sigma, St. Louis, Mo.), PKCβ2 (at 1:10,000, Sigma), ERK1/2 (p44/42 MAP Kinase antibody) (at 1:1,000, Cell Signaling Technology), pERK1/2 (at 1:1,000, Cell Signaling Technology) or β-actin (at 1:3,000, AC-15, Abcam) at 23° C. for one hour. They were then washed and incubated with horseradish peroxidase-linked anti-rabbit or anti-mouse whole antibodies (at 1:1,000, Amersham) at room temperature for one hour. Antigens were detected using an ECL-plus Western Blotting Detection System (Amersham).

Immunocytochemical Staining

Keratinocyte cultures in two well Lab-Tek chamber slides (Nalge Nunc International Corp., Naperville, Ill.) were processed for indirect immunofluorescence to detect the expression of signal transduction proteins using primary antibodies to GSK-3β (1:50, Cell Signaling Technology), phospho-GSK-3β which is specific for GSK-3β phosphorylated at Ser9 (at 1:100, Cell Signaling Technology), β-catenin (at 1:50, Cell Signaling Technology and Santa Cruz, Santa Cruz, Calif.), PKCβ1 (at 1:1,000, Sigma), and PKCα (at 1:1,000, Sigma).

Bound antibodies were visualized with appropriate secondary antibodies, Alexa Fluor® 488 goat anti-rabbit IgG (H+L) (Molecular Probes, Inc., Eugene, Oreg.) and Alexa Fluor® 594 mouse anti-rabbit IgG (H+L) (Molecular Probes) at 37° C. for 30 minutes at 1:500 dilution with 5% goat serum. DAPI (Vector, Burlingame, Calif.) was used as a counterstain. The fluorescence of green produced by Alexa 488®, of red produced by Alexa 594®, and of blue by DAPI was observed and captured using a Leica DMR B/D MLD fluorescence microscope (Leica, Wetzlar, Germany) and a Dage-MTI 3CCD 3-chip color video camera (Dage-MTI, Michigan City, Ind.). Confocal microscopy was also used to investigate the localization, as detailed by (Hoashi et al., J. Biol. Chem. 280:14006-14016, 2005).

EXAMPLE 7

Figure 7:
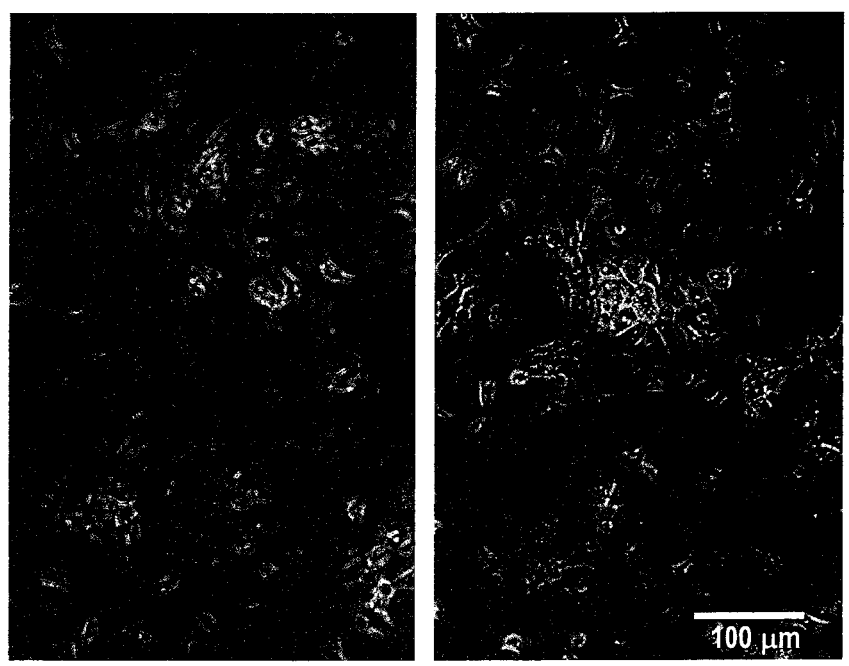
FIG. 7 is a set of digital images of cell cultures showing melanin uptake and proliferation of mock-transfected or DKK1-transfected keratinocytes in vitro. DKK1-transfected keratinocytes showed less melanin phagocytosis than mock-transfected controls (top, bright field microscopy), whereas the cell density was increased in DKK1-transfected cells (bottom, phase contrast microscopy). Cell numbers show the number of cells/field in a counting chamber while melanin content reflects analysis by ScionImage, as detailed below in Example 6. Numbers reported in all figures are means±SEM, and statistical analyses were performed using Student's t test (NS=not significant).

DKK1 Suppresses the Uptake of Melanin and Promotes Keratinocyte Growth and Density This Example demonstrates the effects of DKK1 on the proliferation of human keratinocytes and their uptake of melanin granules. HaCaT keratinocytes were mock-transfected or were transfected with DKK1, and their uptake of melanin granules purified from MNT1 melanoma cells was measured (FIG. 7). After incubation for 24 hours, keratinocytes transfected with DKK1 phagocytosed significantly less melanin than did those transfected with a control vector (FIG. 7). Further, transfection of DKK1 into normal human keratinocytes (FIG. 7) or treatment of those cells with recombinant human DKK1 (rhDKK1) similarly stimulated their growth and density, as recently reported for human mesenchymal stem cells (Gregory et al., J. Biol. Chem. 280:2309-2323, 2005).

Figure 8:
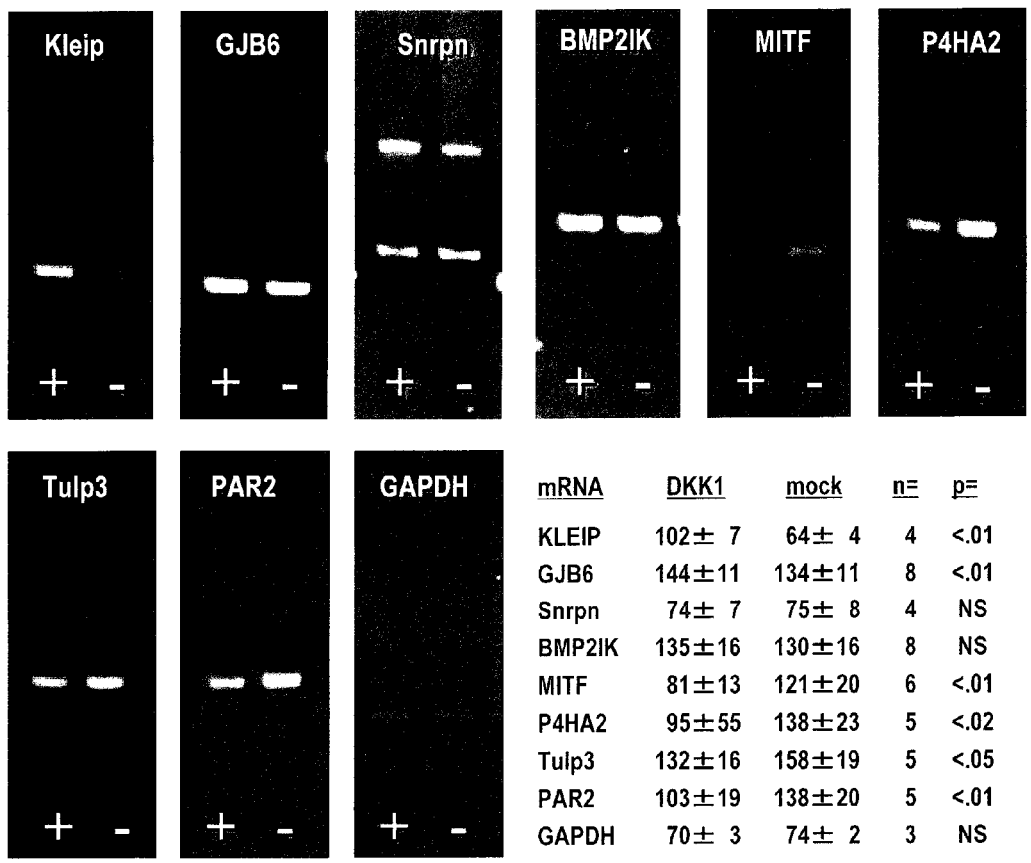
FIG. 8 is a set of digital images of gels showing mRNA levels in human keratinocytes treated (+) or untreated (−) with 50 ng/ml rhDKK1 for two hours as analyzed by RT-PCR. The expression of KLEIP and GJB6 was up-regulated by DKK1, but MITF, P4HA2, Tulp3 and PAR2 were down-regulated; densitometric analyses are reported at the bottom right of the figure. GAPDH is shown as a loading control.

To elucidate DKK1 suppression of the uptake of melanin and promotion of keratinocyte growth and density, human keratinocytes were stimulated with 50 ng/ml rhDKK1 for two hours, harvested total RNA from those cells and from untreated controls, and then analyzed those transcripts using oligonucleotide-DNA microarray technology. Up-regulated or down-regulated genes are summarized in Tables 7-11. Treatment of keratinocytes with DKK1 had varied effects on genes related to cell contraction, to apoptosis (TNFRSF1A-associated via death domain; TRADD), to non-canonical Wnt signaling pathways, to protein kinase Cβ1 (PKCβ1), to HOX transcription factors (HoxD8 and 12) and to keratins (keratin 9). The differences in mRNA expression levels of interesting genes were confirmed using RT-PCR, which validated that levels of some genes (such as Kelch-like ECT2 interacting protein (KLEIP) and connexin 30 (gap junction protein, β6; GJB6)) were up-regulated in response to DKK1 treatment, whereas DKK1 down-regulated the expression levels of other genes (such as MITF, procollagen-proline, 2-oxoglutarate 4-dioxygenase (P4HA2), Tubby like protein 3 (Tulp3) and proteinase-activated receptor-2 (PAR2; coagulation factor II receptor-like 1; thrombin receptor-like 1)) (FIG. 8). Although Snrpn expression was one of the top 30 genes up-regulated by DKK1, that was not confirmed by RT-PCR; in addition, no change was detected in BMP2IK (GAPDH serves as a loading control).

TABLE 7

| DKK1/NS | DKK1 | NS | Gene | Description |
|---|---|---|---|---|
| Top 30 genes up-regulated genes by 2-hour treatment with DKK1* | | | | |
| 9.54 | 4531 | 475 | SUHW4 | suppressor of hairy wing homolog 4 (Drosophila) (SUHW4), transcript variant 2, mRNA. |
| 8.50 | 7572 | 890 | C14orf1 | chromosome 14 open reading frame 1 (C14orf1), mRNA. |
| 8.12 | 5994 | 739 | PCSK4 | proprotein convertase subtilisin/kexin type 4 (PCSK4), mRNA. |
| 7.61 | 7126 | 937 | EPHA5 | EphA5 (EPHA5), transcript variant 2, mRNA. |
| 6.00 | 3141 | 524 | NRXN1 | neurexin 1 (NRXN1), transcript variant β, mRNA. |

TABLE 7-continued

| DKK1/NS | DKK1 | NS | Gene | Description |
|---|---|---|---|---|
| 5.85 | 8444 | 1443 | DGKH | Diacylglycerol kinase, eta |
| 5.55 | 8480 | 1527 | ZNF91 | zinc finger protein 91 (HPF7, HTF10) (ZNF91), mRNA. |
| 5.31 | 2536 | 478 | RORB | RAR-related orphan receptor B (RORB), mRNA. |
| 4.58 | 5080 | 1108 | GRIA1 | Glutamate receptor, ionotropic, AMPA 1 |
| 4.21 | 4162 | 989 | CDCA2 | cell division cycle associated 2 (CDCA2), mRNA. |
| 3.94 | 3148 | 799 | ECEL1 | endothelin converting enzyme-like 1 (ECEL1), mRNA. |
| 3.69 | 5276 | 1432 | FOXG1B | forkhead box G1B (FOXG1B), mRNA. |
| 3.53 | 2212 | 626 | KLEIP | Kelch-like ECT2 interacting protein |
| 3.35 | 22237 | 6646 | DNAJC10 | DnaJ (Hsp40) homolog, subfamily C, member 10 (DNAJC10), mRNA. |
| 3.32 | 3430 | 1033 | TRHR | thyrotropin-releasing hormone receptor (TRHR), mRNA. |
| 3.25 | 2129 | 655 | WISP2 | WNT1 inducible signaling pathway protein 2 (WISP2), mRNA. |
| 3.23 | 2793 | 865 | FBXO31 | F-box protein 31 |
| 3.13 | 3182 | 1016 | GABRR1 | γ-aminobutyric acid (GABA) receptor, rho 1 (GABRR1), mRNA. |
| 3.08 | 5150 | 1670 | ART3 | ADP-ribosyltransferase 3 (ART3), mRNA. |
| 3.06 | 2150 | 703 | SNRPN | SNRPN upstream reading frame |
| 3.04 | 2681 | 881 | GTDC1 | glycosyltransferase-like 1 (GTDC1), mRNA. |
| 3.01 | 5032 | 1669 | CACNG2 | Calcium channel, voltage-dependent, γ subunit 2 |
| 3.01 | 3631 | 1207 | DBH | dopamine β-hydroxylase (dopamine β-monooxygenase) (DBH), mRNA. |
| 3.01 | 2292 | 763 | SLC24A3 | solute carrier family 24 (sodium/potassium/calcium exchanger), member 3 (SLC24A3), mRNA. |
| 2.97 | 2378 | 800 | PRKCB1 | protein kinase C, β1 (PRKCB1), transcript variant 1, mRNA. |
| 2.88 | 3698 | 1282 | PRSS35 | protease, serine, 35 (PRSS35), mRNA. |
| 2.81 | 2329 | 829 | RAB39B | RAB39B, member RAS oncogene family (RAB39B), mRNA. |
| 2.80 | 3579 | 1280 | ADRB3 | adrenergic, β-3-, receptor (ADRB3), mRNA |
| 2.71 | 8381 | 3091 | SENP6 | SUMO1/sentrin specific protease 6 (SENP6), mRNA. |
| 2.71 | 4710 | 1741 | NR2C2 | nuclear receptor subfamily 2, group C, member 2 (NR2C2), mRNA. |
| Top 30 genes Down-regulated genes by 2-hour treatment with DKK1** | | | | |
| 0.04 | 715 | 19559 | CSPG3 | chondroitin sulfate proteoglycan 3 (neurocan) (CSPG3), mRNA. |
| 0.06 | 1094 | 19633 | TULP3 | Tubby like protein 3 |
| 0.12 | 3026 | 25078 | LRMP | lymphoid-restricted membrane protein (LRMP), mRNA. |
| 0.14 | 2930 | 21426 | CNTNAP2 | contactin associated protein-like 2 (CNTNAP2), mRNA. |
| 0.15 | 3559 | 23856 | COL3A1 | collagen, type III, α1 (Ehlers-Danlos syndrome type IV, autosomal dominant) (COL3A1), mRNA. |
| 0.17 | 1633 | 9732 | GNAT1 | Guanine nucleotide binding protein (G protein), α transducing activity polypeptide 1 |
| 0.17 | 6119 | 35544 | TRADD | TNFRSF1A-associated via death domain (TRADD), transcript variant 1, mRNA. |
| 0.19 | 8435 | 44668 | | Anti-streptococcal/anti-myosin immunoglobulin kappa light chain variable region |
| 0.23 | 13976 | 60058 | P4HA2 | procollagen-proline, 2-oxoglutarate 4-dioxygenase (proline 4-hydroxylase), α polypeptide II (P4HA2), mRNA. |
| 0.27 | 2929 | 10666 | IRS4 | insulin receptor substrate 4 (IRS4), mRNA. |
| 0.29 | 5207 | 18020 | MAPK9 | mitogen-activated protein kinase 9 (MAPK9), transcript variant 2, mRNA. |
| 0.29 | 14354 | 49168 | PTCH2 | patched homolog 2 (*Drosophila*) (PTCH2), mRNA. |
| 0.32 | 7783 | 24293 | PDXP | pyridoxal (pyridoxine, vitamin B6) phosphatase (PDXP), mRNA. |
| 0.33 | 6206 | 18788 | hSyn | brain synembryn (hSyn), mRNA. |
| 0.35 | 1920 | 5551 | TARSH | target of Nesh-SH3 (TARSH), mRNA. |
| 0.35 | 9646 | 27748 | MAN1C1 | mannosidase, α, class 1C, member 1 (MAN1C1), mRNA. |
| 0.35 | 18040 | 51769 | RAB25 | RAB25, member RAS oncogene family (RAB25), mRNA. |
| 0.35 | 1109 | 3133 | GAD1 | glutamate decarboxylase 1 (brain, 67 kDa) (GAD1), transcript variant GAD67, mRNA. |
| 0.36 | 12314 | 34502 | SERPINH1 | serine (or cysteine) proteinase inhibitor, clade H (HSP 47), member 1, (collagen binding protein 1) (SERPINH1), mRNA. |
| 0.36 | 1973 | 5455 | RPS4X | Ribosomal protein S4, X-linked |
| 0.36 | 15682 | 43145 | RPS4Y1 | ribosomal protein S4, Y-linked 1 (RPS4Y1), mRNA. |
| 0.37 | 22985 | 62579 | RHOBTB2 | Rho-related BTB domain containing 2 (RHOBTB2), mRNA. |
| 0.37 | 16119 | 43756 | MITF | microphthalmia-associated transcription factor (MITF), transcript variant 5, mRNA. |
| 0.38 | 4534 | 12021 | KISS1 | KiSS-1 metastasis-suppressor (KISS1), mRNA. |
| 0.38 | 772 | 2021 | ACTL6B | actin-like 6B (ACTL6B), mRNA. |
| 0.39 | 4267 | 11042 | PHLDB3 | Pleckstrin homology-like domain, family B, member 3 |
| 0.39 | 18262 | 46894 | XPA | xeroderma pigmentosum, complementation group A (XPA), mRNA. |
| 0.39 | 4619 | 11830 | GTF2A1 | General transcription factor IIA, 1, 19/37 kDa |
| 0.39 | 6012 | 15390 | UMP-CMPK | UMP-CMP kinase (UMP-CMPK), mRNA. |
| 0.39 | 1696 | 4327 | JRKL | jerky homolog-like (mouse) (JRKL), mRNA. |

*Genes listed are those whose expression levels in DKK1-treated keratinocytes were >2,000 (65,000 is the maximum) after 2 hr treatment with DKK1; data are reported as means of 3 independent experiments
**Genes listed are those whose expression levels in mock-treated keratinocytes were >2,000 (65,000 is the maximum) after 2 hr treatment with DKK1; data are reported as means of 3 independent experiments.

TABLE 8

| DKK1/NS | DKK1 | NS | Gene | Description |
|---|---|---|---|---|
| \multicolumn{5}{c}{Receptor-Related Genes Up-regulated by Treatment with DKK1 for 2 hr*} |||||

| DKK1/NS | DKK1 | NS | Gene | Description |
|---|---|---|---|---|
| 5.31 | 2536 | 478 | RORB | RAR-related orphan receptor B (RORB), mRNA. |
| 4.58 | 5080 | 1108 | GRIA1 | Glutamate receptor, ionotropic, AMPA 1 |
| 3.32 | 3430 | 1033 | TRHR | thyrotropin-releasing hormone receptor (TRHR), mRNA. |
| 3.13 | 3182 | 1016 | GABRR1 | γ-aminobutyric acid (GABA) receptor, rho 1 (GABRR1), mRNA. |
| 2.80 | 3579 | 1280 | ADRB3 | adrenergic, β-3-, receptor (ADRB3), mRNA. |
| 2.75 | 2076 | 755 | EPHA6 | EPH receptor A6 |
| 2.71 | 4710 | 1741 | NR2C2 | nuclear receptor subfamily 2, group C, member 2 (NR2C2), mRNA. |
| 2.61 | 2495 | 956 | FCER1A | Fc fragment of IgE, high affinity I, receptor for; α polypeptide |
| 2.60 | 40698 | 15632 | SORL1 | sortilin-related receptor, L(DLR class) A repeats-containing (SORL1), mRNA. |
| 2.47 | 2291 | 926 | PTGER3 | Prostaglandin E receptor 3 (subtype EP3) |
| 2.45 | 2034 | 829 | TNFRSF17 | tumor necrosis factor receptor superfamily, member 17 (TNFRSF17), mRNA. |
| 2.40 | 1166 | 486 | GRIN3A | glutamate receptor, ionotropic, N-methyl-D-aspartate 3A (GRIN3A), mRNA. |
| 2.37 | 4562 | 1921 | P2RY1 | purinergic receptor P2Y, G-protein coupled, 1 (P2RY1), mRNA. |
| 2.36 | 1715 | 726 | PPFIA2 | protein tyrosine phosphatase, receptor type, f polypeptide (PTPRF), interacting protein (liprin), α2 (PPFIA2), mRNA. |
| 2.35 | 1041 | 443 | ITGA4 | integrin, α4 (antigen CD49D, α4 subunit of VLA-4 receptor) (ITGA4), mRNA. |
| 2.35 | 3671 | 1565 | NCR2 | natural cytotoxicity triggering receptor 2 (NCR2), mRNA. |
| 2.33 | 1397 | 599 | CHRM3 | Cholinergic receptor, muscarinic 3 |
| 2.21 | 3113 | 1412 | GPR37 | G protein-coupled receptor 37 (endothelin receptor type B-like) (GPR37), mRNA. |
| 2.20 | 4655 | 2113 | VPS16 | Protein tyrosine phosphatase, receptor type, A |
| 2.20 | 1990 | 904 | LRP4 | Low density lipoprotein receptor-related protein 4 |
| 2.19 | 2528 | 1155 | PTPRK | Protein tyrosine phosphatase, receptor type, K |
| 2.19 | 1702 | 778 | PTPRK | Protein tyrosine phosphatase, receptor type, K |
| 2.17 | 1147 | 530 | NR2E1 | nuclear receptor subfamily 2, group E, member 1 (NR2E1), mRNA. |
| 2.12 | 2743 | 1297 | P2RY10 | purinergic receptor P2Y, G-protein coupled, 10 (P2RY10), transcript variant 2, mRNA. |
| 2.11 | 1195 | 567 | TFR2 | transferrin receptor 2 (TFR2), mRNA. |
| 2.11 | 2486 | 1181 | NR3C2 | nuclear receptor subfamily 3, group C, member 2 (NR3C2), mRNA. |
| 2.10 | 1337 | 635 | EDG6 | endothelial differentiation, G-protein-coupled receptor 6 (EDG6), mRNA. |
| 2.10 | 1907 | 908 | TRPM8 | transient receptor potential cation channel, subfamily M, member 8 (TRPM8), mRNA. |
| 2.06 | 3880 | 1885 | ILT7 | leukocyte immunoglobulin-like receptor, subfamily A (without TM domain), member 4 (ILT7), mRNA. |
| 2.05 | 2298 | 1120 | PVRL3 | Poliovirus receptor-related 3 |
| 2.05 | 1219 | 595 | NR4A2 | nuclear receptor subfamily 4, group A, member 2 (NR4A2), transcript variant 4, mRNA. |
| 2.04 | 3027 | 1486 | HRH3 | histamine receptor H3 (HRH3), mRNA. |
| 2.04 | 1975 | 970 | GPR23 | G protein-coupled receptor 23 (GPR23), mRNA |
| 2.00 | 1075 | 537 | ADRB1 | adrenergic, β-1-, receptor |
| 2.00 | 11326 | 5670 | MST1R | macrophage stimulating 1 receptor (c-met-related tyrosine kinase) (MST1R), mRNA |
| \multicolumn{5}{c}{Receptor-Related Genes Down-regulated by Treatment with DKK1 for 2 hr**} |||||
| 0.16 | 321 | 1976 | GRIN3A | glutamate receptor, ionotropic, N-methyl-D-aspartate 3A (GRIN3A), mRNA. |
| 0.17 | 6119 | 35544 | TRADD | TNFRSF1A-associated via death domain (TRADD), transcript variant 1, mRNA. |
| 0.18 | 182 | 1000 | OR12D3 | olfactory receptor, family 12, subfamily D, member 3 (OR12D3), mRNA. |
| 0.24 | 343 | 1432 | IL10RA | interleukin 10 receptor, α (IL10RA), mRNA. |
| 0.27 | 2929 | 10666 | IRS4 | insulin receptor substrate 4 (IRS4), mRNA. |
| 0.35 | 602 | 1701 | GRM6 | glutamate receptor, metabotropic 6 (GRM6), mRNA. |
| 0.36 | 551 | 1520 | GRK4 | G protein-coupled receptor kinase 4 |
| 0.36 | 719 | 1978 | MS4A2 | membrane-spanning 4-domains, subfamily A, member 2 (Fc fragment of IgE, high affinity I, receptor for β polypeptide) (MS4A2) mRNA. |
| 0.40 | 640 | 1592 | LOC219347 | Similar to nuclear DNA-binding protein; small unique nuclear receptor corepressor; C1D DNA-binding protein |
| 0.41 | 439 | 1075 | GPR116 | G protein-coupled receptor 116 (GPR116), mRNA. |
| 0.42 | 1959 | 4652 | PTPRS | protein tyrosine phosphatase, receptor type, S (PTPRS), transcript variant 3, mRNA. |
| 0.43 | 4032 | 9335 | LTBR | lymphotoxin β receptor (TNFR superfamily, member 3) (LTBR), mRNA. |

TABLE 8-continued

| DKK1/NS | DKK1 | NS | Gene | Description |
|---|---|---|---|---|
| 0.45 | 662 | 1486 | AGTR2 | angiotensin II receptor, type 2 (AGTR2), mRNA. |
| 0.45 | 757 | 1691 | GNRHR | Gonadotropin-releasing hormone receptor (GNRHR), mRNA. |
| 0.47 | 1568 | 3312 | OR5V1 | olfactory receptor, family 5, subfamily V, member 1 (OR5V1), mRNA. |
| 0.48 | 4914 | 10334 | ANTXR2 | anthrax toxin receptor 2 (ANTXR2), mRNA. |

*Genes listed are those whose expression levels in DKK1-treated keratinocytes were >1,000 (65,000 is the maximum) after 2 hr treatment with DKK1; data for genes with DKK1/NS ratio >2.00 are reported as means of 3 independent experiments.
KREMEN1(kringle containing transmembrane protein 1), transcript variant 2, was 3.5-797-227.

**Genes listed are those whose expression levels in mock-treated keratinocytes were >1,000 (65,000 is the maximum) after 2 hr treatment with DKK1; data for genes with DKK1/NS ratio <0.50 are reported as means of 3 independent experiments.

TABLE 9

| DKK1/NS | DKK1 | NS | Gene | Description |
|---|---|---|---|---|
| | | | | Wnt-Related Genes Up-regulated by Treatment with DKK1 for 2 hr* |
| 3.60 | 1449 | 403 | APC2 | adenomatosis polyposis coli 2 (APC2), mRNA. |
| 3.51 | 797 | 227 | KREMEN1 | kringle containing transmembrane protein 1 (KREMEN1), transcript variant 2, mRNA. |
| 3.25 | 2129 | 655 | WISP2 | WNT1 inducible signaling pathway protein 2 (WISP2), mRNA. |
| 2.97 | 2378 | 800 | PRKCB1 | protein kinase C, β1 (PRKCB1), transcript variant 1, mRNA. |
| 2.56 | 1696 | 664 | PPP2R2B | Protein phosphatase 2 (formerly 2A), regulatory subunit B (PR 52), β isoform |
| 2.50 | 1081 | 431 | NFATC2 | Nuclear factor of activated T-cells, cytoplasmic, calcineurin-dependent 2 |
| 2.21 | 3811 | 1721 | PRKCH | Protein kinase C, eta |
| 1.76 | 1849 | 1048 | WNT9B | wingless-type MMTV integration site family, member 9B (WNT9B), mRNA. |
| 1.74 | 1384 | 797 | PRKCG | protein kinase C, γ (PRKCG), mRNA. |
| 1.70 | 2116 | 1245 | SFRP4 | secreted frizzled-related protein 4 (SFRP4), mRNA. |
| 1.65 | 7275 | 4397 | WISP1 | WNT1 inducible signaling pathway protein 1 (WISP1), transcript variant 1, mRNA. |
| | | | | Wnt-Related Genes Down-regulated by Treatment with DKK1 for 2 hr** |
| 1.65 | 1826 | 1105 | FRAT1 | frequently rearranged in advanced T-cell lymphomas (FRAT1), transcript variant 1, mRNA. |
| 1.64 | 6852 | 4184 | DVL2 | dishevelled, dsh homolog 2 (Drosophila) (DVL2), mRNA. |
| 1.61 | 2132 | 1321 | PRKCA | protein kinase C, α (PRKCA), mRNA. |
| 1.60 | 10952 | 6829 | DAAM1 | Dishevelled associated activator of morphogenesis 1 |
| 1.59 | 2605 | 1642 | EP300 | E1A binding protein p300 (EP300), mRNA. |
| 1.58 | 8442 | 5334 | SMAD2 | SMAD, mothers against DPP homolog 2 (Drosophila) (SMAD2), transcript variant 1, mRNA. |
| 1.57 | 7039 | 4474 | PPP3CB | protein phosphatase 3 (formerly 2B), catalytic subunit, β isoform (calcineurin A β) (PPP3CB), mRNA. |
| 1.57 | 1787 | 1139 | TCF7 | transcription factor 7 (T-cell specific, HMG-box) (TCF7), transcript variant 2, mRNA. |
| 1.54 | 1412 | 915 | SIP | Siah-interacting protein (SIP), mRNA. |
| 1.53 | 5306 | 3469 | PRKCH | protein kinase C, eta (PRKCH), mRNA. |
| 1.45 | 2468 | 1706 | TCF7L2 | transcription factor 7-like 2 (T-cell specific, HMG-box) (TCF7L2), mRNA. |
| 0.29 | 5207 | 18020 | MAPK9 | mitogen-activated protein kinase 9 (MAPK9), transcript variant 2, mRNA. |
| 0.41 | 861 | 2098 | PRKACB | protein kinase, cAMP-dependent, catalytic, β (PRKACB), transcript variant 3, mRNA. |
| 0.46 | 514 | 1114 | CAMK2A | calcium/calmodulin-dependent protein kinase (CaM kinase) II α (CAMK2A), transcript variant 2, mRNA. |
| 0.46 | 1153 | 2491 | NFATC3 | nuclear factor of activated T-cells, cytoplasmic, calcineurin-dependent 3 (NFATC3), transcript variant 2, mRNA. |
| 0.48 | 813 | 1700 | TBL1X | transducin (β)-like 1X-linked (TBL1X), mRNA. |
| 0.52 | 4010 | 7706 | CSNK1G2 | Casein kinase 1, γ2 (CSNK1G2), mRNA. |
| 0.54 | 787 | 1454 | SFRP5 | secreted frizzled-related protein 5 (SFRP5), mRNA. |
| 0.55 | 689 | 1257 | WNT2 | wingless-type MMTV integration site family member 2 (WNT2), mRNA. |
| 0.55 | 1411 | 2570 | NFATC1 | nuclear factor of activated T-cells, cytoplasmic, calcineurin-dependent 1 (NFATC1), transcript variant 4, mRNA. |
| 0.57 | 12420 | 21611 | CSNK1A1 | Casein kinase 1, α1 (CSNK1A1), mRNA. |
| 0.58 | 2849 | 4888 | PPARD | peroxisome proliferative activated receptor, δ (PPARD), transcript variant 1, mRNA. |
| 0.59 | 640 | 1091 | WNT1 | wingless-type MMTV integration site family, member 1 (WNT1), mRNA. |
| 0.60 | 635 | 1051 | NFATC2 | nuclear factor of activated T-cells, cytoplasmic, calcineurin-dependent 2 (NFATC2), transcript variant 1, mRNA. |

TABLE 9-continued

| DKK1/NS | DKK1 | NS | Gene | Description |
|---|---|---|---|---|
| 0.61 | 2908 | 4791 | TLE1 | Transducin-like enhancer of split 1 (E(sp1) homolog, *Drosophila*) |
| 0.61 | 5749 | 9400 | SHFM3 | Split hand/foot malformation (ectrodactyly) type 3 |
| 0.62 | 8840 | 14278 | SKP1A | S-phase kinase-associated protein 1A (p19A) (SKP1A), transcript variant 2, mRNA. |
| 0.62 | 18626 | 29873 | DKK1 | dickkopf homolog 1 (*Xenopus laevis*) (DKK1), mRNA. |
| 0.63 | 650 | 1035 | SMAD3 | SMAD, mothers against DPP homolog 3 (*Drosophila*) |
| 0.63 | 662 | 1051 | SKP1A | S-phase kinase-associated protein 1A (p19A) (SKP1A), transcript variant 1, mRNA. |
| 0.63 | 920 | 1459 | SHFM3 | Split hand/foot malformation (ectrodactyly) type 3 |
| 0.64 | 1463 | 2296 | CAMK2B | calcium/calmodulin-dependent protein kinase (CaM kinase) II β (CAMK2B), transcript variant 8, mRNA. |
| 0.65 | 1129 | 1739 | PRKACB | protein kinase, cAMP-dependent, catalytic, β (PRKACB), transcript variant 1, mRNA. |
| 0.65 | 17207 | 26320 | RBX1 | ring-box 1 (RBX1), mRNA. |
| 0.66 | 832 | 1253 | PRKCE | Protein kinase C, epsilon |
| 0.67 | 19582 | 29362 | PRICKLE1 | prickle-like 1 (*Drosophila*) (PRICKLE1), mRNA. |
| 0.67 | 23176 | 34546 | YY1 | YY1 transcription factor (YY1), mRNA. |
| 0.67 | 29791 | 44369 | AES | Amino-terminal enhancer of split |
| 0.68 | 4418 | 6542 | AXIN1 | axin 1 (AXIN1), transcript variant 2, mRNA. |
| 0.68 | 7298 | 10757 | SLC9A3R1 | Solute carrier family 9 (sodium/hydrogen exchanger), isoform 3 regulator 1 (SLC9A3R1), mRNA. |
| 0.68 | 7036 | 10320 | TBL1XR1 | transducin (β)-like 1X-linked receptor 1 (TBL1XR1), mRNA. |
| 0.68 | 8962 | 13140 | RUVBL1 | RuvB-like 1 (*E. coli*) (RUVBL1), mRNA. |
| 0.68 | 3428 | 5024 | JUN | v-jun sarcoma virus 17 oncogene homolog (avian) (JUN), mRNA. |
| 0.69 | 2743 | 3989 | PKN2 | protein kinase N2 (PKN2), mRNA. |
| 0.69 | 14324 | 20809 | CSNK1D | Casein kinase 1, δ (CSNK1D), transcript variant 1, mRNA. |
| 0.70 | 2005 | 2879 | PYGO2 | pygopus 2 (PYGO2), mRNA. |
| 0.70 | 6558 | 9373 | NOTCH1 | Notch homolog 1, translocation-associated (*Drosophila*) (NOTCH1), mRNA. |
| 0.70 | 2357 | 3365 | SOX17 | SRY (sex determining region Y)-box 17 (SOX17), mRNA. |

*Genes listed are those whose expression levels in mock-treated keratinocytes were >1,000 (65,000 is the maximum) after 2 hr treatment with DKK1; data for genes with DKK1/NS ratio <0.70 are reported as means of 3 independent experiments.
**Genes listed are those whose expression levels in mock-treated keratinocytes were >1,000 (65,000 is the maximum) after 2 hr treatment with DKK1; data for genes with DKK1/NS ratio <0.70 are reported as means of 3 independent experiments.

TABLE 10

| DKK1/NS | DKK1 | NS | Gene | Description |
|---|---|---|---|---|
| | | | | HOX-Related Genes Up-regulated by Treatment with DKK1 for 2 hr* |
| 3.49 | 1986 | 569 | DLX6 | PREDICTED: *Homo sapiens* distal-less homeo box 6 (DLX6), mRNA. |
| 3.04 | 325 | 107 | SHOX | short stature homeobox (SHOX), transcript variant SHOXa, mRNA. |
| 2.62 | 1520 | 580 | HOXB13 | homeo box B13 (HOXB13), mRNA. |
| 2.37 | 2125 | 895 | LOC135935 | PREDICTED: *Homo sapiens* similar to OG-2 homeodomain protein-like; similar to U65067 (PID: g1575526) (LOC135935), mRNA. |
| 1.94 | 5511 | 2836 | PROX1 | prospero-related homeobox 1 (PROX1), mRNA. |
| 1.74 | 5145 | 2961 | PITX2 | paired-like homeodomain transcription factor 2 (PITX2), transcript variant 1, mRNA. |
| 1.72 | 1578 | 915 | HOXB1 | homeo box B1 (HOXB1), mRNA. |
| 1.70 | 2776 | 1636 | HOXB9 | homeo box B9 (HOXB9), mRNA. |
| 1.67 | 15659 | 9358 | LHX6 | LIM homeobox 6 (LHX6), transcript variant 2, mRNA. |
| 1.67 | 1605 | 962 | HOXC4 | homeo box C4 (HOXC4), transcript variant 1, mRNA. |
| 1.65 | 1635 | 990 | GBX2 | gastrulation brain homeo box 2 (GBX2), mRNA. |
| 1.62 | 1341 | 827 | HOXA13 | homeo box A13 (HOXA13), mRNA. |
| 1.54 | 1231 | 799 | CART1 | cartilage paired-class homeoprotein 1 (CART1), mRNA. |
| 1.52 | 4364 | 2873 | HOXA4 | homeo box A4 (HOXA4), mRNA. |
| 1.50 | 2705 | 1805 | HLXB9 | homeo box HB9 (HLXB9), mRNA. |
| 1.48 | 1585 | 1074 | CDX4 | caudal type homeo box transcription factor 4 (CDX4), mRNA. |
| 1.47 | 7675 | 5218 | PKNOX1 | PBX/knotted 1 homeobox 1 (PKNOX1), transcript variant 1, mRNA. |
| | | | | HOX-Related Genes Down-regulated by Treatment with DKK1 for 2 hr** |
| 0.35 | 406 | 1171 | BAPX1 | bagpipe homeobox homolog 1 (*Drosophila*) (BAPX1), mRNA. |
| 0.42 | 1044 | 2501 | HOXC5 | homeo box C5 (HOXC5), mRNA. |
| 0.48 | 4480 | 9420 | PHC2 | polyhomeotic-like 2 (*Drosophila*) (PHC2), transcript variant 2, mRNA. |
| 0.48 | 856 | 1785 | LMX1B | LIM homeobox transcription factor 1, β (LMX1B), mRNA. |
| 0.48 | 1033 | 2152 | HOXB8 | homeo box B8 (HOXB8), mRNA. |
| 0.50 | 1086 | 2163 | HMX1 | homeo box (H6 family) 1 (HMX1), mRNA. |
| 0.53 | 6110 | 11499 | PKNOX2 | PBX/knotted 1 homeobox 2 (PKNOX2), mRNA. |
| 0.53 | 1030 | 1938 | BARX2 | BarH-like homeobox 2 (BARX2), mRNA. |
| 0.55 | 3371 | 6164 | ZFHX1B | zinc finger homeobox 1b (ZFHX1B), mRNA. |
| 0.55 | 1137 | 2052 | HOXD8 | homeo box D8 (HOXD8), mRNA. |
| 0.56 | 4305 | 7660 | HOXA9 | homeo box A9 (HOXA9), transcript variant 2, mRNA. |
| 0.57 | 818 | 1442 | DUX1 | double homeobox, 1 (DUX1), mRNA. |

TABLE 10-continued

| DKK1/NS | DKK1 | NS | Gene | Description |
|---|---|---|---|---|
| 0.60 | 6069 | 10151 | HIPK4 | homeodomain interacting protein kinase 4 (HIPK4), mRNA. |
| 0.61 | 1324 | 2171 | SIX3 | sine oculis homeobox homolog 3 (*Drosophila*) (SIX3), mRNA. |
| 0.62 | 2695 | 4359 | ZHX2 | zinc fingers and homeoboxes 2 (ZHX2), mRNA. |
| 0.62 | 730 | 1176 | LOC360030 | Homeobox C14 |
| 0.62 | 2611 | 4194 | MSX2 | Msh homeo box homolog 2 (*Drosophila*) |
| 0.63 | 1659 | 2641 | ZFHX2 | PREDICTED: *Homo sapiens* zinc finger homeobox 2 (ZFHX2), mRNA. |
| 0.63 | 2866 | 4538 | HOXA11 | homeo box A11 (HOXA11), mRNA. |
| 0.64 | 1013 | 1580 | HOXB5 | homeo box B5 (HOXB5), mRNA. |
| 0.65 | 1466 | 2263 | VENTX2P1 | VENT-like homeobox 2 pseudogene 1 (VENTX2P1) on chromosome X. |
| 0.67 | 3704 | 5533 | MEOX1 | Mesenchyme homeo box 1 |
| 0.68 | 980 | 1451 | HOXD11 | homeo box D11 (HOXD11), mRNA. |
| 0.69 | 1568 | 2267 | HOXD4 | Homeo box D4 |
| 0.69 | 902 | 1304 | IPF1 | insulin promoter factor 1, homeodomain transcription factor (IPF1), mRNA. |
| 0.70 | 2763 | 3924 | ZHX3 | zinc fingers and homeoboxes 3 (ZHX3), mRNA. |

*Genes listed are those whose expression levels in DKK1-treated keratinocytes were >1,000 (65,000 is the maximum) after 2 hr treatment with DKK1; data for genes with DKK1/NS ratio >1.45 are reported as means of 3 independent experiments.
**Genes listed are those whose expression levels in mock-treated keratinocytes were >1,000 (65,000 is the maximum) after 2 hr treatment with DKK1; data for genes with DKK1/NS ratio <0.70 are reported as means of 3 independent experiments.

TABLE 11

Keratin-Related Genes Up-regulated by Treatment with DKK1 for 2 hr*

| DKK1/NS | DKK1 | NS | Gene | Description |
|---|---|---|---|---|
| 2.10 | 2531 | 1205 | KRT9 | keratin 9 (epidermolytic palmoplantar keratoderma) (KRT9), mRNA. |
| 1.74 | 11545 | 6627 | KRTHB2 | keratin, hair, basic, 2 (KRTHB2), mRNA. |
| 1.47 | 3537 | 2401 | KRT20 | keratin 20 (KRT20), mRNA. |
| 1.46 | 65000 | 44518 | KRT16 | keratin 16 (focal non-epidermolytic palmoplantar keratoderma) (KRT16), mRNA. |
| 0.40 | 857 | 2168 | KRTAP3-2 | keratin associated protein 3-2 (KRTAP3-2), mRNA. |
| 0.50 | 1870 | 3725 | KRTAP4-14 | keratin associated protein 4-14 (KRTAP4-14), mRNA. |
| 0.58 | 11077 | 19009 | KRT1 | keratin 1 (epidermolytic hyperkeratosis) (KRT1), mRNA. |
| 0.58 | 6453 | 11059 | KRTAP2.1A | Keratin associated protein KRTAP2.1A |
| 0.59 | 1598 | 2723 | KRTAP4-8 | Keratin associated protein 4-8 |
| 0.62 | 10754 | 17429 | K6HF | cytokeratin type II (K6HF), mRNA. |
| 0.62 | 7534 | 12104 | KRT4 | keratin 4 (KRT4), mRNA. |
| 0.68 | 946 | 1395 | KRTAP1-3 | keratin associated protein 1-3 (KRTAP1-3), mRNA. |
| 0.68 | 965 | 1417 | HUMCYT2A | cytokeratin 2 (HUMCYT2A), mRNA. |
| 0.68 | 12976 | 19027 | KRT13 | keratin 13 (KRT13), transcript variant 2, mRNA. |
| 0.70 | 2556 | 3648 | KRTAP2-4 | keratin associated protein 2-4 (KRTAP2-4), mRNA. |

**Genes listed are those whose expression levels in mock-treated keratinocytes were >1,000 (65,000 is the maximum) after 2 hr treatment with DKK1; data for genes with DKK1/NS ratio <0.70 are reported as means of 3 independent experiments.

EXAMPLE 8

Expression Patterns of Proteins Related to the Wnt/β-Catenin Signaling Pathway

Figure 9:
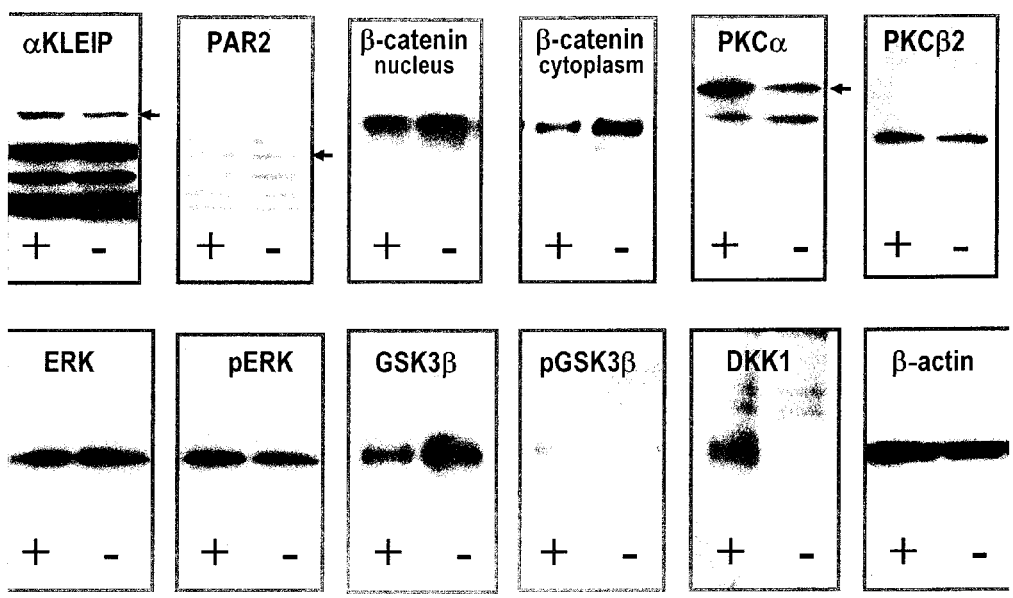
FIG. 9 is a set of digital images of gels showing expression patterns of proteins expressed by keratinocytes three days after transfection with DKK1 (+) or a mock vector (−) and analyzed by Western blot. Expression of αKLEIP (arrow), PAR2 (no specific band recognized), and other proteins as noted are shown. Nuclear and cytoplasmic expression of β-catenin is shown, as is the cytoplasmic expression of PKCα, PKCβ2, total ERK and phosphorylated ERK (pERK), total GSK3β and phosphorylated GSK3β (pGSK3β). DKK1 expression was only seen in DKK1-transfected keratinocytes, as expected. β-actin is shown as a loading control.

This Example illustrates the expression patterns of PAR2, KLEIP and various proteins related with the Wnt/β-catenin signaling pathway. Extracts of keratinocytes were harvested after two hours of treatment with 50 ng/ml rhDKK1 and at three days after transfection with DKK1, and they were analyzed using Western blotting (similar results were found in both protocols, extracts at 3 days after transfection with DKK1 are shown in FIG. 9). For KLEIP, three non-specific bands were found in keratinocytes, as previously reported (Hara et al., *Mol. Biol. Cell* 15:1172-1184, 2004), but the correct band was also detected (at 64 kDa, arrow) for KLEIP whose expression level in keratinocytes was increased in response to DKK1. No recognizable signals for PAR2 were detectable at either time point.

The expression levels of nuclear and cytoplasmic β-catenin were down-regulated after two hours and five days of treatment with DKK1. GSK3β is not only an enzyme involved in the control of glycogen metabolism, but it also regulates a variety of cellular functions including Wnt signaling pathways (Cohen & Goedert, *Nature Rev. Drug Discov.* 3:479-487, 2004). Inactivation of GSK3β via phosphorylation of Ser9 is the major route by which insulin activates muscle glycogen synthase (McManus et al., *EMBO J.* 24:1571-1583, 2005). The expression of GSK3β phosphorylated at Ser9 was investigated, and it was found that it was up-regulated in response to DKK1 at both time points, although overall GSK3β expression was similar at both time points.

Figure 10A:
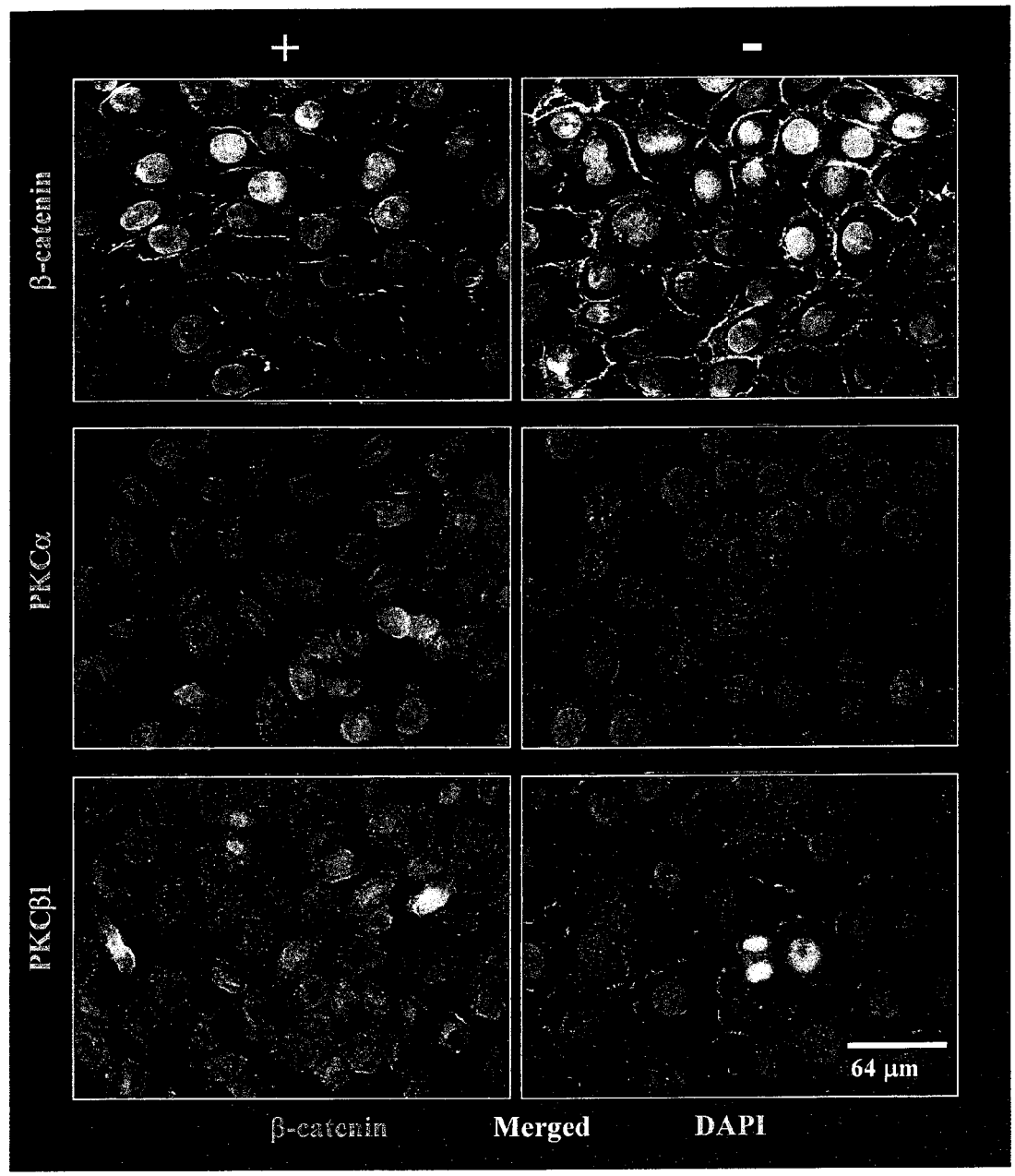
FIG. 10A shows that β-catenin 4(top) expression was down-regulated by DKK1. The expression of PKCα (middle) and PKCβ1 (bottom) was up-regulated by DKK1. β-catenin was stained in all panels; yellow indicates colocalization. Nuclei are identified by DAPI.
Figure 10B:
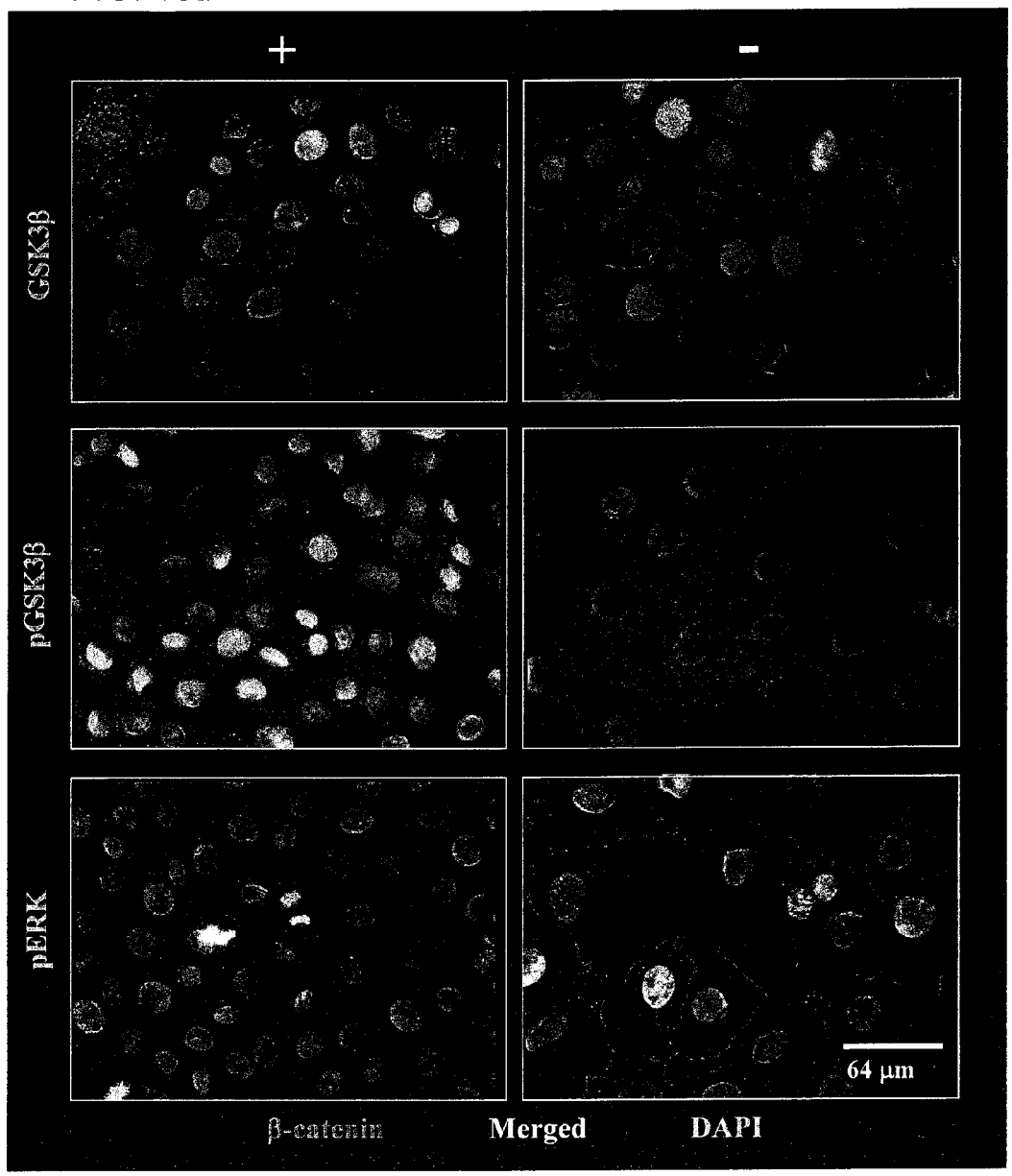
FIG. 10B shows staining patterns of GSK3β (top), pGSK3β (middle) and pERK (bottom) in DKK1-treated keratinocytes. β-catenin and DAPI staining as for FIG. 10A.
Figure 11:
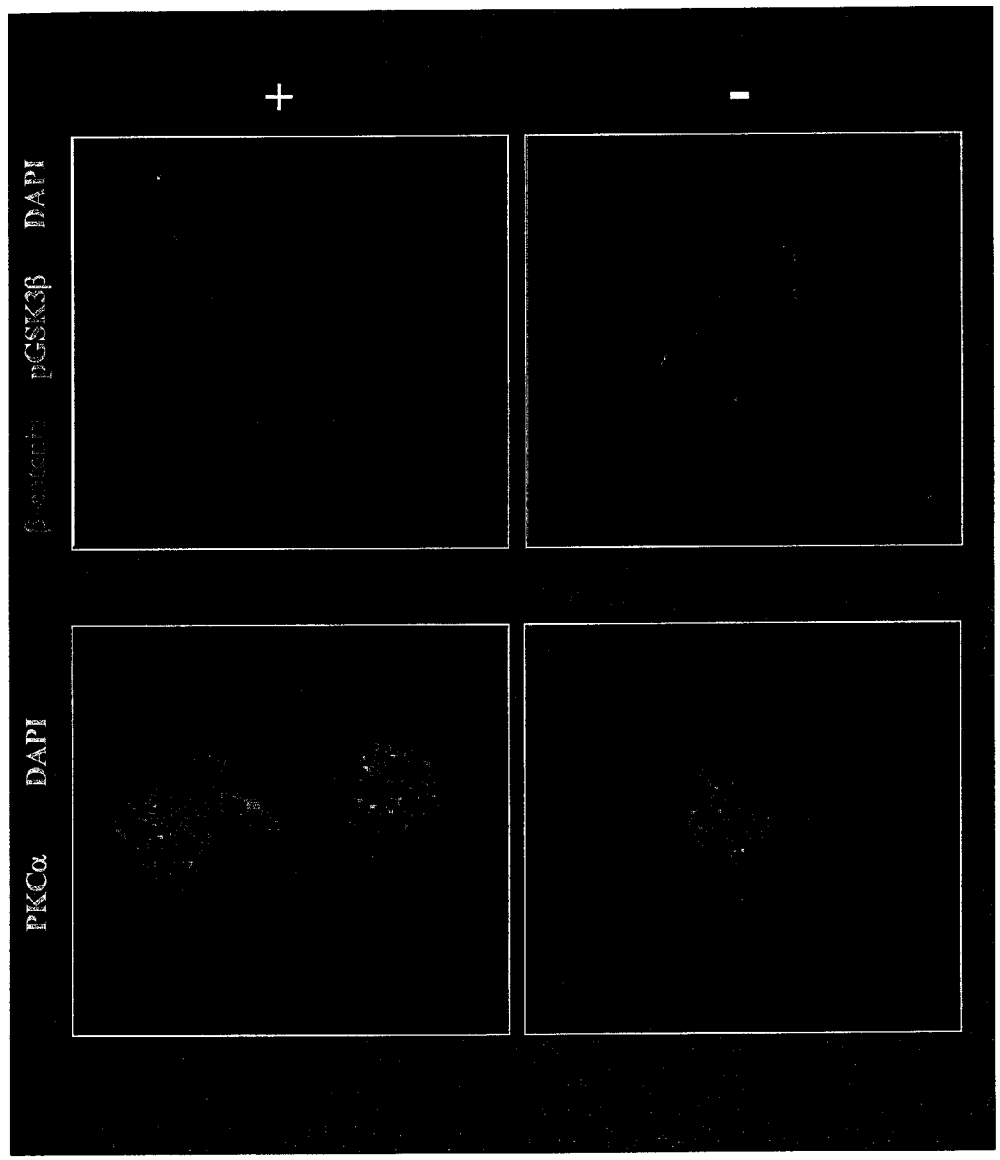
FIG. 11 is a series of digital images showing confocal microscopy of Wnt signaling proteins in keratinocytes treated with (+) or without (−) rhDKK1 for three days. β-catenin (top) expression was down-regulated while pGSK3β (top) and PKCα (bottom) were up-regulated in response to DKK1.

Since PKCα is reported to inactivate GSK3β (Fang et al., *Mol. Cell. Biol.* 22:2099-2100, 2002), the expression of PKC isoforms was examined. Treatment with DKK1 up-regulated the expression of PKCα and PKCβ2 at both time points. Extracellular-signal regulated kinase (ERK) 1/2 plays important roles in keratinocyte proliferation and migration (He et al., *J. Biol. Chem.* 279:53867-53874, 2004; Pullar et al., *FASEB J.* 20:76-86, 2006). Although levels of ERK were not changed by DKK1, expression of the phosphorylated form of ERK1/2 (at Thr202/Tyr204) was up-regulated in response to DKK1. β-actin serves as a loading control. Finally, these expression patterns were validated by immunocytochemistry. The expression of β-catenin was decreased in response to DKK1, whereas that of PKCα and PKCβ1 was increased at 2 hours and 5 days after DKK1 treatment (FIGS. 10 and 11).

Figure 12:
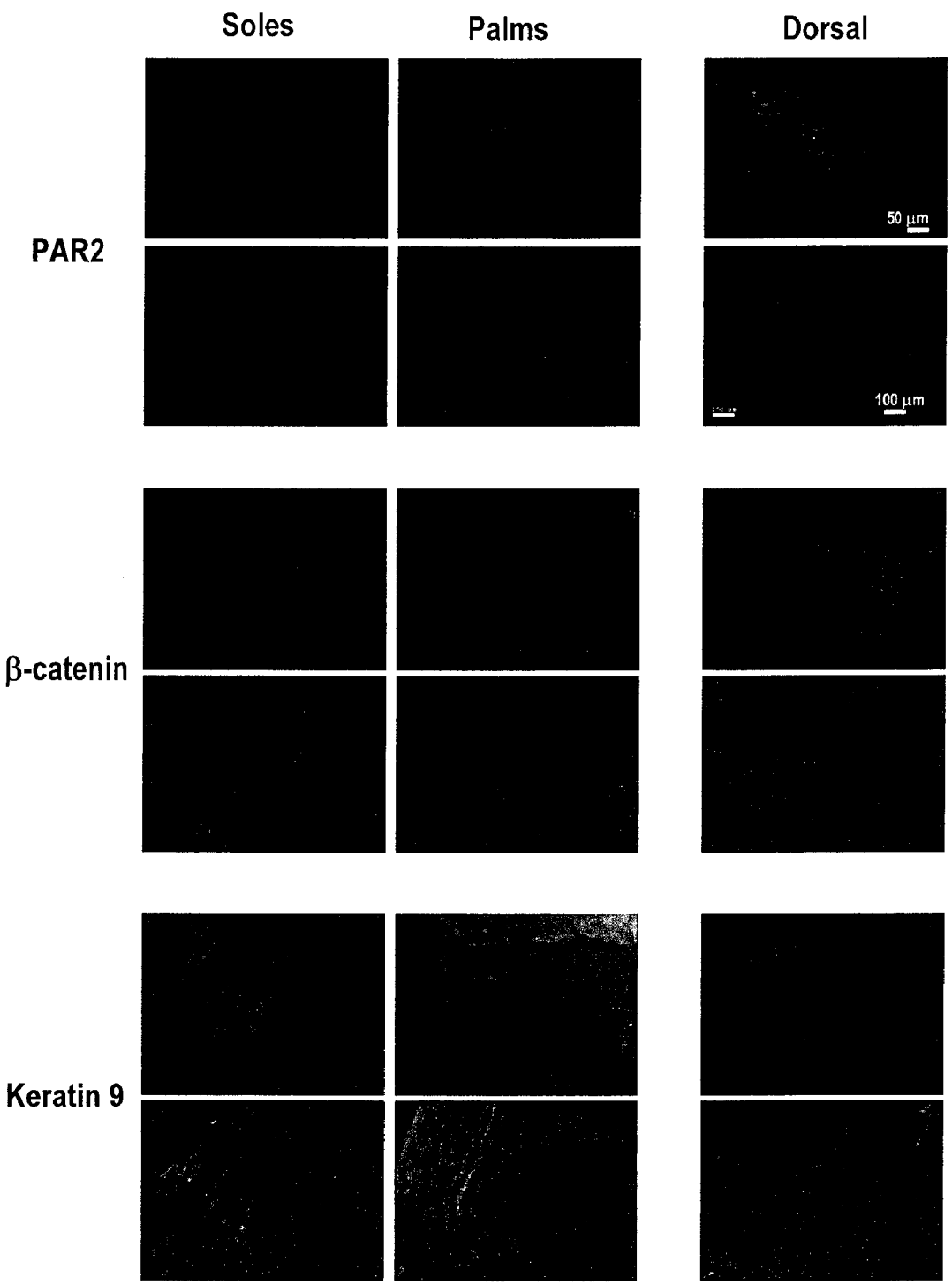
FIG. 12 is a series of digital images showing immunohistochemistry of sole, palm and dorsal skins. The expression of PAR2 and of β-catenin was decreased in palms and soles as compared to dorsal skin. In contrast, keratin 9 was observed only in palmoplantar skin.

The expression patterns of several key keratinocyte proteins identified in the microarray analysis were also studied in vivo using immunohistochemistry in palm and sole skin as compared to nonpalmoplantar trunk skin. The expression of β-catenin and PAR2 was decreased in skin on the palms and soles whereas keratin 9 was only observed in palmoplantar skin (FIG. 12).

EXAMPLE 9

DDK1 Treatment Increased Skin Thickness and Reduced Melanin Content

Figure 13:
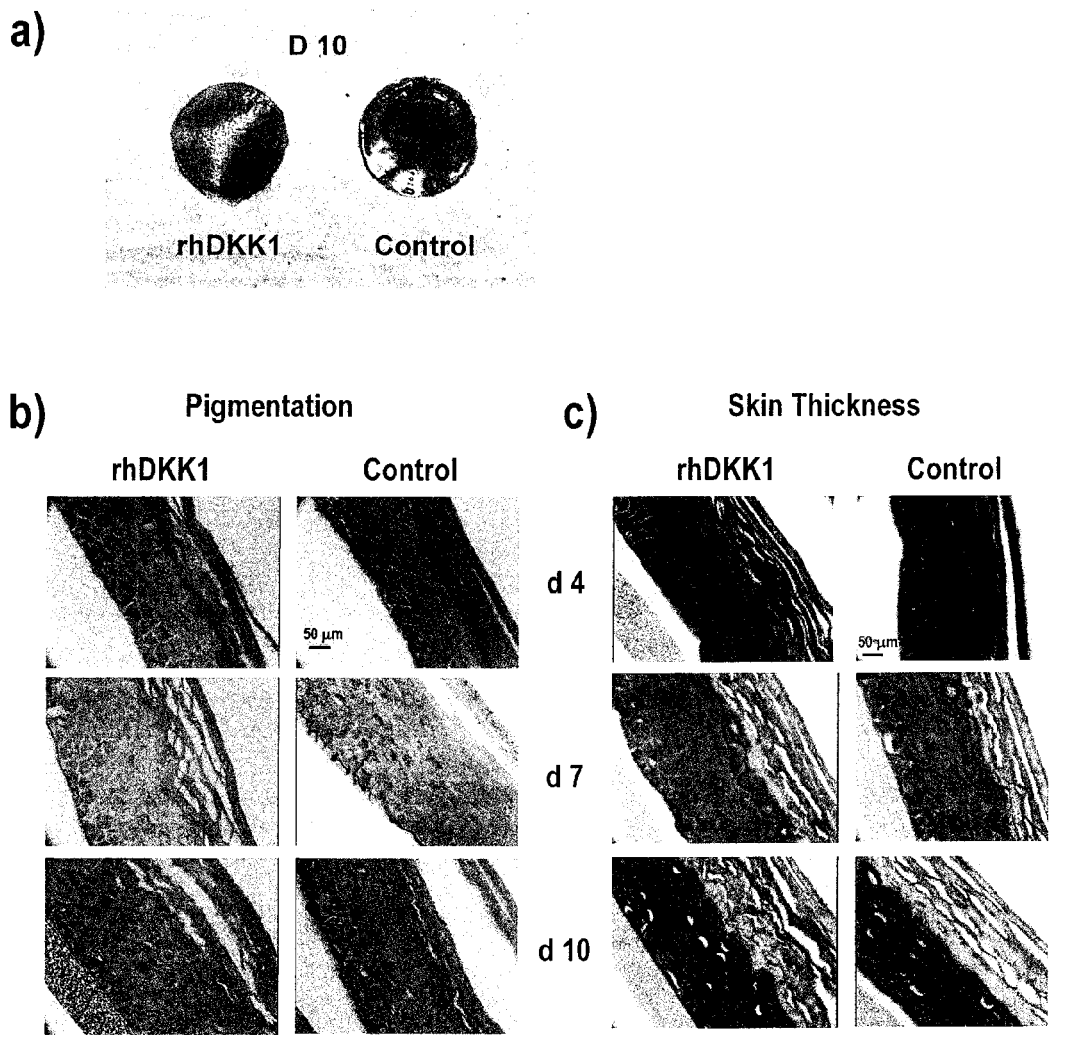
FIG. 13 is a series of digital images showing treatment of MelanoDerm skin reconstructs with DKK1.

This example demonstrates that the secretion of DDK1 by fibroblasts was responsible for the physiological differences observed between palmoplantar skin and nonpalmoplantar skin. Reconstructed skins were grown in the presence or absence of rhDKK1 (FIG. 13). After 7 days, the rhDKK1-treated skins were already significantly less pigmented than the mock-treated controls. The difference was clearer after 7 or 10 days of treatment (FIG. 13A). This difference in pigmentation was confirmed by Fontana-Masson staining which showed a marked decrease in melanin content in rhDKK1-treated skins (FIG. 7B). The skin, and particularly the stratum corneum, were significantly thicker after treatment by rhDDK1 (FIG. 7C).

Figure 14:
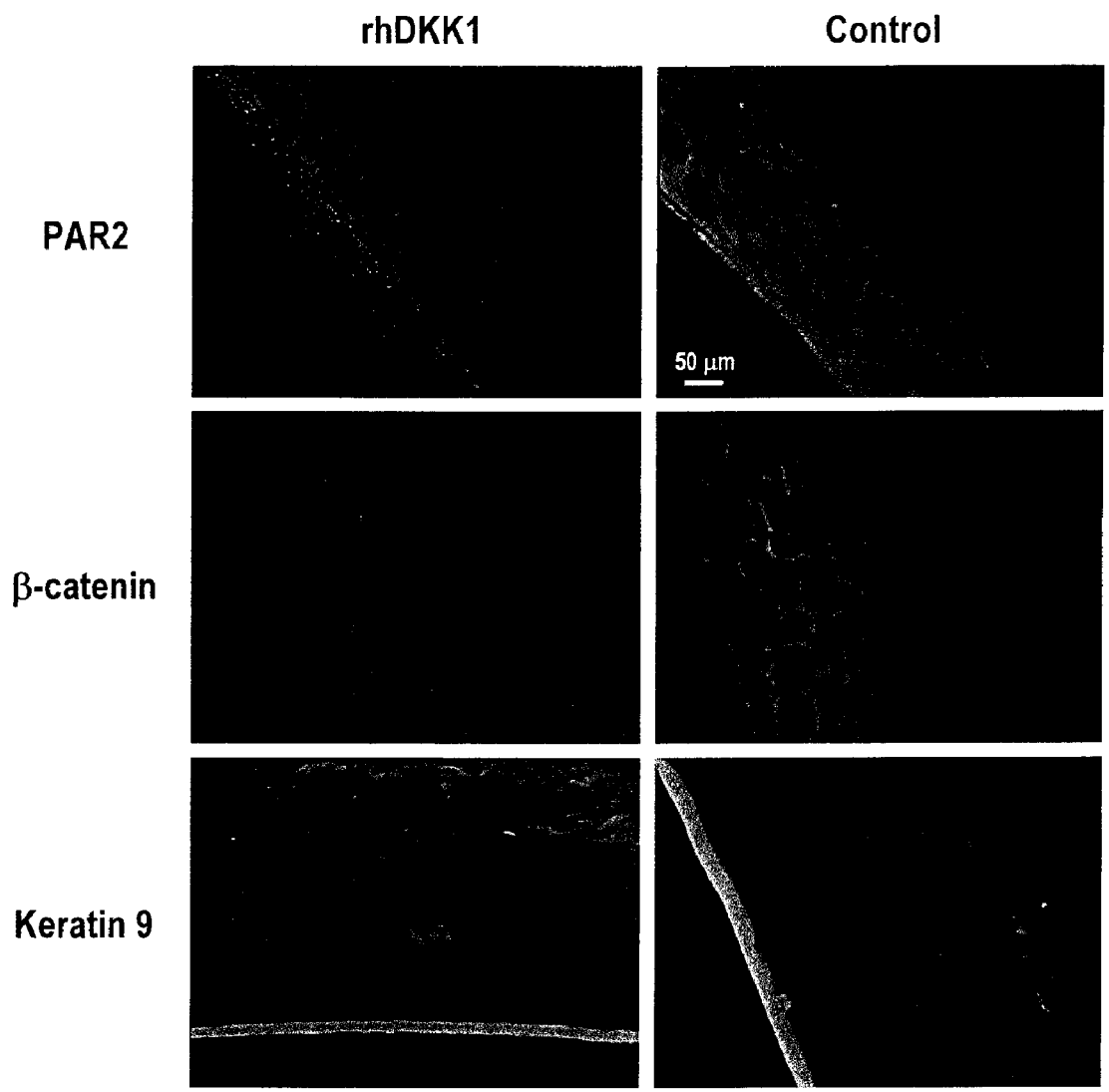
FIG. 14 is a series of digital images showing immunohistochemistry of MelanoDerm reconstructed epidermis. After 10 days of treatment with or without rhDKK1, the expression of PAR2 and β-catenin was down-regulated although some cells positive for keratin 9 were observed.

The immunostaining of these reconstructed skins was consistent with the findings of skin from normal volunteers (as noted above), which revealed decreased expression of PAR2 and β-catenin after 10 days of treatment with rhDDK1 (FIG. 14). Several cells positive for keratin 9 also appeared after 10 days of treatment with rhDKK1.

EXAMPLE 10

Summary of Regulation of Skin Thickness, by DKK1

DKK1, which is secreted at high levels by fibroblasts in palmoplantar skin, decreases melanin uptake by keratinocytes and increases their proliferation. Physiologically, keratinocytes in hypopigmented palmoplantar epidermis are more proliferative (generating a much thicker skin) but at the same time are less pigmented. As demonstrated herein, DKK1 decreases melanin uptake by keratinocytes and increases their proliferation. DNA microarray analysis was used to elucidate these effects, and to compare gene expression patterns of keratinocytes treated or untreated with DKK1.

Regulation of Proliferation and Cell Density

Tulp3, which is ubiquitously expressed throughout embryonic development, belongs to the tubby-like protein family. Tulp3-knockout mice exhibit embryonic lethality with a failure in neural tube closure characterized by neuroepithelial apoptosis (Ikeda et al., *Hum Mol Genet* 10:1325-1334, 2001). The earliest phenotype of Tulp3-knockout mice is a significant reduction in the number of βIII-tubulin-positive neurons in the hindbrain, which suggests that Tulp3 maintains normally differentiating neuronal cell populations. Apoptosis is restricted to the ventral region of the neuroepithelium in the hindbrain of Tulp3-knockout mice, suggesting that Tulp3 is involved in selective cell death in specific types of cells (Ikeda et al., *Hum Mol Genet* 10:1325-1334, 2001; Ikeda et al., *J Cell Sci* 115:9-14, 2002; Carroll et al., *Nat Rev Mol Cell Biol* 5:55-63, 2004). DKK1 down-regulated the expression of Tulp3 in keratinocytes, which indicates that Tulp3 down-regulates the apoptosis of keratinocytes through βIII-tubulin interactions.

KLEIP is a protein that is involved in actin assembly at sites of cell/cell adhesion (Hara et al., *Mol. Biol. Cell* 15:1172-1184, 2004) and which associates with ECT2, a Rho nucleotide exchange factor involved in cytokinesis (Miki et al., *Nature* 362:462-465, 1993; Tatsumoto et al., *J. Cell Biol.* 147:921-928, 1999). Enhanced mRNA and protein expression of KLEIP by DKK1 may account, at least in part, for the enhanced actin assembly and cytokinesis of keratinocytes in palmoplantar skin, which is consistent with their increased proliferation and density in that tissue. DKK1 also enhanced the expression level of keratin 9, which can be induced in non-palmoplantar keratinocytes by palmoplantar fibroblasts (Yamaguchi et al., *J. Invest. Dermatol.* 112:483-488, 1999), which indicates that DKK1 can alter keratin dimerization and patterning in keratinocytes. The altered keratin patterning seen in palmoplantar keratinocytes due to secreted DKK1 also may account for the thick phenotype of palmoplantar epidermis. Further, a slight up-regulation of GJB6 was observed at the mRNA level, which suggests that altered cell/cell communications mediated by gap junctions may also play roles in regulating the proliferation, migration and differentiation of keratinocytes (Brandner et al., *J. Invest. Dermatol.* 122:1310-1320, 2004; Di et al., *J. Cell Sci.* 118:1505-1514, 2005).

In addition to demonstrating the increased expression of KLEIP in response to DKK1 at the mRNA and protein levels, the finding of the decreased expression of cytoplasmic β-catenin (Yamaguchi et al., *J. Cell Biol.* 165:275-285, 2004) may result in decreased cell/cell contact, which suggests that numerous signals are involved in this pathway. Increased expression of PKCα and PKCβs helps explain the increased cell density since PKC isozymes regulate the proliferation and differentiation of keratinocytes (Papp et al., *Exp Dermatol* 12:811-824, 2003). ERK phosphorylation is activated at the healing wound edge. Additionally, β2-adrenergic receptor, whose activation delays wound healing, prevents localization of phospho-ERK to the lamellipodial edge (Pullar et al., *FASEB J.* 20:76-86, 2006). ERK activation in response to DKK1 may also play a role in the stimulation of keratinocyte proliferation and the increased cellular density since ERK is also an important suppressive regulator of apoptosis (He et al., *J Biol Chem* 279:53867-53874, 2004). Canonical Wnt signals activate β-catenin expression through the inhibition of β-catenin degradation by multiple protein complexes including GSK3β, axin and APC. However, Wnt-5a inhibits the canonical Wnt pathway by promoting GSK3β-independent β-catenin degradation (Topol et al., *J. Cell Biol.* 162:899-908, 2003). GSK3β is a unique protein in that it is inactivated through phosphorylation (Cohen and Frame, *Nature Rev: Mol. Cell Biol.* 2:769-776, 2001). Although DKK1 did not affect the overall expression level of GSK3β, the finding of the elevated phosphorylation of GSK3β at Ser9 in response to DKK1 supports a novel pathway for DKK1/Wnt/β-catenin signaling.

P4HA2, prolyl-4-hydroxylase α-subunit (α2), plays roles in collagen fiber formation, probably in response to hypoxia-inducible transcription factor 1 (Hofbauer et al., *Eur. J. Biochem.* 270:4515-4522, 2003; Mackay et al., *Oncogene* 22:2680-2688, 2003; Jarzab et al., *Cancer Res* 65:1587-1597, 2005). DKK1 down-regulates the expression of P4HA2 in keratinocytes, hence the appearance of the dermis in palmoplantar areas might also differ from non-palmoplantar areas due to the down-regulated expression of this hydroxylase.

Regulation of Pigmentation Production and Distribution

DKK1 significantly inhibits the uptake of melanin granules by keratinocytes, and thereby decreases pigment in the epithelium. PAR2 is expressed on keratinocytes and is involved in melanin uptake via phagocytosis (Seiberg et al., *Exp. Cell Res.* 254:25-32, 2000) in a Rho-dependent fashion (Scott et al., *J Invest Dermatol* 121:529-541, 2003). PAR2 plays a significant role in modulating pigmentation in a skin type-dependent manner (Babiarz-Magee et al., *Pigment Cell Res.* 17:241-251, 2004) and in response to UV (Scott et al., *J. Invest. Dermatol.* 117:1412-1420, 2001). Thus, the decreased melanin uptake elicited in keratinocytes by DKK1 may in large part be mediated through the suppressed expression of PAR2. DKK1 might also decrease the secretion of melanosomes by melanocytes.

Although detectable levels of MITF protein were not observed in keratinocytes, differential display and RT-PCR showed that DKK1 suppresses the expression of MITF mRNA in those cells. Thus, keratinocytes express MITF at the mRNA level but do not make detectable levels of MITF protein. However, this result indicates that not only does DKK1 suppress MITF expression in melanocytes (Garraway et al., *Nature* 436:117-122, 2005) but also in keratinocytes. The decreased uptake of melanin granules by keratinocytes elicited by DKK1 is significant.

Physiological Impact of DKK1

Several key proteins regulated by DDK1 in vitro showed the same expression patterns between palmoplantar epidermis and dorsal epidermis in vivo. Indeed, the expression levels of PAR2 and β-catenin were less in palmoplantar skin compared to dorsal epidermis. In contrast, keratin 9 was found in all suprabasal layers of palmoplantar epidermis and was almost absent in dorsal skin. These patterns of protein expression were reproduced in reconstructed epidermis (MelanoDerm®) consisting of cultured human melanocytes and keratinocytes after 10 days of treatment with rhDKK1. Not only the expression of PAR2 and β-catenin were decreased but several cells stained positively for keratin 9 in the rhDKK1-treated skin substitutes. Keratin 9 is normally observed only in palmoplantar epidermis (Knapp et al., *J. Cell Biol.* 103:657-667, 1986) and its defective function is a cause of epidermolytic palmoplantar keratoderma (Langbein et al., *Differentiation* 55:57-71, 1993; Kobayashi et al., *FEBS Lett.* 386:149-155, 1996). The rhDKK1-treated epidermis also had less melanin and a thicker stratum corneum and this tendency to thicken became more significant as the treatment time increased. These changes were so dramatic that they were visually detectable after 7 days of treatment, and were obvious after 10 days. Although a number of other cells and interactions no doubt also contribute to the regulation of skin morphology and pigmentation, the fact that DKK1 can recapitulate the palmoplantar phenotype in the reconstituted skin model emphasizes its key role in those processes. Thus, DKK1 by itself was sufficient to induce a palmoplantar phenotype in a reconstructed epidermis.

Conclusions

Numerous up-regulated and down-regulated receptors and HOX-related genes were found that responded to DKK1, indicating that DKK1 can serve as a ligand (agonist) or an antagonist for those receptors and can affect the topographical/site-specific/anatomically specific distribution of HOX in the human body. Taken together, DKK1 has various effects on keratinocyte growth and function, including the up-regulation of cell density and the decreased melanin uptake, probably through numerous effects on gene expression patterns.

In conclusion, these findings elucidate why palmoplantar epidermis is thicker and paler than non-palmoplantar epidermis. In addition to dermal/epidermal interactions, which play important roles in regulating keratinocyte growth and differentiation through numerous growth factors (Szabowski et al., *Cell* 103:745-755, 2000), the necessity of those topographical/site-specific regulations have been proposed (Yamaguchi et al., *J. Dermatol. Sci.* 40:1-9, 2005). DKK1, a secretory protein highly expressed by palmoplantar fibroblasts (Yamaguchi et al., *J. Cell Biol.* 165:275-285, 2004) has various effects on keratinocytes, the major type of cell in the epidermis. Enhanced KLEIP expression in response to DKK1 may play a role in the enhanced cell contraction (compact cellular organization) in palmoplantar keratinocytes stimulated with DKK1. Additionally, the decreased expression of β-catenin in the cytoplasm of keratinocytes that is elicited by DKK1 may result in the loose cell/cell contact and the increased cellular density seen in palmoplantar epidermis, in which suprabasal keratin 9 expression is also seen (Knapp et al., *J. Cell Biol.* 103:657-667, 1986). PKC isozymes and GSK3β may participate in DKK1/Wnt/β-catenin signaling pathways. The fact that DKK1 decreases melanocyte function and proliferation through MITF (Yamaguchi et al., *J. Cell Biol.* 165:275-285, 2004) and that melanosome transfer is decreased in keratinocytes in response to DKK1 (probably through PAR2) explains the hypopigmentation seen in the skin on palms and soles.

In view of the many possible embodiments to which the principles of our invention may be applied, it should be recognized that the illustrated embodiment is only a preferred example of the invention and should not be taken as a limitation on the scope of the invention. Rather, the scope of the invention is defined by the following claims. We therefore claim as our invention all that comes within the scope and spirit of these claims.

---

We claim:

1. A method for inducing non-palmoplantar skin to develop a palmoplantar phenotype, the method comprising topically applying an effective amount of dickkopf 1 (DKK1) to non-palmoplantar skin, thereby inducing the non-palmoplantar skin to develop a palmoplantar phenotype.

2. The method of claim 1, wherein the palmoplantar phenotype is increased skin thickness.

3. The method of claim 2, wherein the method is an in vitro method.

4. The method of claim 1, wherein the non-palmoplantar skin comprises a skin graft, an ulcer, an abrasion, an injury caused by a repetitive impact or mechanical stress, age-related skin changes, or skin damage due to steroid treatment.

5. The method of claim 4, wherein the ulcer is a foot ulcer.

6. The method of claim 5, wherein the subject has diabetes.

7. The method of claim 4, wherein the skin graft is on a foot.

8. The method of claim 2, wherein the non-palmoplantar skin is on a hand.

9. The method of claim 1, wherein the palmoplantar phenotype is reduced skin pigmentation.

10. The method of claim 9, wherein the method is an in vitro method.

11. The method of claim 9, wherein the DKK1 is topically applied to a pigmented area of skin on a subject.

12. The method of claim 11, wherein the non-palmoplantar skin comprises uneven skin pigmentation, hyperpigmentation, post-inflammatory pigmentation, ephelides, fragrance dermatitis, sun-damaged skin, vitiligo, a pigmented birthmark, lentigos, a café au lait spot, lichen simplex chronicus, melasma, porphyria cutanea tarda, or acanthosis nigricans.

13. The method of claim 1, wherein the palmoplantar phenotype is reduced hair growth.

14. The method of claim 13, wherein the DKK1 is topically applied to an area of skin on a subject, wherein unwanted hair is growing on the area of skin.

15. The method of claim 1, wherein the DKK1 is topically applied to an area of skin on a subject, wherein the area of skin contains a pigmented lesion suspected of being a pre-melanoma lesion.

16. The method of claim 14, wherein the area of skin is on an upper or lower extremity or is axillary skin.

17. The method of claim 11, wherein the subject has hirsutism, congenital adrenal hyperplasia, polycystic ovarian syndrome, hypertrichosis, porphyria cutanea tarda, or anorexia nervosa.

18. The method of claim 1, wherein the non-palmoplantar skin is on a trunk, head, arm, or leg.

19. The method of claim 1, wherein the non-palmoplantar skin is on a finger or toe.

20. The method of claim 1, wherein the non-palmoplantar skin is on a face.

21. The method of claim 1, wherein the non-palmoplantar skin is present on a human subject, and topically applying the effective amount of DKK1 to non-palmoplantar skin comprises topically applying the effective amount of DKK1 to non-palmoplantar skin on the human subject.

22. The method of claim 1, wherein topically applying the effective amount of DKK1 to non-palmoplantar skin comprises transdermal administration.

23. The method of claim 1, wherein the DKK1 is present in a pharmaceutical composition comprising an emulsion.

24. The method of claim 21, wherein the effective amount of DKK1 is 0.01 μg to 10 g per kg body weight of the subject.

* * * * *